United States Patent
Goulet et al.

(10) Patent No.: US 6,200,957 B1
(45) Date of Patent: Mar. 13, 2001

(54) ANTAGONISTS OF GONADOTROPIN RELEASING HORMONE

(75) Inventors: Mark Goulet, Westfield; Wallace T. Ashton, Clark; Lin Chu, Scotch Plains; Michael H. Fisher, Ringoes; Peter Lin, Edison; Mitree M. Ponpipom, Branchburg; Matthew J. Wyvratt, Mountainside; Narindar N. Girotra, Old Bridge; Jonathan Young, Dayton, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/115,497

(22) Filed: Jul. 14, 1998

Related U.S. Application Data

(63) Continuation-in-part of application No. 08/760,816, filed on Dec. 5, 1996, now Pat. No. 5,780,437.
(60) Provisional application No. 60/008,633, filed on Dec. 14, 1995.

(51) Int. Cl.[7] ........................ C07D 209/10; C07D 403/06
(52) U.S. Cl. .......................... 514/19; 514/2; 514/226.8; 514/228.2; 514/422; 546/126; 546/131; 546/128; 546/127; 546/136; 546/146; 544/238; 544/242; 544/96; 544/255; 544/336; 544/349
(58) Field of Search ................... 514/19, 226.8, 514/228.21, 422; 546/126, 131, 146, 127, 128, 136; 544/238, 242, 336, 96, 349, 255

(56) References Cited

U.S. PATENT DOCUMENTS

| | | | |
|---|---|---|---|
| 4,139,634 | 2/1979 | Pigerol et al. | 424/274 |
| 4,252,803 | 2/1981 | Webb | 424/248.5 |
| 4,544,663 | 10/1985 | Manning et al. | 514/378 |
| 4,943,572 | 7/1990 | von Angerer | 514/235.2 |
| 5,030,640 | 7/1991 | Fisher et al. | 514/339 |
| 5,378,688 | * 1/1995 | Nett et al. | 514/15 |
| 5,756,507 | 5/1998 | Goulet et al. | 514/255 |
| 5,780,437 | 7/1998 | Goulet et al. | 514/19 |
| 5,849,764 | * 12/1998 | Goulet et al. | 514/337 |

FOREIGN PATENT DOCUMENTS

| | | |
|---|---|---|
| 0 219 292 A2 | 4/1987 | (EP) . |
| 0 679 642 A1 | 11/1995 | (EP) . |
| 2181559 | 4/1972 | (FR) . |
| WO90/05721 | 5/1990 | (WO) . |
| WO95/28405 | 10/1995 | (WO) . |
| WO95/29900 | 11/1995 | (WO) . |
| WO 97/21703 | 6/1997 | (WO) . |
| WO 97/21704 | 6/1997 | (WO) . |

OTHER PUBLICATIONS

Pharmazie, vol. 35, No. 12, pp. 742–743 (1980), by S. Tiwari, et al.
J. Med. Chem., vol. 32, No. 9, pp. 2036–2038 (1989), by Biswanath De, et al.
Current Opinion in Obstetrics & Gynecology, vol. 6, pp. 262–268 (1994), by R. A. Loy.
CA 80:108368, FR 2181559, by Boch, et al.

\* cited by examiner

Primary Examiner—Bennett Celsa
(74) Attorney, Agent, or Firm—Elliott Korsen; Mark R. Daniel

(57) ABSTRACT

There are disclosed compounds of formula (I)

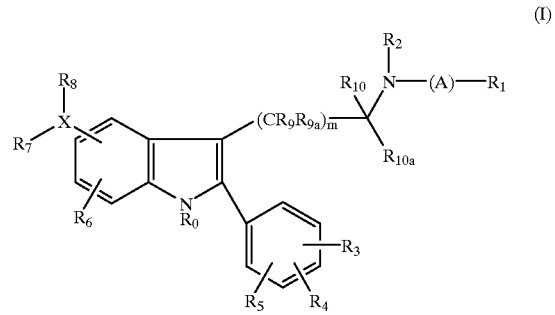

and pharmaceutically acceptable salts thereof which are useful as antagonists of GnRH and as such may be useful for the treatment of a variety of sex-hormone related and other conditions in both men and women.

8 Claims, No Drawings

ANTAGONISTS OF GONADOTROPIN RELEASING HORMONE

This application is a continuation-in-part of application Ser. No. 08/760,816, filed Dec. 5, 1996 now U.S. Pat. No. 5,780,437 which claims benefit of U.S. Ser. No. 60/008,633 Dec. 14, 1995.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral adminstration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine. WO 97/21435, WO 97/21703, WO 97/21707 and WO 97/21704 disclose non-peptidyl, indole derivatives as GnRH antagonists.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, such as growth hormone secretagogues, e.g. MK-0677, for the treatment and prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5a-reductase 2 inhibitor, such as finasteride or epristeride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoro-methylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

DETAILED DESCRIPTION OF THE INVENTION

The present invention relates to compounds of the general formula

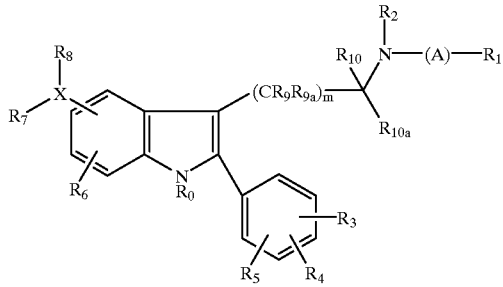

(I)

wherein

A is C₁–C₆ alkyl, substituted C₁–C₆ alkyl, C₃–C₇ cycloalkyl, substituted C₃–C₇ cycloalkyl, C₃–C₆ alkenyl, substituted C₃–C₆ alkenyl, C₃–C₆ alkynyl, substituted C₃–C₆ alkynyl, C₁–C₆ alkoxy, or C₀–C₅ alkyl-S(O)$_n$-C₀–C₅ alkyl, C₀–C₅ alkyl-O-C₀–C₅ alkyl, C₀–C₅ alkyl-NR₁₈-C₀–C₅ alkyl where R₁₈ and the

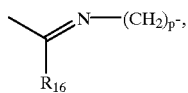

C₀–C₅ alkyl can be joined to form a ring, or a single bond;

R₀ is hydrogen, C₁–C₆ alkyl, substituted C₁–C₆ alkyl, wherein the substituents are as defined below; aryl, substituted aryl, aralkyl or substituted aralkyl, wherein the substituents are as defined for R₃, R₄ and R₅;

R₁ is

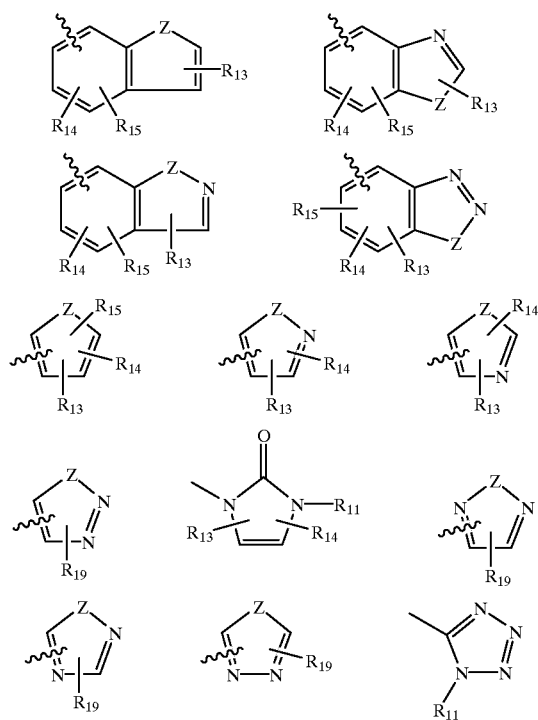

-continued

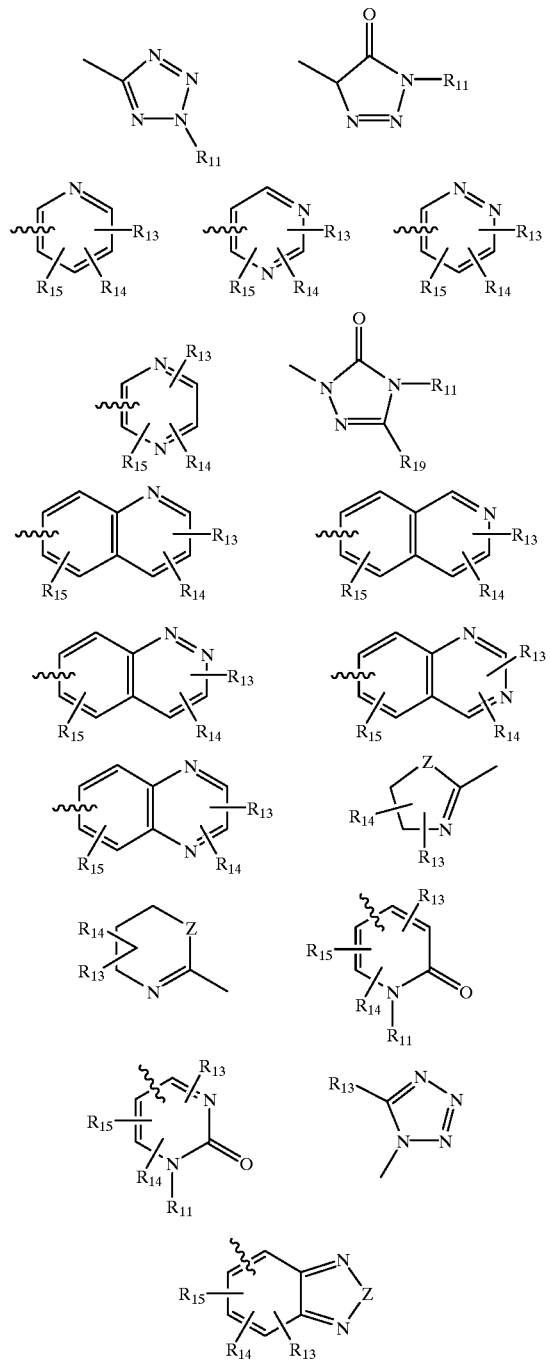

the nitrogen atoms contained in the R₁ heteroaromatic rings may exit either as drawn or, when chemically allowed, in their oxidized (N→O, N—OH) state;

R₂ is hydrogen, C₁–C₆ alkyl, substituted C₁–C₆ alkyl, aralkyl, substituted aralkyl, aryl, substituted aryl, alkyl —OR₁₁, C₁–C₆(NR₁₁R₁₂), C₁–C₆(CONR₁₁R₁₂) or C(NR₁₁R₁₂)NH;

R₂ and A taken together form a ring of 5–7 atoms;

R₃, R₄ and R₅ are independently hydrogen, C₁–C₆ alkyl, substituted C₁–C₆ alkyl, C₂–C₆ alkenyl, substituted C₂–C₆ alkenyl, CN, nitro, C₁–C₃ perfluoroalkyl, C₁–C₃ perfluoroalkoxy, aryl, substituted aryl, aralkyl, substituted aralkyl, R₁₁O(CH₂)$_p$—, R₁₁C(O)O(CH₂)$_p$—, $R_{11}OC(O)(CH_2)_p-$, $-(CH_2)_pS(O)_nR_{17}$, $-(CH_2)_pC(O)NR_{11}R_{12}$ or halogen; wherein $R_{17}$ is hydrogen, $C_1-C_6$ alkyl, $C_1-C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1-C_6$ alkyl, substituted $C_1-C_6$ alkyl, aryl, substituted aryl, $C_1-C_3$ perfluoroalkyl, CN, $NO_2$, halogen, $R_{11}O(CH_2)_p-$, $NR_{21}C(O)R_{20}$, $NR_{21}C(O)NR_{20}R_{21}$ or $SO_nR_{20}$;

$R_7$ is hydrogen, $C_1-C_6$ alkyl, or substituted $C_1-C_6$ alkyl, unless X is hydrogen or halogen, then $R_7$ is absent;

$R_8$ is $C(O)OR_{20}$, $C(O)NR_{20}R_{21}$, $NR_{20}R_{21}$, $C(O)R_{20}$, $NR_{21}C(O)R_{20}$, $NR_{21}C(O)NR_{20}R_{21}$, $NR_{20}S(O)_2R_{21}$, $NR_{21}S(O)_2NR_{20}R_{21}$, $OC(O)R_{20}$, $OC(O)NR_{20}R_{21}$, $OR_{20}$, $SO_nR_{20}$, $S(O)_nNR_{20}R_{21}$, a heterocyclic ring or bicyclic heterocyclic ring with from 1 to 4 heteroatoms selected from N, O or S which can be optionally substituted by $R_3$, $R_4$ and $R_5$, $C_1-C_6$ alkyl or substituted $C_1-C_6$ alkyl; or $R_7$ and $R_8$ taken together form a heterocyclic ring containing one or more heteroatoms selected from N, O or S which can be optionally substituted by $R_3$, $R_4$ and $R_5$;

$R_9$ and $R_{9a}$ are independently hydrogen, $C_1-C_6$ alkyl, substituted $C_1-C_6$ alkyl; aryl or substituted aryl, aralkyl or substituted aralkyl when m≠0; or $R_9$ and $R_{9a}$ taken together form a carbocyclic ring of 3–7 atoms or

when m≠0;

$R_9$ and A taken together form a heterocyclic ring containing 3–7 carbon atoms and one or more heteroatoms when m≠0; or $R_{10}$ and $R_{10a}$ are independently hydrogen, $C_1-C_6$ alkyl, substituted $C_1-C_6$ alkyl, aryl, substituted aryl, aralkyl or substituted aralkyl; or $R_{10}$ and $R_{10a}$ taken together form a carbocyclic ring of 3–7 atoms or

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1-C_6$ alkyl, substituted $C_1-C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1-C_6$ alkyl), $NR_{11}SO_2$(substituted $C_1-C_6$ alkyl), $NR_{11}SO_2$(aryl), $NR_{11}SO_2$(substituted aryl), $NR_{11}SO_2(C_1-C_3$ perfluoroalkyl); $SO_2NR_{11}(C_1-C_6$ alkyl), $SO_2NR_{11}$(substituted $C_1-C_6$ alkyl), $SO_2NR_{11}$(aryl), $SO_2NR_{11}$(substituted aryl), $SO_2NR_{11}(C_1-C_3$ perfluoroalkyl); $SO_2NR_{11}(C(O)C_1-C_6$ alkyl); $SO_2NR_{11}(C(O)$-substituted $C_1-C_6$ alkyl); $SO_2NR_{11}(C(O)$-aryl); $SO_2NR_{11}(C(O)$-substituted aryl); $S(O)_n(C_1-C_6$ alkyl); $S(O)_n$(substituted $C_1-C_6$ alkyl), $S(O)_n$(aryl), $S(O)_n$(substituted aryl), $C_1-C_3$ perfluoroalkyl, $C_1-C_3$ perfluoroalkoxy, $C_1-C_6$ alkoxy, substituted $C_1-C_6$ alkoxy, COOH, halogen, $NO_2$ or CN;

$R_{14}$ and $R_{15}$ are independently hydrogen, $C_1-C_6$ alkyl, substituted $C_1-C_6$ alkyl, $C_2-C_6$ alkenyl, substituted $C_2-C_6$ alkenyl, CN, nitro, $C_1-C_3$ perfluoroalkyl, $C_1-C_3$ perfluoroalkoxy, aryl, substituted aryl, aralkyl, substituted aralkyl, $R_{11}O(CH_2)_p-$, $R_{11}C(O)O(CH_2)_p-$, $R_{11}OC(O)(CH_2)_p-$, $-(CH_2)_pS(O)_nR_{17}$, $-(CH_2)_pC(O)NR_{11}R_{12}$ or halogen; wherein $R_{17}$ is hydrogen, $C_1-C_6$ alkyl, $C_1-C_3$ perfluoroalkyl, aryl or substituted aryl;

$R_{16}$ is hydrogen, $C_1-C_6$ alkyl, substituted $C_1-C_6$ alkyl, or $N(R_{11}R_{12})$;

$R_{18}$ is hydrogen, $C_1-C_6$ alkyl, substituted $C_1-C_6$ alkyl, $C(O)OR_{11}$, $C(O)NR_{11}R_{12}$, $C(O)R_{11}$, $S(O)_nR_{11}$;

$R_{19}$ is either the definition of $R_{13}$ or $R_{14}$;

$R_{20}$ and $R_{21}$ are independently hydrogen, $C_1-C_6$ alkyl, substituted $C_1-C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1-C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{20}$ and $R_{21}$ taken together can form an optionally substituted ring of 3–7 atoms;

X is N, O, $S(O)_n$, C(O), $(CR_{11}R_{12})_p$, a single bond to $R_8$, $C_2-C_6$ alkenyl, substituted $C_2-C_6$ alkenyl, $C_2-C_6$ alkynyl, or substituted $C_2-C_6$ alkynyl; when X is O, $S(O)_n$, C(O), or $CR_{11}R_{12}$ only $R_8$ is possible;

Z is O, S or $NR_{11}$;

m is 0–3;

n is 0–2;

p is 0–4; and the alkyl, cycloalkyl, alkenyl and alkynyl substituents are selected from $C_1-C_6$ alkyl, $C_3-C_7$ cycloalkyl, aryl, substituted aryl, aralkyl, substituted aralkyl, hydroxy, oxo, cyano, $C_1-C_6$ alkoxy, fluoro, $C(O)OR_{11}$, aryl $C_1-C_3$ alkoxy, substituted aryl $C_1-C_3$ alkoxy, and the aryl substituents are as defined for $R_3$, $R_4$ and $R_5$; or a pharmaceutically acceptable addition salt and/or hydrate thereof, or where applicable, a geometric or optical isomer or racemic mixture thereof.

Preferred substituents when $R_{20}$ and $R_{21}$ are taken together include 7-aza-bicyclo [2.2.1]heptane and 2-aza-bicyclo [2.2.2] octane.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "aryl" includes phenyl and naphthyl. Preferably, aryl is phenyl.

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituents are as defined above unless indicated otherwise.

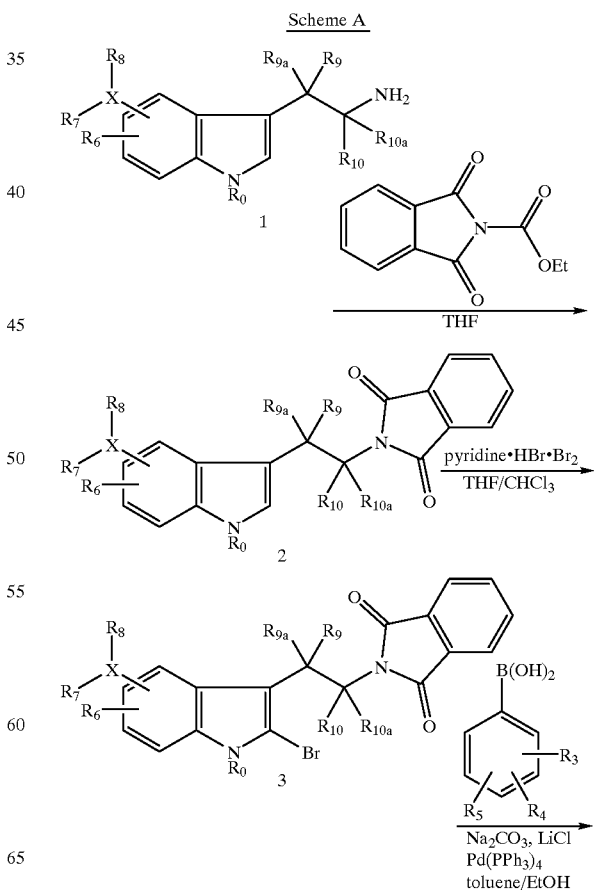

-continued

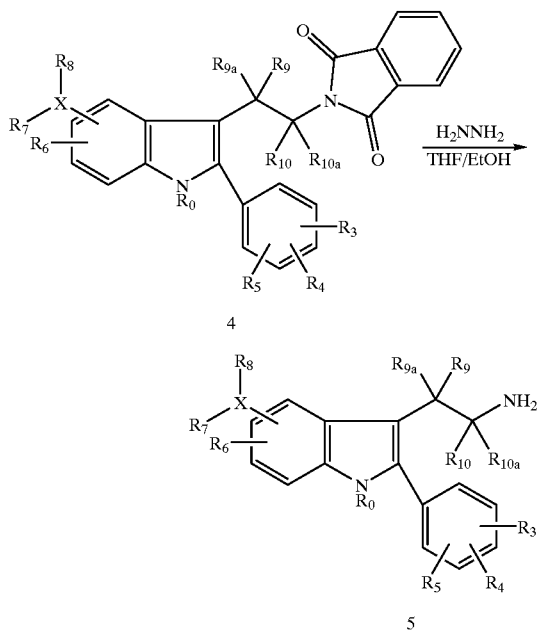

Reaction Scheme A

As shown in reaction Scheme A, treatment of tryptamine (1) with N-carboxyphthalimide in an inert organic solvent such as tetrahydrofuran at a temperature of 20–65° C., preferably 65° C., for a period of 12–48 hours gives the corresponding N-phthalimidotryptamine derivative (2). The NIV-phthalimidotryptamine (2) could be further modified by treatment with a brominating agent such as pyridinium hydrobromide perbromide, pyrrolidone hydrotribromide, or the like in an inert organic solvent such as tetrahydrofuran, methylene chloride, chloroform, or mixtures thereof at 0–25° C. for a period of 30 minutes to 4 hours to provide the 2-bromotryptamine (3). Bromide (3) may be reacted with an arylboronic acid (prepared essentially as described in Gronowitz, S.; Hornfeldt, A.-B.; Yang, Y.-H. *Chem. Scr.* 1986,26, 311–314.) with palladium (O) catalysis, a weak base such as aqueous sodium carbonate or the like, and a chloride source such as lithium chloride in an inert solvent like toluene, benzene, ethanol, propanol or mixtures thereof at a temperature of 25°–100° C., preferably 80° C., for a period of 1–6 hours to give the 2-aryltryptamine derivative (4). Finally, the phthalimido group may be removed by treatment of (4) with aqueous hydrazine in an inert solvent such as methanol or ethanol at a temperature of 0°–25° C. for a period of 4–24 hours to give tryptamine (5).

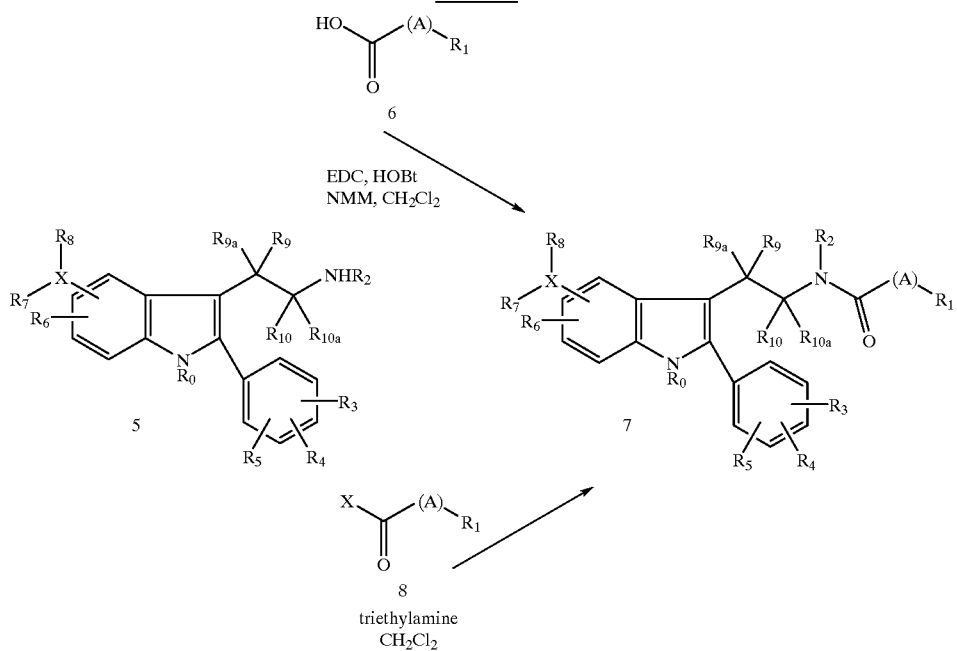

Reaction Scheme B

As shown in reaction Scheme B, the 2-aryltryptamine may be condensed with a carboxylic acid of type (6) using the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (7). Alternatively, 2-aryltryptamine (5) can be treated with an active ester or acid chloride of type (8) in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give (7).

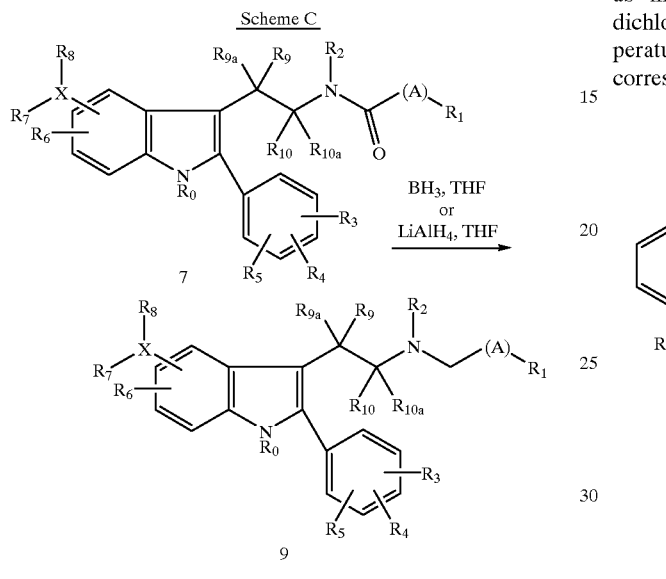

Reaction Scheme C

As shown in reaction Scheme C, the amide carbonyl of (7) can be reduced by treatment with borane, lithium aluminum hydride, or equivalent hydride sources in an inert organic solvent such as tetrahydrofuran, diethyl ether, 1,4-dioxane or the like at 25°–100° C., preferably 65° C., for a period of 1–8 hours to give the corresponding amine compound (9).

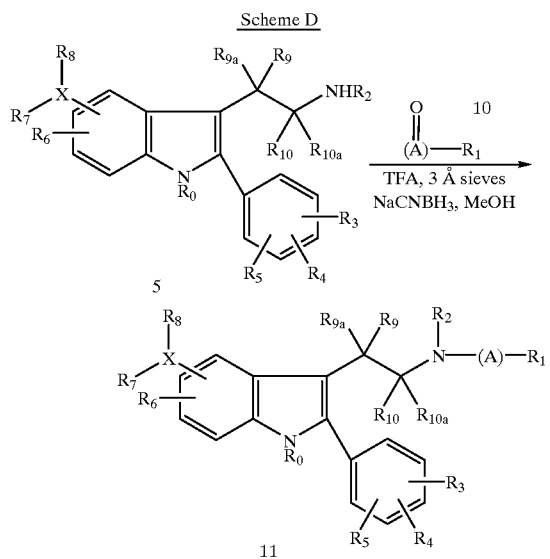

Reaction Scheme D

As shown in reaction Scheme D, the 2-aryltryptamine (5) can be modified by treatment with an aldehyde or ketone of type (10) in the presence of a weak acid such as trifluoroacetic acid (TFA), acetic acid or the like, with or without a dessicant such as 3 Å molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of 0°–25° C. for a preiod of 1–12 hours to give the corresponding secondary or tertiary amine derivative (11).

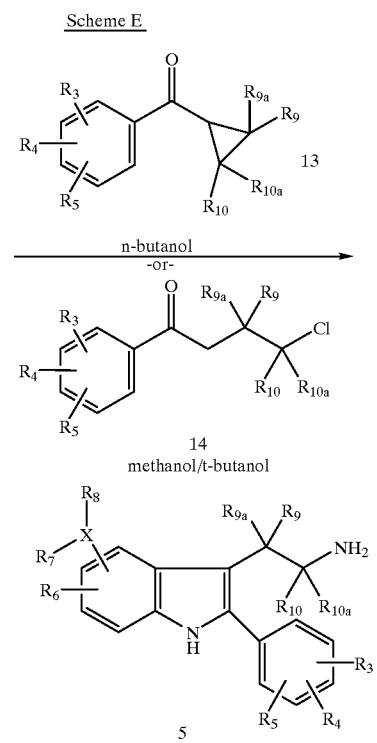

Reaction Scheme E

As shown in reaction Scheme E, treatment of an arylhydrazine or arylhydrazine hydrochloride (12) with an arylcyclopropylketone of type (13) in a polar organic solvent such as methanol, ethanol, n-propanol, isopropanol, n-butanol, t-butanol, preferably n-butanol, at a temperature of 70°–120° C. for a period of 8–24 hours gives 2-aryltryptamine (5). Alternatively, when an arylhydrazine or arylhydrazine hydrochloride (12) is treated with an arylbutyl ketone of type (14) containing a leaving group (chloride, bromide, iodide, O-methansulfonate, O-trifluoromethansulfonate, or the like) at the 4-position in a polar solvent such as methanol, ethanol, n-propanol, isopropanol, n-butanol, t-butanol, or mixtures thereof at room temperature for a period of 30 minutes to 2 hours followed by heating to a temperature of 65°–100° C. for 4–24 hours, 2-aryltryptamine (5) is produced.

Scheme F

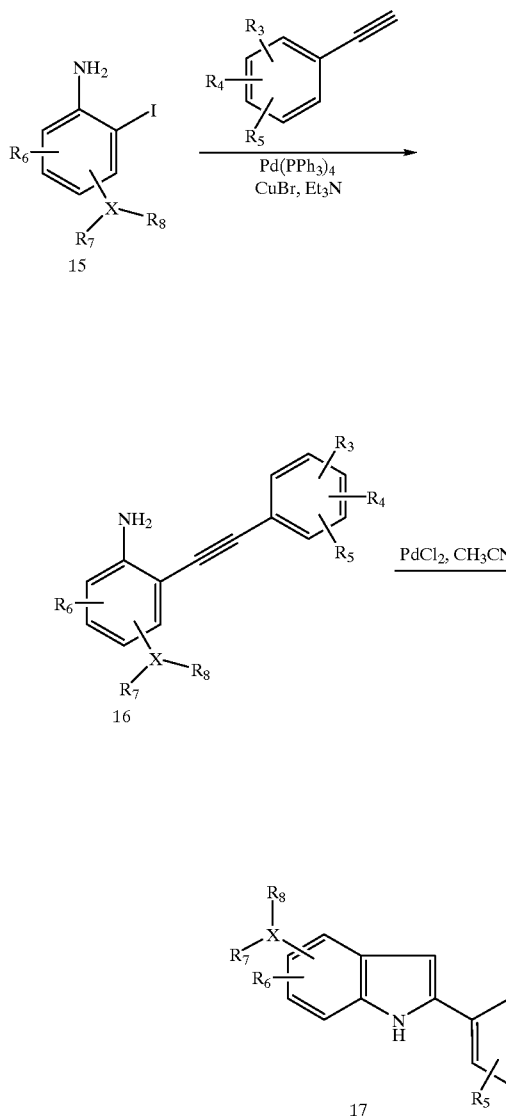

Reaction Scheme F

Scheme G

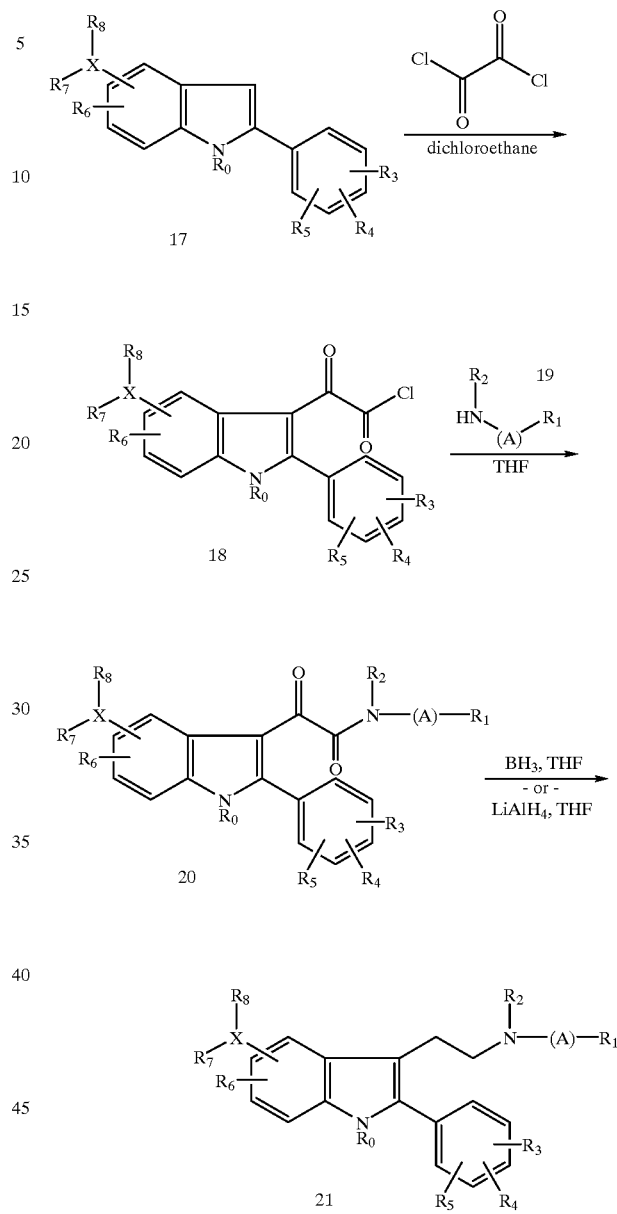

Reaction Scheme G

As shown in reaction Scheme F, iodoanilines of type (15) may be reacted with aryl acetylenes, an appropriate palladium (O) catalyst such as tetrakis(triphenylphosphine) palladium, a copper (I) halide such as cuprous bromide in an inert organic solvent such as triethylamine at a temperature of 50°–88° C. for a period of 30 minutes to 5 hours to provide the diarylacetylene (16). Acetylene (16) may be further modified by treatment with a palladium (II) catalyst such as palladium (II) chloride or palladium (II) acetate in an inert organic solvent such as acetonitrile at a temperature of 50°–82° C. for a period of 30 minutes to 6 hours to give 2-arylindole (17).

As shown in reaction Scheme G, treatment of 2-arylindole (17) with oxalyl chloride neat or in an inert organic solvent such as methylene chloride, chloroform, dichloroethane, tetrahydlrofuran or the like at a temperature of 25°–65° C. for a period of 3–24 hours gives the acylchloride adduct (18). The crude product (18) may be reacted with an amine of type (19) in an inert organic solvent such as diethylether, tetrahydrofuran, methylene chloride, chloroform or the like and an amine base such as triethylamine, diisopropylethylamine or pyridine at a temperature of 0° C.–25° C. for a period of 30 minutes to 4 hours to provide the amide derivative (20). Amide (20) may be further modified by treatment with a reducing agent such as borane or lithium aluminum hydride in an inert organic solvent such as tetrahydrofuran at elevated temperatures, preferably reflux, for a period of 1–5 hours to give compound (21).

Scheme H

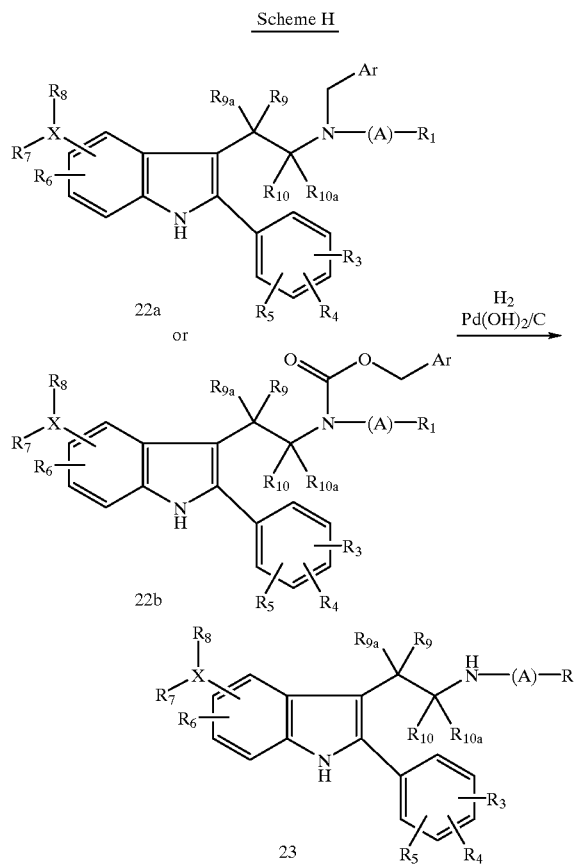

Reaction Scheme H

As shown in reaction Scheme H, N-benzyl derivatives of type (22a) or N-benzyloxycarbonyl derivatives of type (22b) may be reduced to provide the secondary amine analogs (7) by treatment with hydrogen (1 atm) and an appropriate catalyst such as palladium on carbon, palladium hydroxide on carbon, or the like in an inert organic solvent such as tetrahydrofuran, ethyl acetate, methanol, ethanol, or mixtures thereof to which has been added a weak acid such as 30% aqueous acetic acid for a period of 10 minutes to 3 hours or until the aryl group has been removed to give the secondary amine.

Scheme I

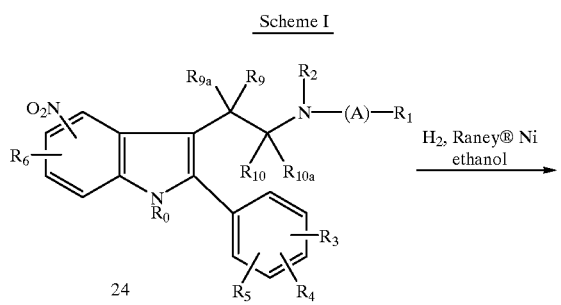

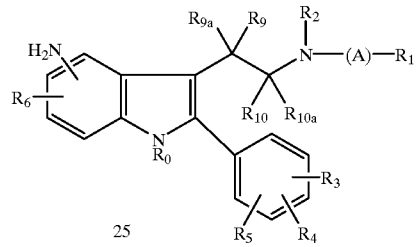

Reaction Scheme I

As shown in reaction Scheme I, treatment of a nitroindole of type (24) with hydrogen (1 atm) and an appropriate catalyst such as Raney® Nickel in an inert organic solvent such as ethanol, methanol, or the like at room temperature for a period of 2–12 hours gives the corresponding aminoindole derivative (25).

Scheme J

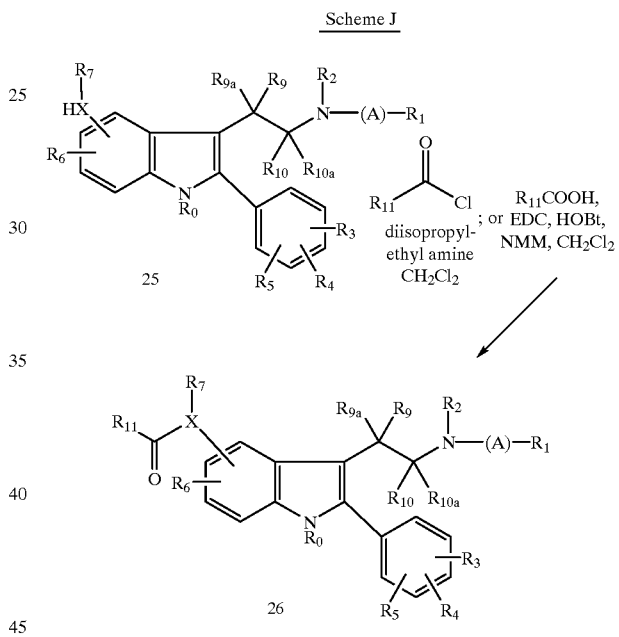

Reaction Scheme J

As shown in reaction Scheme J, amino- or hydroxyindole (25) may be modified by acylation under a variety of conditions. For example, treatment of (25) with an acid chloride, acid anhydride or active ester and an amine base such as triethylamine, diisopropylethylamine, pyridine, or the like in an inert organic solvent such as methylene chloride, chloroform, tetrahydrofuran, or mixtures thereof at 0° C. to room temperature for a period of 1 to 12 hours gives the corresponding amide or ester derivatives (26). Alternatively (25) may be coupled with a carboxylic acid by one of the many dehydrating agents commonly employed. For instance, treatment of aminoindole (25) with an appropriate carboxylic acid and 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide or ester derivative (26).

a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as methylene chloride, chloroform, or the like at a temperature of $-20°-0°$ C. for a period of 20 minutes to 2 hours. After this time, the reaction mixture is treated with an appropriate mono- or disubstituted amine at $-20°$ to $25°$ C. for a period of 1–5 hours to give the urea or carbamate analog (28).

Scheme K

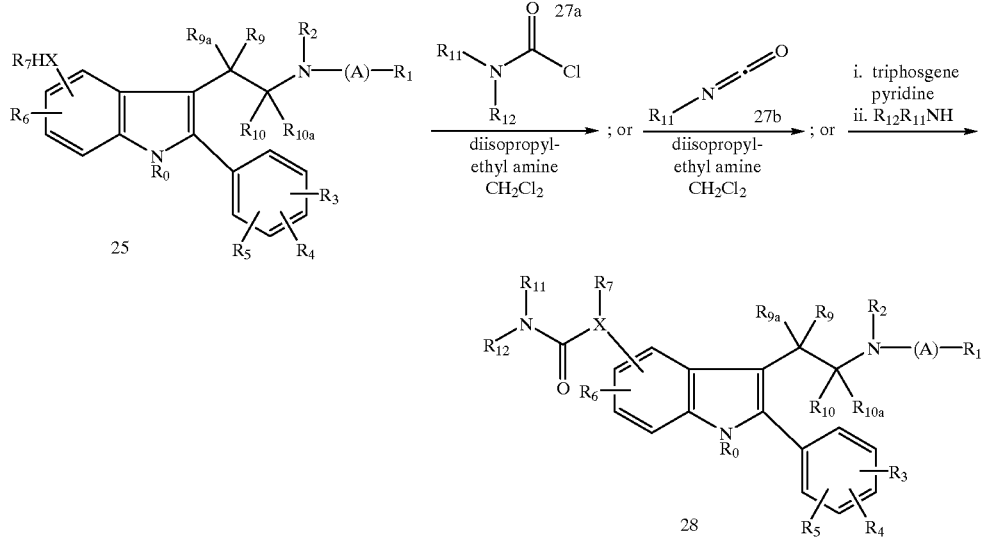

Reaction Scheme K

As shown in reaction Scheme K, urea or carbamate derivatives of (25) can be prepared by treatment with a carbamoyl chloride of type (27a), or alternatively with an isocyanate reagent of type (27b), and an amine base such as pyridine, triethylamine, diisopropylethylamine, N-methylmorpholine or the like in an inert organic solvent such as methylene chloride, chloroform, dimethylformamide, tetrahydrofuran or mixtures thereof at a temperature of $0°-65°$ C. for a period of 1–72 hours to give (28). Compound (25) can also be modified by treatment with

Scheme L

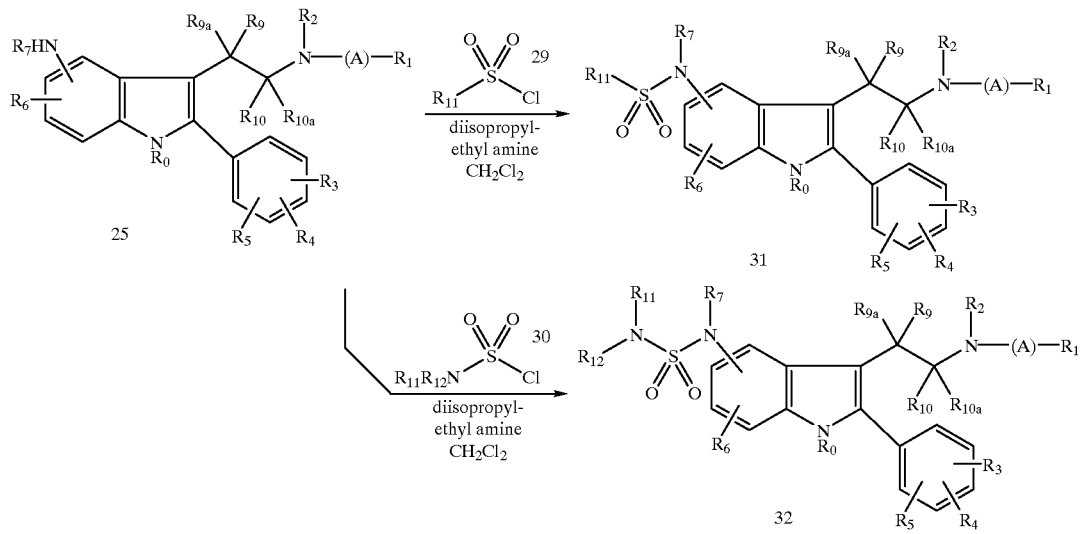

Reaction Scheme L

As shown in reaction Scheme L, amine (25) can be modified by treatment with an appropriate sulfonyl chloride of type (29) or sulfamyl chloride of type (30) with an amine base such as pyridine, triethylamine, diisopropylethylamine, N-methylmorpholine in an inert solvent such as methylene chloride, chloroform, dichloroethane or the like at a temperature of −20°–25° C. for a period of 20 minutes to 2 hours to give the corresponding N-sulfonamide (31) or N-sulfamylamide (32) derivatives, respectively.

Scheme M

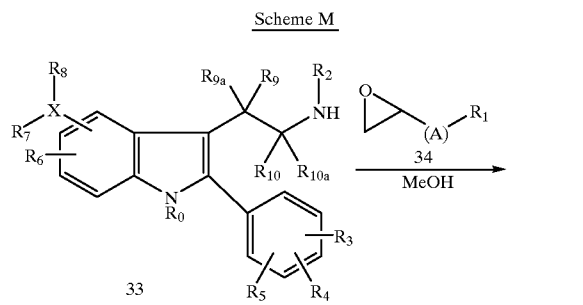

Reaction Scheme M

As shown in reaction Scheme M, the 2-aryltryptamine (33) can be modified by treatment with an epoxide such as (34) in an inert organic solvent such as methanol, ethanol, isopropanol, butanol, tert-butanol, or mixtures thereof at a temperature of 65°–110° C. for a period of 8–20 hours to give the corresponding amino-alcohol derivative (35).

Scheme N

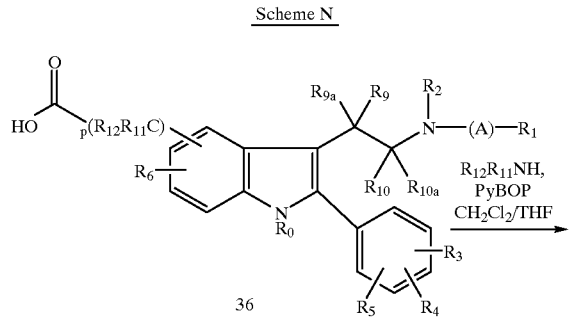

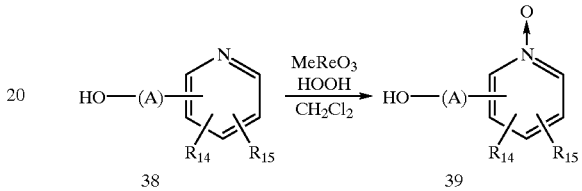

Scheme O

Reaction Scheme N

As shown in reaction Scheme N, amide derivatives of an acid-containing indole derivative such as (36) can be prepared by treatment with an appropriate amine ($R_{12}R_{11}$ NH) and a suitable coupling agent such as benzotriazol-1-yloxy-tris(pyrrolidino)phosphonium hexafluorophosphate (PyBOP), benzotriazol-1-yloxy-tris(dimethylamino) phosphonium hexafluorophosphate (BOP), 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, tetrahydrofuran, dimethylformamide, or mixtures thereof at or near room temperature for a period of 3–24 hours provides the corresponding amide derivative (37).

Scheme O

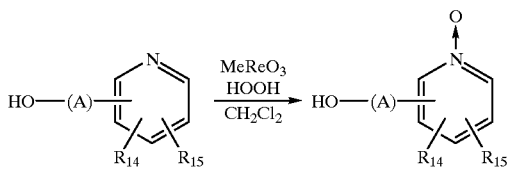

Reaction Scheme O

As shown in reaction Scheme O, pyridine derivatives such as (38) can be oxidized to the corresponding N-oxide by treatment with an oxidant such as 30% aqueous hydrogen peroxide and 0.5–5 mol % of a catalyst such as methyltrioxorhenium(VII) or the like in an inert organic solvent such as methylene chloride at or near room temperature for 1–3 days to provide (39).

Scheme P

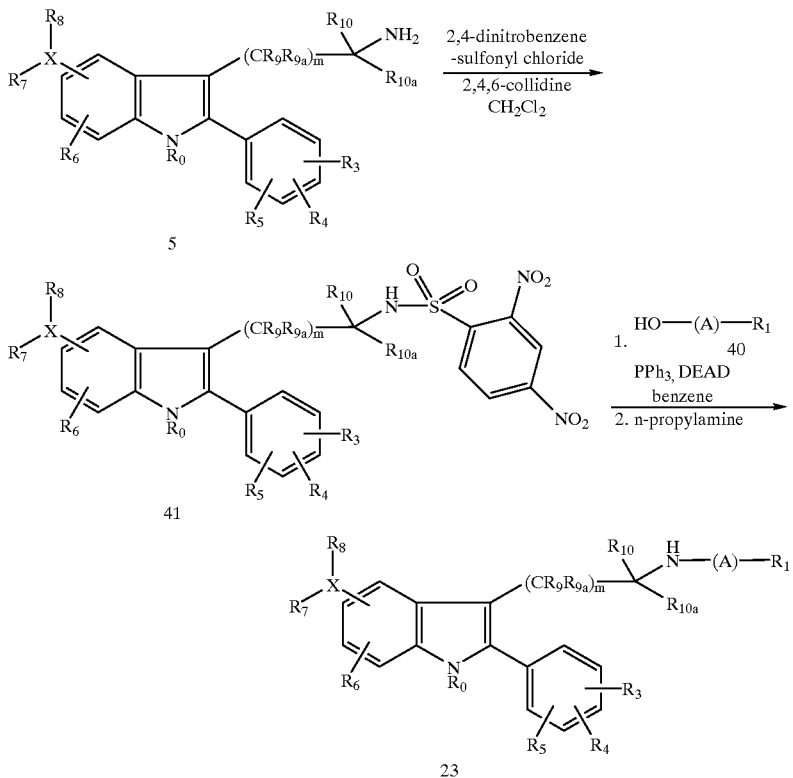

Reaction Scheme P

As shown in reaction Scheme P, the tryptamine 5 can be modified by reaction with an arylsufonyl chloride such as 2-nitrobenzenesulfonyl chloride, 4-nitrobenzenesulfonyl chloride or 2,4-dinitrobenzenesulfonyl chloride and a hindered amine base such as 2,4,6-collidine, 2,6-lutidine or the like in an inert organic solvent such as methylene chloride to provide the corresponding sulfonamide 41. Sulfonamides such as 41 can be further modified by reaction with an alcohol of type 40 in the presence of triphenylphosphine and an activating agent such as diethyl azodicarboxylate (DEAD), diisopropyl azodicaboxylate or the like in an inert organic solvent such as benzene, toluene, tetrahydrofuran or mixtures thereof to give the dialkyl-sulfonamide adduct. Removal of the sulfonyl group is accomplished by treatment with a nucleophilic amine such as n-propylamine or the like in an inert organic solvent such as methylene chloride to give secondary amines of type 23.

The compounds of the present invention are useful in the treatment of various sex-hormone related conditions in men and women. This utility is manifested in their ability to act as antagonists of the neuropeptide hormone GnRH as demonstrated by activity in the following in vitro assays.

Human GnRH Receptor Binding Assay

Crude membranes prepared from CHO cells expressing human GnRH receptors were the sources for GnRH receptor. [$^{125}$I]Buserelin (a peptidyl GnRH analog) was used as the radiolabelled ligand. The binding activity was determined as an $IC_{50}$ which is the antagonist concentration required to inhibit the specific binding of [$^{125}$I]buserelin to GnRH receptors by 50%.

Rat Pituitary GnRH Receptor Binding Assay:

Crude plasma membranes prepared from rat pituitary tissues were incubated in a Tris.HCl buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH Release Assay:

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-mL polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-mL disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of 3×10$^5$ cells/ml, and 1.0 ml of this suspension was placed in each well of a 24-well tray (Costar, Cambridge, Mass.). Cells were maintained in a humidified 5% $CO_2$-95% air atmosphere at 370° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1 ½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hyper-trophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. No. 3,239,345, U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methyl-propanamide;

2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methyl-propanamide;

3) N-[1(R)-[(1,2-Dihydro-1-benzenesulfonylspiro [3H-indole-3,4'-piperidin]-1'-yl)carbonyl]-2-(1H-indol-3-yl)ethyl]-2-amino-2-methyl-propanamide;

4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;

5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;

6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;

7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;

8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;

9) N-[1(R)-[(1,2-Dihydro-1-methanesulfonyl-5-fluorospiroy[3H-indole-3,4'-piperidin]-1'-yl)carbonyl]-2-(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl)carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methyl-propanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methyl-propanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl)methylsulfonylspiro-[3H-indole-3,4'-piperidin]-1'-yl)carbonyl]-2-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and *J. Org. Chem.*, 36, 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5a-reductase 2 inhibitor, such as finasteride or epristeride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoromethylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

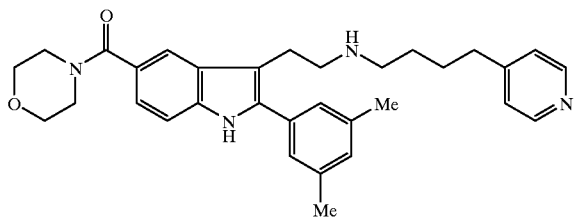

[2-(3,5-dimethylphenyl)-3-[2-(4-pyridin-4-ylbutylamino)ethyl]-1H-indol-5-yl]morpholin-4-ylmethanone Step 1A 3-(2-aminoethyl)-2-(3,5-dimethylphenyl)-1H-indole-5-carboxylic acid ethyl ester A mixture of 7.60 g (50 mmol) of 4-hydrazinobenzoic acid, 10.55 g (50 mmol) of 3-chloropropyl 3,5-dimethylphenyl ketone, and 200 mL of absolute ethanol was stirred under nitrogen and heated to reflux. After 12 hours, the mixture was cooled and filtered. The solid on the filter was washed with additional small volumes of ethanol. The filtrate was treated with 4 mL of concentrated sulfuric acid and stirred at reflux under nitrogen for 4 days. The cooled mixture was stirred in an ice bath as a solution of sodium ethoxide (21% w/w in ethanol) was added dropwise until the mixture was basic by pH paper. The mixture was filtered and concentrated in vacuo at 30° C. The residue was partitioned between diethyl ether and water, with some saturated aqueous sodium chloride solution added to assist in separation of the layers. The aqueous phase was washed with an additional 100 mL of ether. The combined organic extracts were dried over sodium sulfate, filtered, and concentrated in vacuo. The residual gum was purified by flash chromatograpy on silica gel (elution with 97:3:0.3 and then 95:5:0.5 methylene chloride:methanol:-ammonium hydroxide) to give the title compound (4.8g). 400 MHz $^1$H NMR (CDCl$_3$) was consistent with the assigned structure. Mass spectrum (PB-NH$_3$/CI): m/e=337 (M+H).

Step 1B 2-(3,5-dimethylphenyl)-3-[2-[4-(pyridin-4-yl)butylamino]-ethyl]-1H-indole-5-carboxylic acid ethyl ester To a dry flask were added 5.0 g (14.9 mmol) of 3-(2-aminoethyl)-2-(3,5-dimethylphenyl)-1H-indole-5-carboxylic acid ethyl ester, 1.98 g (13.5 mmol) of 4-(pyridin-4-yl)butyraldehyde (diluted with 0.5 mL of CDCl$_3$), 8.12 g (67.7 mmol) of anhydrous magnesium sulfate, and a magnetic stirring bar. The flask was purged with nitrogen, cooled to −10° C., and stirred as 11.5 mL of dry CDCl$_3$ was introduced gradually by syringe. The mixture was stirred under nitrogen for about 20 minutes. Next, the septum was removed, and 670 mg (17.6 mmol) of sodium borohyrdide was added rapidly. The septum was immediately replaced, and the system was again purged with nitrogen. The mixture was stirred under nitrogen at about −5° C. as 10 mL of dry methanol was added gradually by syringe. After a few minutes at this temperature, the reaction was removed from the cooling bath and partitioned between 80 mL of ethyl acetate and 100 mL of water. The organic layer was dried over sodium sulfate, filtered, and concentrated in vacuo. The residue was purified by flash chromatography on silica gel (elution with a gradient of 4–9% methanol in methylene chloride; repeated using 5–15% methanol in methylene chloride) to give the title compound (3.19 g). 500 MHz $^1$H NMR (CDCl$_3$) was consistent with the assigned structure. Mass spectrum (PB-NH$_3$/CI): m/e=470.4 (M+H). An additional 1.91 g of less pure material was also isolated.

Step 1C 3-[2-[benzyloxycarbonyl-[4-(pyridin-4-yl)butyl]amino]ethyl]-2-(3,5-dimethylphenyl)-1H-indole-5-carboxylic acid ethyl ester A solution of 3.19 g (6.83 mmol) of 2-(3,5-dimethylphenyl)-3-[2-[4-(pyridin-4-yl)butylamino]ethyl]-1H-indole-5-carboxylic acid ethyl ester in 25 mL of dry methylene chloride was stirred under nitrogen and cooled to −78° C. in a dry ice-acetone bath as 2.38 mL (1.76 g, 13.7 mmol) of N,N-diisopropylethylamine was added, followed by gradual addition of 3.4 mL (4.06 g; 23.7 mmol) of benzyl chloroformate by syringe, in portions. After about 2.5 hours, the solution was removed from the cooling bath and allowed to warm to room temperature. It was then partitioned between ethyl acetate and 5% aqueous potassium bisulfate solution. The organic phase was dried over magnesium sulfate, filtered, and concentrated in vacuo. Purification of the residue by flash chromatography on silica gel (elution with a gradient of 0.5–10% methanol in methylene chloride) afforded a quantitative yield of the product as a yellow foam. 500 MHz $^1$H NMR was complex, owing to the existence of rotamers, but was consistent with the assigned structure. Mass spectrum (PB-NH$_3$/CI): m/e=604.3 (M+H).

Step 1D 3-[2-[benzyloxycarbonyl-[4-(pyridin-4-yl)butyl]amino]-ethyl]-2-(3,5-dimethylphenyl)-1H-indole-5-carboxylic acid hydrochloride A solution of 4.11 g (6.83 mmol) of 3-[2-[benzyloxycarbonyl-[4-(pyridin-4-yl)butyl]amino]ethyl]-2-(3,5-dimethylphenyl)-1H-indole-5-carboxylic acid ethyl ester in 161 mL (80.5 mmol) of 0.50 N KOH in methanol was stirred at about 60° C. as 19 mL of water was added gradually. Stirring was continued at reflux overnight. The cooled mixture was concentrated in vacuo to give a yellow solid, which was partitioned between 250 mL of a 1:1 ethyl acetate-tetrahydrofuran mixture and 250 mL of 0.5 N HCl. The organic phase was washed twice with 0.5 N HCl, then dried over magnesium sulfate, filtered, and concentrated in vacuo. The resulting solid was triturated with diethyl ether and collected on a filter to give (after drying) 3.46 g of yellow solid, mp 133.5–137.5° C.; homogeneous by TLC (95:5:0.5 CH$_2$Cl$_2$-MeOH-AcOH). 500 MHz $^1$H NMR (DMSO-d$_6$) was consistent with the assigned structure. Mass spectrum (ESI): m/e=576.4 (M+H)$^+$.

Step 1E [2-[2-(3,5-dimethylphenyl)-5-(morpholine-4-carbonyl)-1H-indol-3-yl]ethyl]-(4-pyridin-4-ylbutyl)carbamic acid benzyl ester A mixture of 100 mg (0.163 mmol) of 3-[2-[benzyloxycarbonyl-[4-(pyridin-4-yl)butyl]amino]ethyl]-2-(3,5-dimethylphenyl)-1H-indole-5-carboxylic acid hydrochloride 101.7 mg (0.196 mmol) of PyBOP reagent, 0.085 mL (85.2 mg, 0.978 mmol) of morpholine, and 1 mL of dry methylene chloride was stirred under nitrogen at room temperature in a stoppered flask. After 5 days, the solution was partitioned between ethyl acetate and saturated aqueous sodium bicarbonate solution. The organic phase was dried over sodium sulfate, filtered, and concentrated in vacuo. Purification of the crude product by flash chromatography on silica gel (gradient elution with 1–4% MeOH in CH$_2$Cl$_2$) afforded a quantitative yield of the title compound as a yellow gum; homogeneous by TLC in 95:5 CH$_2$Cl$_2$-MeOH. 500 MHz $^1$H NMR (CDCl$_3$) was complex, owing to rotamers, but was consistent with the assigned structure. Mass spectrum (ESI): m/e=645.6 (M+H).

Step 1F [2-(3,5-dimethylphenyl)-3-[2-(4-pyridin-4-ylbutylamino)-ethyl]-1H-indol-5-yl]morpholin-4-ylmethanone A mixture of 113 mg (0.175 mmol) of [2-[2-(3,5-dimethylphenyl)-5-(morpholine-4-carbonyl)-1H-indol-3-yl]ethyl]-(4-pyridin-4-ylbutyl)carbamic acid benzyl ester, 50 mg of 20% palladium hydroxide on carbon, and 10 mL of 2-methoxyethanol was shaken with hydrogen (approx. 50 psig) in a pressure vessel for 2.5 hours. The catalyst was removed by filtration through Celite, and the filtrate was concentrated in vacuo. The residue was purified by flash chromatography on silica gel (gradient elution from 99:1:0.1 to 94:6:0.6 $CH_2Cl_2$-MeOH-concd. $NH_4OH$) yielded 53.2 mg (60%) of a white, stiff foam; homogeneous by TLC in 95:5:0.5 $CH_2Cl_2$-MeOH-concd. $NH_4OH$. 500 MHz $^1H$ NMR ($CDCl_3$) was consistent with the assigned structure. Mass spectrum (ESI): m/e=511.5 (M+H).

PREPARATION OF SYNTHETIC INTERMEDIATES

Step A: 4-(4-pyridyl)-3-pentyn-1-ol

4-Bromopyridine hydrochloride salt (5.5 g) was dissolved in a solvent mixture comprising triethylamine (50 mL) and water (10 mL). Anhydrous lithium chloride (100 mg), cooper (I) bromide powder (100 mg) and but-3-yn-1-ol (2.17g) was added to the pyridine salt and the mixture stirred as an active nitrogen gas stream passed gently through the solution for approximately 15 minutes after which time tetrakis(triphenylphosphine)palladium (250 mg) was added. The reaction mixture was heated to reflux under a nitrogen atmosphere and maintained at reflux for 2.5 h after which heating was stopped and the reaction allowed to cool to room temperature. The mixture was concentrated in vacuo and the residue treated with 3 M sodium hydroxide, extracted with chloroform and concentrated in vacuo. Purification of the residue by flash chromatography on silica gel (ethyl acetate) gave the title compound (3.74 g).

Step B: 4-(4-pyridyl)-butan-1-ol 4-(4-Pyridyl)-3-butyn-1-ol (3.5g) was dissolved in methanol (100 mL) in a Parr hydrogenation bottle and platinum (IV) oxide [Adams' Catalyst] (0.3g) was added. The Parr bottle was placed on a Parr hydrogenation apparatus and the solution hydrogenated at 40 psi for 2.5 h after which time the starting material had been judged to be consumed by TLC. The spent catalyst was removed by filtration through a Celite pad and the pad carefully washed with more methanol. The combined filtrates were evaporated under reduced pressure on a rotary evaporator and the oily residues then subjected to column chromatography on a short silica column using neat ethyl acetate as the eluant to provide the title compound (3.0 g).

Step C: 4-(pyridin-4-yl)butyraldehyde

Oxalyl chloride (1.45 mL of a 2M solution in dry methylene chloride) was placed in an oven-dried flask and cooled to −78° C. using a dry ice and acetone cooling bath and a solution of DMSO (0.413 mL) in dry methylene chloride (1 mL) added drop by drop to the oxalyl chloride over 3 minutes and stirred for a further 3 minutes. A solution of 4-(4-pyridyl)-butan-1-ol (400 mg) in dry methylene chloride (5 mL) was added to the reaction flask over approx. 3 minutes and the reaction stirred for 15 minutes. Anhydrous triethylamine (2.03 mL) was added and the reaction mixture stirred for another 2 hours during which time the cold bath had warmed up to room temperature. The reaction was quenched by the addition of saturated brine and then partitioned with methylene chloride. The aqueous layer was discarded and the methylene chloride extract dried over anhydrous sodium sulfate powder, filtered and evaporated under reduced pressure to leave an oily residue. The product was isolated by column chromatography on silica gel using ethyl acetate as eluant (301 mg).

EXAMPLE 2

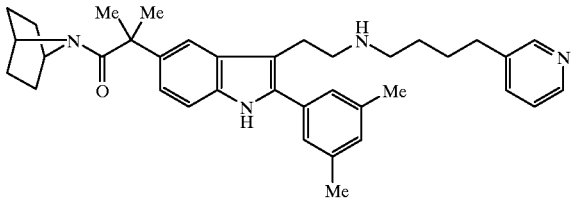

1-(7-azabicyclo[2.2.1]hept-7-yl)-2-[2-(3,5-dimethylphenyl)-3-[2-[4-(4-pyridin-3-yl)butylamino]ethyl]-1H-indol-5-yl]-2-methylpropan-1-one dihydrochloride Step 2A 2-[2-(3,5-dimethylphenyl)-3-[2-[4-(pyridin-3-yl)butylaminolethyl]-1H-indol-5-yl]-2-methylpropionic acid ethyl ester A dry flask containing 3.00 g (7.93 mmol) of 2-[3-(2-aminoethyl)-2-(3,5-dimethylphenyl)-1H-indol-5-yl]-2-methylpropionic acid ethyl ester (prepared essentially as described in EXAMPLE 1 from ethyl 2-(4-hydrazinophenyl)-2-methylpropionate), 4.76 g (39.7 mmol) of anhydrous magnesium sulfate, and a magnetic stirring bar was fitted with a septum and needle adapter leading to a Firestone valve. The flask was thoroughly purged with nitrogen, and the mixture was cooled in an ice-methanol bath at −10 to −5° C. and stirred vigorously as a solution of 1.32 g (8.88 mmol) of 4-(pyridin-3-yl)butyraldehyde in 15 mL of dry $CDCl_3$ was added gradually by syringe over 10–15 minutes. The resulting mixture was stirred under nitrogen at −10 to −5° C. for 40–45 minutes. Then the septum was removed just long enough to add 390 mg (10.3 mmol) of sodium borohydride. The mixture was stirred under nitrogen at −10 to −5° C. as 10 mL of dry methanol was added dropwise by syringe over several minutes. After 30 minutes, the mixture was removed from the cooling bath and partitioned between 90 mL of ethyl acetate and 90 mL of water. The organic layer was washed with 2 ¥ 30 mL of brine, then dried over anhydrous sodium sulfate. The filtered solution was concentrated in vacuo, and the residue was flash chromatographed of silica gel (gradient elution with 0–10% methanol in methylene chloride). Fractions containing product and a small amount of unreacted starting material were combined and concentrated to give 3.00 g of light beige, stiff foam, used directly in the next step without further purification or characterization.

Step 2B 2-[3-[2-[benzyloxycarbonyl-[4-(pyridin-3-yl)butyl]amino]ethyl]-2-(3,5-dimethylphenyl)-1H-indol-5-yl]-2-methylpropionic acid ethyl ester A solution of 3.00 g (max. 5.86 mmol) of crude 2-[2-(3,5-dimethylphenyl)-3-[2-[4-(pyridin-3-yl)butylamino]ethyl]-1H-indol-5-yl]-2-methylpropionic acid ethyl ester in 30 mL of dry methylene chloride was stirred under nitrogen with cooling in a dry-ice-acetone bath. To this solution was added by syringe 1.106 mL (820 mg, 6.36 mmol) of N,N-diisopropylethylamine. Then 0.956 mL (1.14 g, 6.36 mmol) of benzyl chloroformate was added dropwise by syringe over 5–10 minutes. After 20 minutes, the solution was removed from the cooling bath and allowed to warm to room temperature. After 2 hours, the solution was diluted with 50 mL of methylene chloride, transferred to a separatory funnel, and shaken with 80 mL of water. The organic phase was dried over magnesium sulfate, filtered, and concentrated in vacuo. Flash chromatography of the residual gum on silica gel (gradient elution with 0.2–2% methanol in methylene chloride gave 2.81 g (55% overall for Steps 1 and 2) of pale, golden-yellow gum; virtually homogeneous by TLC in 95:5 $CH_2Cl_2$-MeOH. 500 MHz $^1H$ NMR ($CDCl_3$) was complex, owing to rotamers, but appeared to be consistent with the assigned structure. Mass spectrum (ESI): m/e=646 (M+H).

Step 2C 2-[3-[2-[benzyloxycarbonyl-[4-(pyridin-3-yl)butyl]amino]ethyl]-2-(3,5-dimethylphenyl)-1H-indol-5-yl]-methylpropionic acid A mixture of 2.78 g (4.30 mmol) of 2-[3-[2-[benzyloxycarbonyl-[4-(pyridin-3-yl)butyl]amino]ethyl]-2-(3,5-dimethylphenyl)-1H-indol-5-yl]-2-methylpropionic acid ethyl ester in 43.0 mol (21.5 mmol) of 0.5 M potassium hydroxide in methanol and 25 mL of tetrahydrofuran was stirred under nitrogen and heated to reflux. To the resulting solution was gradually added 18 mL of water, and the solution was maintained at reflux for 39 hours. It was then cooled and concentrated to small volume, accompanied by precipitation. The mixture was treated with 10.75 mL (21.5 mmol) of 2 N hydrochloric acid and agitated for a few minutes. The solid was collected on a filter and washed thoroughly with water. After suction-drying under nitrogen, the solid was triturated and washed with diethyl ether and vacuum-dried to yield 2.43 g (92%) of cream-colored powder, mp 152–154° C. (partial dec.); homogeneous by TLC in 90:10 $CH_2Cl_2$-MeOH. 500 MHz $^1H$ NMR (DMSO-$d_6$) was consistent with the assigned structure. Mass spectrum (ESI): m/e=618 (M+H).

Step 2D [2-[5-[2-(7-azabicyclo[2.2.1]hept-7-yl)-1,1-dimethyl-2-oxoethyl]-2-(3,5-dimethylphenyl)-1H-indol-3-yl]ethyl]-[4-(pyridin-3yl)butyl]carbamic acid benzyl ester A mixture of of 92.7 mg (0.15 mmol) of 2-[3-[2-[benzyloxycarbonyl-[4-(pyridin-3-yl)butyl]amino]ethyl]-2-(3,5-dimethylphenyl)-1H-indol-5-yl]-2-methylpropionic acid, 80.2 mg (0.6 mmol) of 7-azabicyclo[2.2.1]heptane hydrochloride, 83.2 mg (0.16 mmol) of PyBOP reagent, 0.107 mL (77.8 mg; 0.77 mmol) of triethylamine, and 0.75 mL of dry methylene chloride was stirred at room temperature in a stoppered flask for 48 hours. The solution was then partitioned between 10 mL of ethyl acetate and 10 mL of 0.5 N hydrochloric acid. The organic phase was washed with 10 mL of saturated aqueous sodium bicarbonate solution and then with 5 mL of saturated aqueous sodium chloride solution. The ethyl acetate phase was then dried (magnesium sulfate), filtered, and concentrated in vacuo at room temperature. The residue was purified by preparative TLC on 6 Analtech tapered silica gel plates (20×20 cm), which were developed in 95:5 $CH_2Cl_2$-MeOH. The product band from each plate was isolated, combined, and extracted with 95:5 $CH_2Cl_2$-MeOH. Concentration of the extracts in vacuo yielded 85.9 mg (82%) of a very pale yellow glass; virtually homogeneous by TLC in 95:5 $CH_2Cl_2$-MeOH. 506 MHz $^1H$ NMR ($CDCl_3$) was complex, owing to rotamers, but was consistent with the assigned structure. Mass spectrum (ESI): m/e=697.6 (M+H).

Step 2E 1-(7-azabicyclo[2.2.1]hept-7-yl)-2-[2-(3,5-dimethylphenyl)-3-[2-[4-(pyridin-3-yl)butylamino]ethyl]-1H-indol-5-yl]-2-methylpropan-1-one A mixture of 80.2 mg (0.115 mmol) of [2-[5-[2-(7-azabicyclo[2.2.1]hept-7-yl)-1,1-dimethyl-2-oxoethyl]-2-(3,5-dimethylphenyl)-1H-indol-3-yl]ethyl]-[4-(pyridin-3yl)butyl]carbamic acid benzyl ester, 40 mg of 10% palladium on carbon, 4 mL of absolute ethanol, and 4 mL of ethyl acetate was shaken with hydrogen (46 psig) in a pressure vessel for 6 hours. The catalyst was removed by filtration through Celite under nitrogen, and the filtrate was concentrated in vacuo at room temperature. The residue was purified by preparative TLC on 4 Analtech tapered silica gel plates (20×20 cm), which were developed in 92.5:7.5:0.75 $CH_2Cl_2$-MeOH-concentrated $NH_4OH$. The product band from each plate was isolated, combined, and extracted with 92.5:7.5:0.75 $CH_2C_{12}$-MeOH-concentrated $NH_4OH$. Concentration of the extracts in vacuo yielded 53.8 mg (81%) of a pale yellow, stiff gum or glass; essentially homogeneous by TLC in 92.5:7.5:0.75 $CH_2Cl_2$-MeOH-concentrated MeOH-concentrated $NH_4OH$. 500 MHz $^1H$ NMR ($CDCl_3$) was consistent with the assigned structure. Mass spectrum (ESI): m/e=563.5 (M+H).

Step 2F 1-(7-azabicyclo[2.2.1]hept-7-yl)-2-[2-(3,5-dimethylphenyl)-3-[2-[4-(pyridin-3-yl)butylamino]ethyl]-1H-indol-5-yl]-2-methylpropan-1-one dihydrochloride A solution of 42.8 mg (0.0760 mmol) of 1-(7-azabicyclo[2.2.1]hept-7-yl)-2-[2-(3,5-dimethylphenyl)-3-[2-[4-(pyridin-3-yl)butylamino]ethyl]-1H-indol-5-yl]-2-methylpropan-1-one in 1.5 mL of methanol was treated with 0.152 mL (0.304 mmol) of 2 N hydrochloric acid. The solution was agitated and allowed to stand briefly before being filtered. The filtrate was evaporated to dryness under nitrogen, and the residue was triturated with diethyl ether. The resulting solid was collected on a filter, washed with additional ether, and dried to yield 46.5 mg (96%) of light golden-tan powder, mp>160° C. (gradual; preliminary softening). 500 MHz $^1H$ NMR (DMSO-$d_6$) was consistent with the assigned structure.

PREPARATION OF SYNTHETIC INTERMEDIATES

Step A: Ethyl (+/−)-2-(4-nitrophenyl)propionate

To a solution of 9.76 g (50 mmol) of (+/−)-2-(4-nitrophenyl)propionic acid in 150 mL of absolute ethanol was added 3.0 mL of concentrated sulfuric acid. The resulting solution was stirred at reflux under nitrogen. After 6 hours, the solution was cooled and stirred vigorously as 250 mL of saturated aqueous sodium bicarbonate solution was added gradually (Caution: foaming). The mixture was then partitioned between 750 mL of ethyl acetate and 500 mL of water. The organic layer was washed with 100 mL of saturated aqueous sodium bicarbonate solution and then with 100 mL of saturated aqueous sodium chloride solution. The organic phase was dried over magnesium sulfate, filtered, and concentrated in vacuo to give 10.86 g (97%) of an oil; homogeneous by TLC in 9:1 hexane-ethyl acetate. 400 MHz $^1H$ NMR ($CDCl_3$) was consistent with the assigned structure.

Step B: Ethyl 2-methyl-2-(4-nitrophenyl)propionate

A suspension of 924 (23 mmol) of sodium hydride (60% in oil) in 21 mL of dry N,N-dimethylformamide was stirred under nitrogen in an ice bath as a solution of 4.68 g (21 mmol) of ethyl (+/−)-2-(4-nitrophenyl)propionate in 20.5 mL of dry N,N-dimethylformamide was added gradually over about 10 minutes. An intense violet color developed during the addition. The mixture was then allowed to warm to room temperature. After about 1 hour, the mixture was again cooled in an ice bath as a solution of 1.44 mL (3.28 g; 23 mmol) of methyl iodide in 5 mL of dry N,N-dimethylformamide was added dropwise by syringe over about 10 minutes, while maintaining the internal temperature at 10–15° C. The mixture was allowed to warm to room temperature, and the color changed to brown. After 1 hour, an additional 187 mL (426 mg, 3 mmol) of iodomethane was added. By the next day, the mixture consisted of a suspension of some grayish solid in a golden liquid. It was stirred vigorously and quenched by gradual addition of 10 mL of 5% aqueous potassium bisulfate solution. The mixture was partitioned between 400 mL of diethyl ether and 400 mL of water. The organic layer was washed with an additonal 3×400 mL of water and then with 50 mL of saturated aqueous sodium chloride solution. The organic phase was then dried over magnesium sulfate, filtered, and concentrated in vacuo. Flash chromatography of the residue on silica gel (elution with 19:1 hexane-ethyl acetete) yielded 4.31 g (87%) of an oil; homogeneous by TLC in 9:1 hexane-ethyl acetete. 400 MHz $^1$H NMR (CDCl$_3$) was consistent with the assigned structure.

Step C: Ethyl 2-(4-Aminophenyl)-2-methylpropionate

A mixture of 4.27 g (18 mmol) of ethyl 2-methyl-2-(4-nitrophenyl)propionate, 200 mg of 10% palladium on carbon, and 120 mL of absolute ethanol was shaken with hydrogen (initial hydrogen pressure 47 psig) in a pressure vessel for 2 hours. The catalyst was removed by filtration through Celite under nitrogen, and the filter cake was washed with additional ethanol. Concentration of the filtrate in vacuo at up to 50° C. gave 3.74 g (100%) of an oil; homogeneous by TLC in 4:1 hexane-EtOAc. 400 MHz $^1$H NMR (CDCl$_3$) was consistent with the assigned structure. Mass spectrum (ESI): m/e=208 (M+H).

Step D: Ethyl 2-(4-hydrazinophenyl)-2-methylpropionate

A solution of 3.725 g (18 mmol) of ethyl 2-(4-aminophenyl)-2-methylpropionate in 18 mL of concentrated hydrochloric acid was stirred at −10 to −5° C. in an ice-acetone bath as a solution of 1.29 g (18.7 mmol) of sodium nitrite in 7.5 mL of water was added dropwise over about 15 minutes. Stirring was continued at this temperature for an additional 30 minutes. Next, a small amount of insoluble solid was removed by filtration into a cold receiving flask. The filtrate was then added dropwise over 10–15 minutes to a solution of 20.3 g (90 mmol) of stannous chloride dihydrate in 14.5 mL of concentrated hydrochloric acid stirred under nitrogen in an ice-acetone bath. The addition was carried out at such a rate that the internal temperature remained at about −5° C. A gummy material separated during the addition. After completion of the addition, stirring was continued at −10 to −5° C. for 1 hour. The aqueous phase was decanted, and the residual gum was dissolved in 250 mL of ethyl acetate. The ethyl acetate solution was treated cautiously with 250 mL of saturated aqueous sodium bicarbonate solution and shaken in a separatory funnel. The ethyl acetate layer was washed with 50 mL of saturated aqueous sodium chloride solution. The entire mixture was filtered before separation of the phases. The ethyl acetate phase was dried over magnesium sulfate, filtered, and concentrated in vacuo at room temperature to yield 2.59 g (65%) of an oil. 500 MHz $^1$H NMR (CDCl$_3$) was consistent with the assigned structure and indicated that only minor impurities were present.

EXAMPLE 3.1

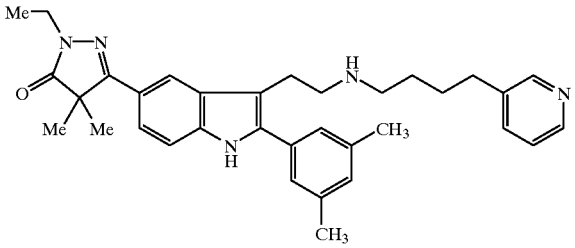

5-[2-(3,5-dimethylphenyl)-3-[2-[4-(pyridin-3-yl) butylamino]ethyl-1H-indol-5-yl]-2-ethyl-4,4-dimethyl-2,4-dihydropyrazol-3-one Step 3.1A 2-ethyl-4,4-dimethyl-5-(4-nitrophenyl)-2,4-dihydropyrazol-3-one A mixture of 1.00 g (4 mmol) of 2,2-dimethyl-3-(4-nitrophenyl)-3-oxopropionic acid methyl ester (Yang, C.-Y.; Wnek, G. E., Polymer, 1992, 33, 4191–4196), 3.00 g (20 mmol) of ethylhydrazine oxalate, 8 mL of 2-methoxyethanol, and 4 mL of glacial acetic acid was stirred under nitrogen at gentle reflux for 24 hours. The cooled solution was concentrated in vacuo. The residue was partitioned between ethyl acetate and water. The ethyl acetate phase was washed with additional water and then with saturated aqueous sodium chloride solution. The organic solution was dried over magnesium sulfate, filtered, and concentrated in vacuo to give 703 mg (67%) of light yellow crystals, mp 121–122° C.; homogeneous by TLC in 2:1 hexane-EtOAc. 500 MHz $^1$H NMR (CDCl$_3$) was consistent with the assigned structure. Mass spectrum (PB-NH$_3$/CI): m/e=232.1 (M−Et), 265.1 (M+H).

Step 3.1B 5-(4-aminophenyl)-2-ethyl-4.4-dimethyl-2,4-dihydro-pyrazol-3-one

Hydrogenation of 2-ethyl-4,4-dimethyl-5-(4-nitrophenyl)-2,4-dihydropyrazol-3-one according to the procedure of Example 3.2 Step E afforded a quantitative yield of light yellow-tan solid, mp 118–120.5° C.; homogeneous by TLC in 1:1 hexane-EtOAc and 98:2 CH$_2$Cl$_2$-MeOH. 500 MHz $^1$H NMR (CDCl$_3$) was consistent with the assigned structure. Mass spectrum (ESI): m/e=232.1 (M+H).

Step 3.1C 2-ethyi-5-(4-hydrazinophenyl)-4,4-dimethyl-2,4-dihydropyrazol-3-one

This material was prepared from 5-(4-aminophenyl)-2-ethyl-4,4-dimethyl-2,4-dihydropyrazol-3-one according to the procedure of Example 2 REACTION INTERMEDIATES, Step D, except that the entire reaction mixture from the stannous chloride reduction was stirred in an ice bath and treated cautiously with excess saturated sodium carbonate solution (CAUTION: foaming), resulting in precipitation. This material was transferred to a separatory funnel and shaken with 2:1 Et$_2$O—CH$_2$Cl$_2$. The mixture was filtered before separation of the phases. The aqueous phase was extracted further with several portions of ethyl acetate. The combined organic fractions were concentrated in vacuo to give an 80% yield of an amorphous, light yellow-orange solid, mp 131.5–135° C. dec; ill-defined by TLC in 95:5 CH$_2$Cl$_2$-MeOH. 500 MHz $^1$H NMR (CDCl$_3$) was consistent with the assigned structure.

Step 3.1D 5-[3-(2-aminoethyl)-2-(3,5-dimethylphenyl)-1H-indol-5-yl]-2-ethyl-4,4-dimethyl-2,4-dihydropyrazol-3-one This compound was prepared from 2-ethyl-5-(4-hydrazinophenyl)-4,4-dimethyl-2,4-dihydropyrazol-3-one and 3-chloropropyl 3,5-dimethylphenyl ketone according to the procedure of Example 3.2 Step A, except that the reaction time was 15 hours. Flash chromatography of the crude product on silica gel (gradient elution with 97:3 and 95:5 CH$_2$Cl$_2$-MeOH followed by 95:5:0.5 and 92.5:7.5:0.75 CH$_2$Cl$_2$-MeOH-concd. NH$_4$OH) gave a 27% yield of light tan, stiff foam; homogeneous by TLC in 92.5:7.5:0.75 CH$_2$Cl$_2$-MeOH-concd. NH$_4$OH. 500 MHz $^1$H NMR (CDCl$_3$) was consistent with the assigned structure. Mass spectrum (PB-NH$_3$/CI): m/e=403.2 (M+H).

Step 3.1E 5-[2-(3,5-dimethylphenyl)-3-[2-[4-(pyridin-3-yl) butylamino]ethyl-1H-indol-5-yl]-2-ethyl-4,4-dimethyl-2,4-dihydropyrazol-3-one A mixture of 82.5 mg (0.205 mmol) 5-[3-(2-aminoethyl)-2-(3,5-dimethylphenyl)-1H-indol-5-yl]-2-ethyl-4,4-dimethyl-2,4-dihydropyrazol-3-one and 124 mg (0.475 mmol) of magnesium sulfate was purged with nitrogen and stirred in an ice-methanol bath at about −10 to −5° C. as a solution of 34.3 mg (0.23 mmol) of 4-(pyridin-4-yl) butyraldehyde in 0.500 mL of dry CDCl$_3$ was added gradually by syringe. The mixture was stirred under nitrogen at this temperature for 30 minutes. The septum was removed just long enough to add 10.0 mg (0.265 mmol) of sodium borohydride, and the solution was repurged with nitrogen. The mixture was stirred at −10 to −5° C. as 350 mL of dry methanol was added gradually, and stirring was continued at this temperature. After 45 minutes, the mixture was partitioned between ethyl acetate and water. The ethyl acetate layer was washed with brine, then dried over sodium sulfate, filtered, and concentrated in vacuo. The residue was purified by preparative TLC on 6 1000-micron silica gel GF plates (developed in 87.5:12.5 CH$_2$Cl$_2$-MeOH). Isolation of the product band (by extraction with 90:10:1 CH$_2$Cl$_2$-MeOH-concd. NH$_4$OH) gave 49.8 mg (45%) of a light beige, stiff foam; essentially homogeneous by TLC in 90:10 CH$_2$Cl$_2$-MeOH. 500 MHz $^1$H NMR (CDCl$_3$) was consistent with the assigned structure. Mass spectrum (ESI): m/e=536.4 (M+H).

EXAMPLE 3.2

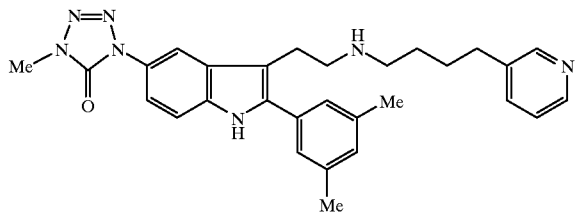

1-{2-(3,5-dimethylphenyl)-3-[2-(4-pyridin-3-yl-butylamino)ethyl]-1H-indol-5-yl}4-methyl-1,4-dihydrotetrazol-5-one Step 3.2A 2-[2-(3,5-dimethylphenyl)-5-nitro-1H-indol-3-yl] ethylamine To a solution of 3-chloropropyl 3,5-dimethylphenyl ketone (2.5 g in 13.5 mL tert-butanol) was added 1.65 g 4-nitrophenylhydrazine and stirred for 20 minutes at room temperature. At this time, 108 mL of 90% aqueous methanol was added and the mixture heated to reflux on an oil bath. After 16 hours, the mixture was cooled to room temperature and the volatiles removed in vacuo. The residue was triturated with ethyl acetate and allowed to stand at 0° C. for 8 hours. Filtration of the resulting suspension gave the crude title compound as the hydrochloride salt (1.4 g).

Step 3.2B N-{2-[2-(3,5-dimethylphenyl)-5-nitro-1H-indol-3-yl]ethyl}benzamide

To a solution of 2-[2-(3,5-dimethylphenyl)-5-nitro-1H-indol-3-yl]ethylamine (3.0 g in 80 mL dry methylene chloride) at 0° C. was added 4.0 mL triethylamine followed by 1.4 mL benzoyl chloride and the mixture stirred at low temperature. After 20 minutes, the reaction was quenched by the addition of saturated aqueous sodium bicarbonate and extracted with ethyl acetate. The organic portion was washed with water and concentrated in vacuo to give the crude title compound (1.43 g).

Step 3.2C. Benzyl-{2-[2-(3,5-dimethylphenyl)-5-nitro-1H-indol-3-yl]ethyl}amine

To a stirred solution of N-{2-[2-(3,5-dimethylphenyl)-5-nitro-1H-indol-3-yl]ethyl}benzamide (1.7 g in 130 mL dry tetrahydrofuran) was added 35 mL of a 1M solution of borane in tetrahydrofuran and the mixture heated slowly to reflux on an oil bath. After 2 hours the mixture was cooled to room temperature and the excess borane quenched by the careful addition of methanol. The mixture was concentrated to half-volume, treated with N,N-dimethylethanolamine (13 mL) and heated to reflux on an oil bath. After 3 hours the mixture was cooled to room temperature and concentrated in vacuo. Purification by flash chromatography on silica gel (methylene chloride:methanol, 97:3) gave the title compound (1.5 g).

Step 3.2D Benzyl-{2-[2-(3,5-dimethylphenyl)-5-nitro-1H-indol-3-yl]ethyl}-(4-pyridin-3-yl-butyl)amine A mixture of benzyl-{2-[2-(3,5-dimethylphenyl)-5-nitro-1H-indol-3-yl]ethyl}amine (700 mg) and 4-pyridin-3-yl butyraldehyde (314 mg) were solvated in 30 mL dry methanol to which ca. 2 g powdered 3 Å molecular sieves were added. The pH of this mixture was adjusted to 5 by the addition of trifluoroacetic acid and then 441 mg sodium cyanoborohydride was added and the mixture atirred at room temperature. After 48 hours, the mixture was filtered through diatomaceous earth, concentrated in vacuo and purified by flash chromatography on silica gel (methylene chloride:methanol:ammonium hydroxide, 96:4:0; then 96:4:1) to give the title compound (676 mg).

Step 3.2E 3-{2-[benzyl-(4-pyridin-3-yl-butyl)amino]ethyl}-2-(3,5-dimethylphenyl)-1H-indol-5-ylamine To a stirred solution of benzyl-{2-[2-(3,5-dimethylphenyl)-5-nitro-1H-indol-3-yl]ethyl}-(4-pyridin-3-yl-butyl)amine (350 mg in 30 mL absolute ethanol) was added ca. 30 mg of Raney" nickel. The reaction flask was fitted with a hydrogen balloon, evacuated and recharged with hydrogen (3 times) and stirred at room temperature. After 3 hours the reaction was flushed with nitrogen, filtered over diatomaceous earth and concentrated in vacuo. Purification by flash chromatography on silica gel (methylene chloride:methanol:ammonium hydroxide, 96:4:1) gave the title compound (246 mg).

Step 3.2F Benzyl-{2-[2-(3,5-dimethylphenyl)-5-isocvanato-1H-indol-3-yl]ethyl}-(4-pyridin-3-yl-butyl)amine To a solution of 3-{2-[benzyl-(4-pyridin-3-yl-butyl) amino]ethyl}-2-(3,5-dimethylphenyl)-1H-indol-5-ylamine (120 mg in 8 mL dry methylene chloride) at 0° C. was added 26.6 mg triphosgene followed by 0.050 mL pyridine and the mixture stirred at low temperature. After 50 minutes, the mixture was concentrated in vacuo to give the crude title compound (120 mg).

Step 3.2G 1-[3-{2-[benzyl-(4-pyridin-3-yl-butyl)-amino] ethyl}-2-(3,5-dimethylphenyl)-1H-indol-5-yl]-1,4-dihydrotetrazol-5-one To a solution of freshly prepared aluminum azide (0.6 mmol in 6 mL dry tetrahydrofuran) was added 120 mg benzyl-{2-[2-(3,5-dimethylphenyl)-5-isocyanato-1H-indol-3-yl]ethyl}-(4-pyridin-3-yl-butyl)amine and the mixture heated to reflux on an oil bath. After 20 hours, the mixture was cooled to room temperature concentrated poured into a mixture of 1M sodium potassium tartarate and ice, stirred vigorously for 40 minutes then partitioned between ethyl acetate and water. The organic portion was washed successively with 1M sodium potassium tartarate, water and brine then dried over sodium sulfate. Purification of the concentrate by flash chromatography on silica gel (methylene chloride:methanol, 88:12) gave the title compound (58 mg).

Step 3.2H 1-[3-{2-[benzyl-(4-pyridin-3-yl-butyl)amino]ethyl}-2-(3,5-dimethylphenyl)-1H-indol-5-yl]-4-methyl-1,4-dihydrotetrazol-5-one To a solution of 1-[3-{2-[benzyl-(4-pyridin-3-yl-butyl)-amino]ethyl}-2-(3,5-dimethylphenyl)-1H-indol-5-yl]-1,4-dihydrotetrazol-5-one (25 mg in 1.5 mL dry N,N-dimethylformamide) at 0° C. was added 13 mg potassium carbonate followed by 0.033 mL of a 10% solution of iodomethane in methylene cloride, and the mixture stirred at low temperature. After 2 hours, the reaction was quenched by the addition of saturated aqueous ammonium chloride and the mixture extracted with ethyl acetate. The organic portion was washed successively with water and brine, dried over sodium sulfate and concentrated in vacuo. Purification of the concentrate by flash chromatography on silica gel (methylene chloride:methanol, 95:5) gave the title compound (20 mg).

Step 3.2I 1-{2-(3,5-dimethylphenyl)-3-[2-(4-pyridin-3-yl-butylamino)ethyl]-1H-indol-5-yl}4-methyl-1,4-dihydrotetrazol-5-one To a stirred solution of 1-[3-{2-[benzyl-(4-pyridin-3-yl-butyl)amino]ethyl}-2-(3,5-dimethylphenyl)-1H-indol-5-yl]-4-methyl-1,4-dihydrotetrazol-5-one (20 mg in 4 mL methanol) was added 15 mg of 10% palladium hydroxide on carbon catalyst followed by acetic acid (0.020 mL of a 30% solution in water). The reaction flask was fitted with a hydrogen balloon, evacuated and recharged with hydrogen (3 times) and stirred at room temperature. After 30 minutes the reaction was flushed with nitrogen, filtered over diatomaceous earth and concentrated in vacuo. Purification by flash chromatography (methylene chloride:methanol:ammonium hydroxide, 90:6.5:1) gave the title compound (16 mg). m/e=496 (M+H)

PREPARATION OF SYNTHETIC INTERMEDIATES

Step A: 4-chloro-N-methoxy-N-methylbutyramide

To a solution of 4-chlorobutyryl chloride (10.0 g in 200 mL of dry methylene chloride) was added 10.4 g of N,O-dimethylhydroxylamine hydrochloride. The mixture was stirred under nitrogen and maintained below 25° C. by cooling in an ice bath as necessary while triethylamine (29.1 mL) was added dropwise over about 20 minutes, resulting in precipitation. After 1.5 hours at room temperature, the mixture was concentrated in vacuo. The residue was partitioned between 100 mL of diethyl ether and 100 mL of saturated aqueous sodium bicarbonate solution. The organic layer was washed with an additional 100 mL of saturated sodium bicarbonate, and the aqueous fractions were back-extracted with ether. The combined organic phases were dried over sodium sulfate, filtered, and concentrated in vacuo to give 10.5 g (90%) of an oil, which had satisfactory purity by $^1$H NMR (CDCl$_3$). Mass spectrum (PB-NH$_3$/CI): m/e=166 (M+H).

Step B: 3-chloropropyl 3,5-dimethylphenyl ketone

A solution of 10.2 mL (13.9 g; 72 mmol) 5-bromo-m-xylene in 200 mL of anhydrous tetrahydrofuran was stirred under nitrogen at −78° C. as 35.8 mL (84 mmol) of 2.5 M n-butyllithium in tetrahydrofuran was added dropwise. After 15 minutes at −78° C., a solution of 10.0 g (60 mmol) of 4-chloro-N-methoxy-N-methylbutyramide in 30 mL of anhydrous tetrahydrofuran was added dropwise over 25–30 minutes. The resulting solution was maintained at −78° C. for 45 minutes and then warmed briefly to room temperature. The reaction was quenched by addition of 40 mL of 2 N hydrochloric acid and then partitioned between ethyl acetate and water. The organic phase was washed with saturated aqueous sodium bicarbonate solution and then saturated aqueous sodium chloride solution. The organic solution was dried over sodium sulfate, filtered, and concentrated in vacuo. Flash chromatography of the residue afforded 8.91 g (70%) of an oil, which had satisfactory purity by $^1$H NMR (CDCl$_3$).

EXAMPLE 3.3

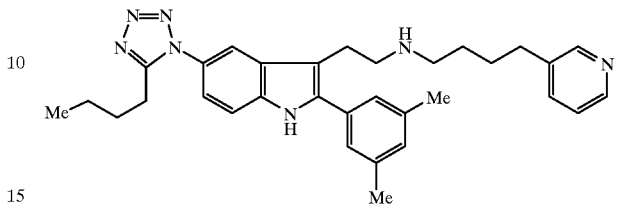

{2-[5-(2-butylpentazol-1-yl)-2-(3,5-dimethylphenyl)-1H-indol-3-yl]ethyl}-(4-pyridin-3-yl-butyl)amine Step 3.3A Benzyl-{2-[2-(3,5-dimethylphenyl)-5-nitro-1H-indol-3-yl]ethyl}carbamic acid tert-butyl ester To a solution of benzyl-{2-[2-(3,5-dimethylphenyl)-5-nitro-1H-indol-3-yl]ethyl}amine (EXAMPLE 3.2 StepC, 450 mg in 10 mL tetrahydrofuran and 3 mL water) at 0° C. was added a solution of 491 mg di-tert-butyl dicarbonate followed by 236 mg poatssium carbonate and the resulting suspension stirred vigourously at 0° C. After 50 minutes, the reaction was quenched by the addition of excess saturated aqueous ammonium chloride and the mixture extracted with ethyl acetate. The organic portion was dried over sodium sulfate and concentrated in vacuo. The residue was purified by flash chromatography on silica gel (hexane:ethyl acetate, 3:1) to give the title compound (530 mg).

Step 3.3B {2-[5-amino-2-(3,5-dimethylphenyl)-1H-indol-3-yl]ethyl}benzylcarbamic acid tert-butyl ester Prepared essentially as described in EXAMPLE 3.2E starting from benzyl-{2-[2-(3,5-dimethylphenyl)-5-nitro-1H-indol-3-yl]ethyl}carbamic acid tert-butyl ester (530 mg) to give the title compound (387 mg).

Step 3.3C Benzyl-{2-[2-(3,5-dimethylphenyl)-5-pentanoylamino-1H-indol-3-yl]ethyl}carbamic acid tert-butyl ester To a solution of {2-[5-amino-2-(3,5-dimethylphenyl)-1H-indol-3-yl]ethyl}benzylcarbamic acid tert-butyl ester (200 mg in 10 mL dry methylene chloride) at 0° C. was added 0.18 mL triethylamine followed by the dropwise addition of 0.06 mL valeryl chloride and the mixture stirred at low temperature. After 17 minutes, the reaction was quenched by the addition of saturated aqueous sodium bicarbonate and extracted with ethyl acetate. The organic portion was washed successively with saturated sodium bicarbonate and saturated ammonium chloride then dried over sodium sulfate. Purification of the concentrate by flash chromatography on silica gel (hexane:ethyl acetate, 3:2) gave the title compound (230 mg).

Step 3.3D Benzyl-{2-[5-(2-butylpentazol-1-yl)-2-(3,5-dimethyl phenyl)-1H-indol-3-yl]-ethyl}carbamic acid tert-butyl ester To a solution of benzyl-{2-[2-(3,5-dimethylphenyl)-5-pentanoylamino-1H-indol-3-yl]ethyl}carbamic acid tert-butyl ester (80 mg in 3 mL dry methylene chloride) was added in order 76.6 mg triphenylphosphine, 21 mg imidazole, 72 mg zinc azide(pyridine complex) and 0.048 mL diethyl azodicarboxylate and the mixture stirred at room temperature. After 15 hours an additional portion of zinc azidee•2 pyridine (29 mg) was added. After another 1 hour reaction time, the pot was cooled to room temperature and the reaction mixture applied directly to a silica gel column for purification by flash chromatography (hexane:methylene chloride:ethyl acetate, 3:4:1; then 2:0:1) to give the title compound (57 mg).

Step 3.3E Benzyl-{2-[5-(2-butylpentazol-1-yl)-2-(3,5-dimethylphenyl)-1H-indol-3-yl]ethyl}amine To a solution of benzyl-{2-[5-(2-butylpentazol-1-yl)-2-(3,5-dimethylphenyl)-1H-indol-3-yl]-ethyl}carbamic acid tert-butyl ester (57 mg in 3.5 mL methylene chloride) at 0° C. was added 0.12 mL anisole followed by 0.80 mL trifluoroacetic acid and the mixture stirred at 0° C. After 1.5 hours, the mixture was concentrated in vacuo and the residual acid removed by azeotrope with toluene to give the crude title compound in quantitative yield.

Step 3.3F Benzyl-{2-[5-(2-butylpentazol-1-yl)-2-(3,5-dimethyl-phenyl)-1H-indol-3-yl]ethyl}-(4-pyridin-3-yl-butyl)amine Prepared essentially as described in EXAMPLE 3.2D starting from benzyl-{2-[5-(2-butylpentazol-1-yl)-2-(3,5-dimethylphenyl)-1H-indol-3-yl]ethyl}amine (58 mg) to give the title compound (43 mg).

Step 3.3G {2-[5-(2-butylpentazol-1-yl)-2-(3,5-dimethylphenyl)-1H-indol-3-yl]ethyl}-(4-pyridin-3-yl-butyl)amine Prepared essentially as described in EXAMPLE 3.2I starting from benzyl-{2-[5-(2-butylpentazol-1-yl)-2-(3,5-dimethylphenyl)-1H-indol-3-yl]ethyl}-(4-pyridin-3-yl-butyl)amine (43 mg) to give the title compound (34 mg). m/e=522 (M+H).

EXAMPLE 3.4

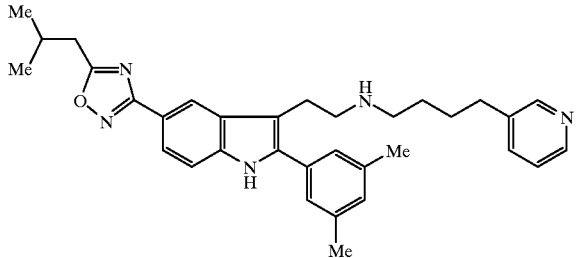

{2-[2-(3,5-dimethylphenyl)-5-(5-isobutyl-[1,2,4]oxadiazol-3-yl)-1H-indol-3-yl]ethyl}-(4-pyridin-3-yl-butyl)amine Step 3.4A {2-[5-cyano-2-(3,5-dimethylphenyl)-1H-indol-3-yl]ethyl}carbamic acid tert-butyl ester Prepared essentially as described in EXAMPLE 3.3A starting from 3-(2-aminoethyl)-2-(3,5-dimethylphenyl)-1H-indole-5-carbonitrile (prepared essentially as described in EXAMPLE 3.2 Step A) to give the title compound (300 mg).

Step 3.4B {2-[2-(3,5-dimethylphenyl)-5-(N-hydroxycarbamimidoyl)-1H-indol-3-yl]ethyl}carbamic acid tert-butyl ester A solution of {2-[5-cyano-2-(3,5-dimethylphenyl)-1H-indol-3-yl]ethyl}carbamic acid tert-butyl ester (300 mg in 5 mL ethanol) was added to a suspension of 725 mg potassium carbonate and 273 mg hydroxylamine hydrochloride in 7 mL ethanol and the whole heated to reflux on an oil bath. After 21 hours, the mixture was cooled to room temperature and filtered to remove solids. The filtrate was concentrated in vacuo then partitioned between ethyl acetate and water. The organic portion was washed with water, dried over sodium sulfate and the concentrate purified by flash chromatography on silica gel (methylene chloride:methanol, 92:8) to give the title compound (105 mg).

Step 3.4C {2-[2-(3,5-dimethylphenyl)-5-(5-isobutyl-[1,2,4]oxadiazol-3-yl)-1H-indol-3-yl]ethyl}carbamic acid tert-butyl ester To a stirred solution of isovaleric acid (0.025 mL in 4 mL methylene chloride) was added 1-hydroxybenzotriazole (37.8 mg) and 1-(3-dimethylaminopropyl)-3-ethylcarbodiimide hydrochloride (43.6 mg) and the reagents allowed to mix for 30 minutes. At this time a solution of {2-[2-(3,5-dimethylphenyl)-5-(N-hydroxycarbamimidoyl)-1H-indol-3-yl]ethyl}carbamic acid tert-butyl ester (81 mg in 3 mL methylene chloride) was added and the reaction stirred at room temperature. After 2 hours, the mixture was concentrated in vacuo and purified by flash chromatography on silica gel (methylene chloride:methanol, 96:4) to give the title compound (81 mg).

Step 3.4D 2-[2-(3,5-dimethylphenyl)-5-(5-isobutyl-[1,2,4]oxadiazol-3-yl)-1H-indol-3-yl]ethylamine Prepared essentially as described in EXAMPLE 3.3E starting from {2-[2-(3,5-dimethylphenyl)-5-(5-isobutyl-[1,2,4]oxadiazol-3-yl)-1H-indol-3-yl]ethyl}carbamic acid tert-butyl ester (67 mg) to give the title compound (48 mg).

Step 3.4E {2-[2-(3,5-dimethylphenyl)-5-(5-isobutyl-1,2,4]oxadiazol-3-yl)-1H-indol-3-yl]ethyl}-(4-pyridin-3-yl-butyl)amine To a solution of 2-[2-(3,5-dimethylphenyl)-5-(5-isobutyl-[1,2,4]oxadiazol-3-yl)-1H-indol-3-yl]ethylamine (22 mg in 1.5 mL chloroform) at 0° C. was added anhydrous magnesium sulfate (38 mg) followed by 4-(3-pyridyl)-butanal (11 mg) and the mixture stirred at low temperature for 15 minutes. At this time sodium borohydride (3.7 mg in 0.50 mL methanol) was added and the mixture stirred at 0° C. After 30 minutes, the reaction was quenched by the addition of water and the mixture extracted with ethyl acetate The organic portion was washed successively with saturated potassium carbonate and brine then dried over sodium sulfate. Purification of the concentrate by flash chromatography on silica gel (methylene chloride:methanol, 92:8) gave the title compound (26.5 mg). m/e=522 (M+H)

EXAMPLE 3.5

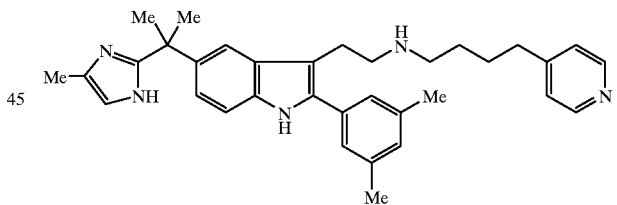

(2-{2-(3,5-dimethylphenyl)-5-[1-methyl-1-(4-methyl-1H-imidazol-2-yl)-ethyl]-1H--indol-3-yl}-ethyl)-(4-pyridin-4-yl-butyl)-amine Step 3.5A 2-[3-(2-tert--butoxycarbonylaminoethyl)-2-(3,5-dimethylphenyl)-1H--indol-5-yl]-2-methyl-propionic acid ethyl ester Prepared essentially as described in EXAMPLE 3.3A starting from 2-[3-(2-aminoethyl)-2-(3,5-dimethylphenyl)-1H--indol-5-yl]-2-methylpropionic acid ethyl ester (EXAMPLE 2, 1.13 g) to give the title compound (1.28 g).

Step 3.5B 2-[3-(2-tert--butoxycarbonylamino-ethyl)-2-(3,5-dimethylphenyl)-1H-indol-5-yl]-2-methylpropionic acid To a stirred solution of 2-[3-(2-tert--butoxycarbonylaminoethyl)-2-(3,5-dimethylphenyl)-1H--indol-5-yl]-2-methyl-propionic acid ethyl ester (1.28 g in 25 mL ethanol) was added 30 mL of 0.5N sodium hydroxide and the mixture heated to 90° C. on an oil bath. After 30 hours the mixture was concentrated in vacuo, diluted with water and extracted with diethyl ether (3×). The aqueous layer was then made acidic by the addition of 0.5N hydrochloric acid and extracted with ethyl acetate. The ethyl acetate layer was washed with water and brine, dried over sodium sulfate and concentrated in vacuo to give the crude title compound (1.23 g).

Step 3.5C (2-{2-(3,5-dimethylphenyl)-5-[1-(methoxymethyl carbamoyl)-1-methyl-ethyl]-1H-indol-3-yl}ethyl)carbamic acid tert--butyl ester To a suspension of 2-[3-(2-tert--butoxycarbonylamino-ethyl)-2-(3,5-dimethylphenyl)-1-H-indol-5-yl]-2-methylpropionic acid (1.23 g in 15 mL N,N-dimethylformamide) at 0° C. was added 608 mg of 1-hydroxybenzotriazole (HOBt), 0.48 mL 4-methylmorpholine and 352 mg of N,O-dimethylhydroxylamine hydrochlorideand the mixture stirred at low temperature. After 15 minutes, 826 mg 1-(3-dimethylaminopropyl)-3-ethylcarbodiimide hydrochloride (EDC) were added and the mixture warmed to room temperature. The reaction was quenched after 3.5 days by concentration in vacuo, resuspending in ethyl acetate and washing sequentially with water, 0.3N sodium bisulfate, water, saturated sodium bicarbonate and brine. The organic portion was dried over sodium sulfate and the concentrate purified by flash chromatography on silica gel (hexane:ethyl acetate, 3:1) to give the title compound (905 mg).

Step 3.5D {2-[5-(1,1-dimethyl-2-oxo-ethyl)-2-(3,5-dimethylphenyl)-1H-indol-3-yl]ethyl}carbamic acid tert--butyl ester To a solution of (2-{2-(3,5-dimethylphenyl)-5-[1-(methoxymethylcarbamoyl)-1-methyl-ethyl]-1H-indol-3-yl}ethyl)carbamic acid tert--butyl ester (296 mg in 5 mL dry tetrahydrofuran) at 0° C. was added 1.8 mL of a 1M lithium aluminum hydride solution in tetrahydrofuran and the mixture stirred at low temperature. After 1 hour, the reaction was quenched by the careful addition of 0.3M aqueous a sodium bisulfate solution. The resulting mixture was extracted with ethyl acetate and the organic portion washed successively with 0.3M aqueous sodium bisulfate, water and brine. This was then dried over sodium sulfate, concentrated in vacuo and purified by flash chromatography on silica gel (hexane:ethyl acetate, 85:15) to give the title compound (253 mg).

Step 3.5E (2-{2-(3,5-dimethylphenyl)-5-[1-methyl-1-(4-methyl-1H-imidazol-2-yl)ethyl]-1H-indol-3-yl}ethyl)carbamic acid tert-butyl ester To a solution of {2-[5-(1,1-dimethyl-2-oxo-ethyl)-2-(3,5-dimethylphenyl)-1H-indol-3-yl]ethyl}carbamic acid tert--butyl ester (475 mg in 15 mL methanol) was added 1 mL of a 40% aqueous solution of pynivic aldehyde followed by 2.2 mL ammonium hydroxide and the mixture stirred at room temperature. After 2 days, an additional portion of 40% aqueous pyruvic aldehyde (0.50 mL) and ammonium hydroxide (1.1 mL) were added. Finally after 4 days the reaction mixture was concentrated in vacuo, the residue resolvated in ethyl acetate and washed sequentially with water and brine. The combined organics were dried over sodium sulfate and the concentrate purified by flash chromatography on silica gel (hexane:ethyl acetate, 1:4) to give the title compound (402 mg).

Step 3.5F 2-{2-(3,5-dimethylphenyl)-5-[1-methyl-1-(4-methyl-1H-imidazol-2-yl)ethyl]-1H-indol-3-yl}ethylamine Prepared essentially as described in EXAMPLE 3.3E starting from (2-{2-(3,5-dimethylphenyl)-5-[1-methyl-1-(4-methyl-1H-imidazol-2-yl)ethyl]-1H-indol-3-yl}ethyl) carbamic acid tert-butyl ester (353 mg) to give the title compound (198 mg).

Step 3.5G (2-{2-(3,5-dimethylphenyl)-5-[1-methyl-1-(4-methyl-1H-imidazol-2-yl)-ethyl]-1H--indol-3-yl}-ethyl)-(4-pyridin-4-yl-butyl)-amine Prepared essentially as described in EXAMPLE 3.2D starting from 2-{2-(3,5-dimethylphenyl)-5-[1-methyl-1-(4-methyl-1H-imidazol-2-yl)ethyl]-1H-indol-3-yl}ethylamine (97 mg) and using 4-pyridin-4-yl butyraldehyde to give the title compound (73 mg). m/e=520 (M+1)

EXAMPLE 4

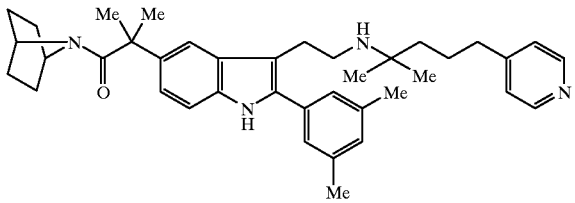

1-(7-azabicclo [2.2.1]hept-7-yl)-2-{2-(3,5-dimethylphenyl)-3-[2-(1,1-dimethyl-4-pyridin-4-yl-butylamino)-ethyl]-1H-indol-5-yl}-2-methyl-propan-1-one Step 4A 1-(3-methyl-but-2-enyl)-tetrahydrothiophenium bromide To a solution of prenyl bromide (2.9 g in 10 mL dry tetrahydrofuran) at 0° C. was added 1.8 mL tetrahydrothiophene and the mixture allowed to warm to room temperature. After 22 hours, the mixture was concentrated in vacuo and the remaining starting materials removed by azeotrope with toluene to give the crude title compound as a white solid (2.2 g).

Step 4B 4-[3-(2-methylpropenyl)oxiranyl]pyridine

To a suspension of 1-(3-methyl-but-2-enyl)-tetrahydrothiophenium bromide (381 mg in 5 mL dry tetrahydrofuran) at 0° C. was added 0.31 mL pyridine-4-carboxaldehyde followed by 111 mg sodium hydride and the mixture allowed to warm to room temperature. After 1.5 hours, an additional 0.15 mL pyridine-4-carboxaldehyde was added and after 30 minutes the reaction quenched by the addition of water. The mixture was partitioned between ethyl acetate and water and the organic portion washed with saturated aqueous sodium bicarbonate and dried over sodium sulfate. Purification of the concentrate by flash chromatography on silica gel (hexane:ethyl acetate, 1:2) gave the title compound (138 mg).

Step 4C 1-(7-azabicyclof2.2.1]hept-7-yl)-2-{2-(3,5-dimethyl-phenyl)-3-[2-(4-hydroxy-1,1-dimethyl-4-pyridin-4-yl-but-2-enylamino)ethyl]-1H-indol-5-yl}-2-methylpropan-1-one To a solution of 2-[3-(2-aminoethyl)-2-(3,5-dimethylphenyl)-1H-indol-5-yl]-1-(7-azabicyclo[2.2.1] hept-7-yl)-2-methylpropan-1-one (prepared essentially as described in EXAMPLE 2, 70 mg in 6 mL dry tetrahydrofuran) was added 2 mL of a solution of 86 mg 4-[3-(2-methylpropenyl)oxiranyl]pyridine in tetrahydrofuran followed by 24 mg tetrakis(triphenylphosphine) palladium and the mixture heated to 65° C. on an oil bath. After 2 hours, the mixture was cooled to room temperature, concentrated in vacuo. The residue was purified by flash chromatography on silica gel (methylene chloride:methanol, 92:8; then 88:12) to give the title compound (91 mg).

Step 4D 1-(7-azabicyclor2.2.1]hept-7-yl)-2-[2-(3,5-dimethyl-phenyl)-3-[2-(1,1-dimethyl-4-pyridin-4-yl-butylamino)-ethyl]-1H-indol-5-yl}-2-methyl-propan-1-one To a solution of 1-(7-azabicyclo[2.2.1]hept-7-yl)-2-{2-(3,5-dimethylphenyl)-3-[2-(4-hydroxy-1,1-dimethyl-4-pyridin-4-yl-but-2-enylamino)ethyl]-1H-indol-5-yl}-2-methylpropan-1-one (27 mg in a mixture of 2 mL dry tetrahydrofuran and 2 mL ethyl acetate) at 0° C. was added 0.010 mL trifluoroacetic anhydride followed by 0.009 mL triethylamine and the mixture stirred at low temperature. After 15 minutes, 0.030 mL acetic acid was added and along with 28 mg palladium hydroxide on carbon. The reaction flask was fitted with a hydrogen balloon, evacuated and recharged with hydrogen (3 times) and stirred at room temperature. After 8 hours the reaction was flushed with nitrogen, filtered over diatomaceous earth and concentrated in vacuo. Purification by flash chromatography on silica gel (methylene chloride:methanol:ammonium hydroxide, 94:6:1) gave the title compound (15 mg). m/e=591 (M+H).

EXAMPLE 5.1

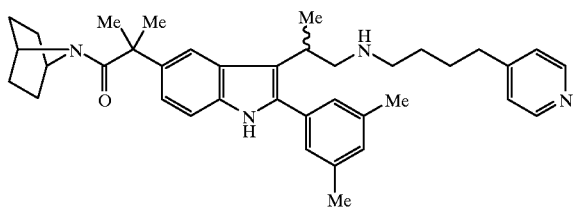

1-(7-azabicyclo[2.2.1]hept-7-yl)-2-{2-(3,5-dimethylphenyl)-3-[1-methyl-2-(4-pyridin-4-yl-butylamino)ethyl]-1H-indol-5-yl}-2-methylpropan-1-one Step 5.1A 2-methylcyclopropanecarboxylic acid N-methoxy-N-methyl-amide To a solution of 2-methylcyclopropanecarboxylic acid (10 g in a mixture of 200 mL benzene and 2 mL N,N-dimethylformamide) at 0° C was added 10.5 mL of oxalyl chloride and the mixture stirred at 0° C. for 30 minutes then warmed to room temperature for 30 minutes. At this time, 14.6 g of N,O-dimethylhydroxylamine hydrochloride was added followed by 41 mL of triethylamine. The mixture was stirred at room temperature for one hour then quenched by the addition of saturated sodium bicarbonate. The aqueous portion was extracted with ethyl acetate and the combined organics washed with brine, dried over sodium sulfate and concentrated in vacuo. The product was purified by distillation under reduced pressure to give 8.9 g as an oil.

Step 5.1B (3,5-dimethylphenyl)-(2-methylcyclopropyl) methanone

To a solution of 5-bromo-meta-xylene (5.7 mL in 120 mL of dry tetrahydrofuran) at −78° C. was added 30.6 mL of a 1.4M solution of n-butyllithium in hexane and the mixture stirred at low temperature. After 15 minutes, a solution of 2-methylcyclopropanecarboxylic acid N-methoxy-N-methyl-amide (5.0 g in 50 mL tetrahydrofuran) was added dropwise over 5 minutes and the mixture then allowed to warm slowly to room temperature. After 1 hour, the reaction was quenched by the addition of 20 mL 2N hydrochloric acid and 40 mL water. This was extracted with ethyl acetate washed with saturated sodium bicarbonate and brine then dried over sodium sulfate to give 6.95 g of the title compound (crude).

Step 5.1C 2-[3-(2-amino-1-methylethyl)-2-(3,5-dimethylphenyl)-1H-indol-5-yl]-2-methylpropionic acid ethyl ester To a solution of 2-(4-hydrazinophenyl)-2-methylpropionic acid ethyl ester (5.7 g in 20 mL n-butanol) was added 4 g (3,5-dimethylphenyl)-(2-methylcyclopropyl) methanone followed by 1.3 mL conc. hydrochloric acid and the mixture heated to 110° C. on an oil bath. After 16 hours, the mixture was cooled to room temperature and concentrated in vacuo. The residue was dissolved in ethyl acetate and washed sequentially with 0.5 N sodium hydroxide, water and brine. The combined organics were dried over sodium sulfate and concentrated in vacuo. Purification by flash chromatography on silica gel (methylene chloride:methanol, 95:5) gave the title compound (2.5 g).

Step 5.1D 2-{2-(3,5-dimethylphenyl)-3-[1-methyl-2-(4-pyridin-4-yl-butylamino)-ethyl]-1H-indol-5-yl}-2-methylpropionic acid ethyl ester Prepared essentially as described in EXAMPLE 2, Step A from 2-[3-(2-amino-1-methylethyl)-2-(3,5-dimethylphenyl)-1H-indol-5-yl]-2-methylpropionic acid ethyl ester (233 mg) to give the title compound (258 mg).

Step 5.1E 2-[3-{2-[benzyloxycarbonyl-(4-pyridin-4-yl-butyl)-amino]-1-methyl-ethyl}-2-(3,5-dimethylphenyl)-1H-indol-5-yl]-2-methylpropionic acid ethyl ester Prepared essentially as described in EXAMPLE 2, Step B from 2-{2-(3,5-dimethylphenyl)-3-[1-methyl-2-(4-pyridin-4-yl-butylamino)-ethyl]-1H-indol-5-yl}-2-methylpropionic acid ethyl ester (258 mg) to give the title compound (240 mg).

Step 5.1F 2-[3-{2-[benzyloxycarbonyl-(4-pyridin-4-yl-butyl)aminol-1-methylethyl}-2-(3,5-dimethylphenyl)-1H-indol-5-yl]-2-methylpropionic acid Prepared essentially as described in EXAMPLE 2, Step C from 2-[3-{2-[benzyloxycarbonyl-(4-pyridin-4-yl-butyl)-amino]-1-methyl-ethyl}-2-(3,5-dimethylphenyl)-1H-indol-5-yl]-2-methylpropionic acid ethyl ester (240 mg) to give the title compound (222 mg).

Step 5.1G {2-[5-[2-(7-azabicyclo[2.2.1]hept-7-yl)-1,1-dimethyl-2-oxo-ethyl]-2-(3,5-dimethylphenyl)-1H-indol-3-yl]propyl}-(4-pyridin-4-yl-butyl)carbamic acid benzyl ester Prepared essentially as described in EXAMPLE 2, Step D from 2-[3-(2-[benzyloxycarbonyl-(4-pyridin-4-yl-butyl) amino]-1-methylethyl}-2-(3,5-dimethylphenyl)-1H-indol-5-yl]-2-methylpropionic acid (91 mg) to give the title compound (66 mg).

Step 5.1H 1-(7-azabicyclo[2.2.1]hept-7-yl)-2-{2-(3,5-dimethylphenyl)-3-[1-methyl-2-(4-pyridin-4-yl-butylamino)ethyl]-1H-indol-5-yl}-2-methylpropan-1-one Prepared essentially as described in EXAMPLE 2, Step E from {2-[5-[2-(7-azabicyclo[2.2.1]hept-7-yl)-1,1-dimethyl-2-oxo-ethyl]-2-(3,5-dimethylphenyl)-1-H-indol-3-yl] propyl}-(4-pyridin-4-yl-butyl)carbamic acid benzyl ester (62 mg) to give the title compound (27 mg). m/e=577 (M+H).

EXAMPLE 5.2

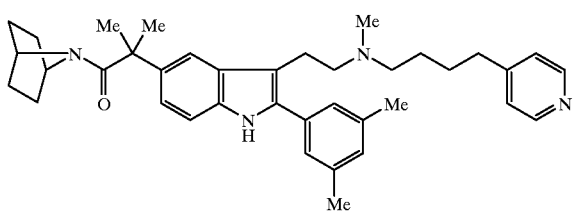

1-(7-azabicyclo[2.2.1]hept-7-yl)-2-[2-(3,5-dimethylphenyl)-3-[2-[methyl-[4-(pyridin-4-yl) butyl]amino]ethyl]-1H-indol-5-yl)-2-methylpropan-1-one A dry flask containing 120 mg (0.21 mmol) of 1-(7-azabicyclo[2.2.1]hept-7-yl)-2-[2-(3,5-dimethylphenyl)-3-[2-[4-(pyridin-4-yl)butylamino]ethyl]-1H-indol-5-yl]-2-methylpropan-1-one (prepared essentially as described in EXAMPLE 2), 63.0 mg (2.1 mmol) of paraformaldehyde, and 200 mg of powdered 3A molecular sieves was fitted with a septum and purged thoroughly with nitrogen. Next, 5 mL of methanol and 0.121 mL (126.1 mg, 2.1 mmol) of glacial acetic acid were added, and the mixture was stirred at room temperature for 15 minutes. Then 52.8 mg (0.84 mmol) of sodium cyanoborohydride was added, followed after an additional 25 minutes by 2.5 mL of anhydrous tetrahydrofuran. After 1 day, the mixture was filtered, and the filter cake was washed thoroughly with methylene chloride. The filtrate was shaken in a separatory funnel with water. The aqueous phase was extracted an additional 3 times with methylene chloride. The combined organic fractions were dried over sodium sulfate, filtered, and concentrated in vacuo. The residue was flash chromatographed on silica gel (gradient elution with 99:1:0.1 to 95:5:0.5 $CH_2Cl_2$-MeOH-concd. $NH_4O$) to yield 95.4 mg (79%) of a yellow, stiff foam; homogeneous by TLC in 95:5:0.5 $CH_2Cl_2$-MeOH-concd. $NH_4OH$. 500 MHz $^1H$ NMR ($CDCl_3$) was consistent with the assigned structure. Mass spectrum (ESI): m/e= 577.5 (M+H).

EXAMPLE 6

Following procedures similar to that described in EXAMPLES 1 through 5, and Schemes O and P, the following compounds are prepared:

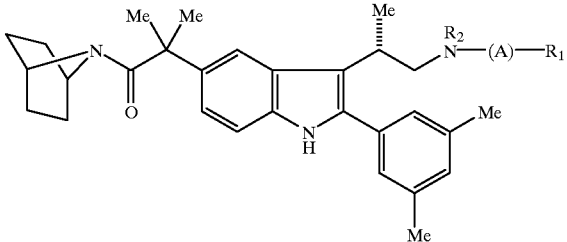

| Ex. # | —(A)—$R_1$ | $R_2$ |
|---|---|---|
| 6A | 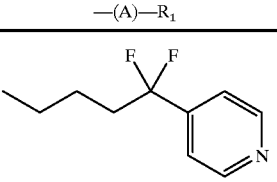 | H |
| 6B | 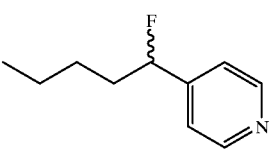 | Me |
| 6C | 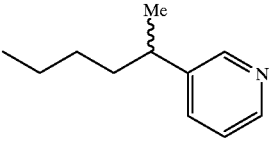 | H |
| 6D | 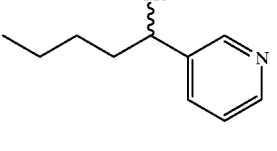 | H |
| 6E | 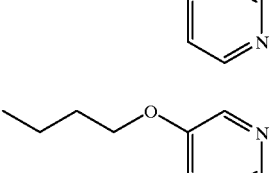 | Me |
| 6F | 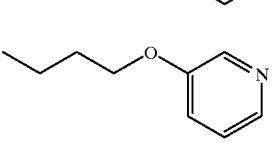 | H |
| 6G | 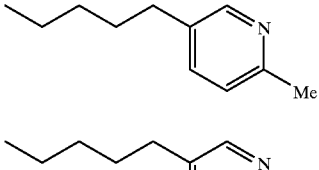 | H |
| 6H | 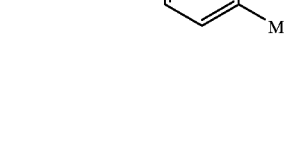 | Me |
| 6I |  | H |
| 6J | 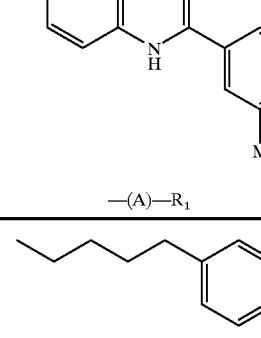 | H |
| 6K | 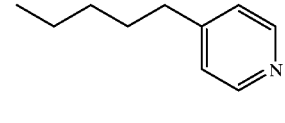 | Me |
| 6L | 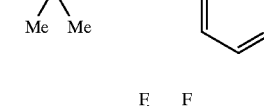 | H |
| 6M | 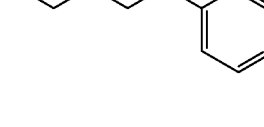 | Me |

-continued

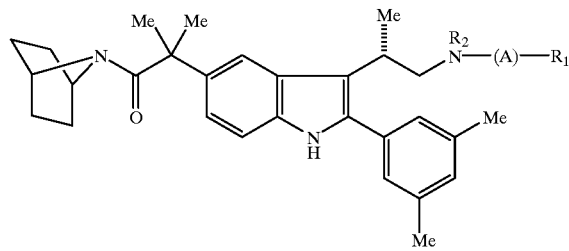

| Ex. # | —(A)—R₁ | R₂ |
|---|---|---|
| 6N | pentyl-(2-methylpyridin-4-yl) | H |
| 6O | pentyl-(5-chloropyridin-3-yl) | H |
| 6P | pentyl-(3-chloropyridin-4-yl) | H |
| 6Q | pentyl-(3,5-dichloropyridin-4-yl) | H |
| 6R | propyl-(pyridin-3-yl) | H |
| 6S | propyl-(pyridin-3-yl) | Me |
| 6T | propyl-(pyridin-4-yl) | H |
| 6U | sec-butyl-(pyridin-4-yl) | H |
| 6V | tert-pentyl-(pyridin-4-yl) | H |

-continued

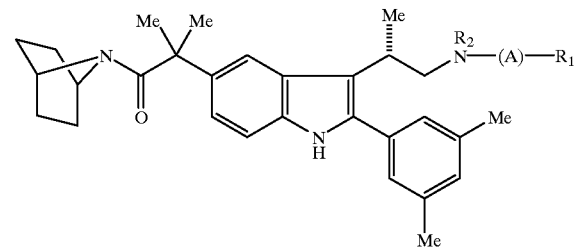

| Ex. # | —(A)—R₁ | R₂ |
|---|---|---|
| 6W | ethyl-(quinolin-5-yl) | H |
| 6X | pentyl-(3-fluoropyridin-4-yl) | H |
| 6Y | pentyl-(4,6-dimethylpyridin-3-yl) | H |
| 6Z | pentyl-(2,4-dimethylpyridin-3-yl) | H |
| 6AA | pentyl-(pyrimidin-4-yl) | H |
| 6BB | butoxy-(6-methylpyridin-3-yl) | H |
| 6CC | butoxy-(6-methylpyridin-3-yl) | Me |
| 6DD | propoxymethyl-(pyridin-3-yl) | H |
| 6EE | propoxymethyl-(pyridin-3-yl) | Me |

-continued

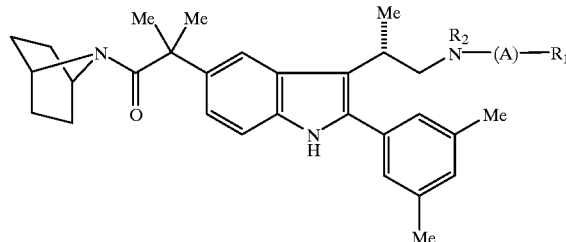
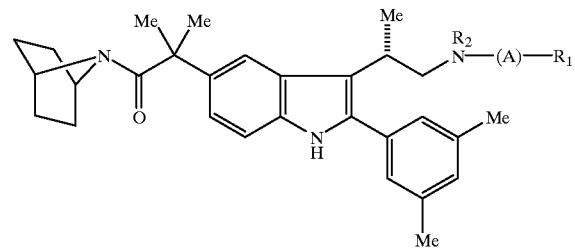

| Ex. # | —(A)—R₁ | R₂ |
|---|---|---|
| 6FF | (2-methyl-2-(4-pyridyl)pentyl chain with gem-dimethyl) | H |
| 6GG | (butyl chain with methyl branch to 3-pyridyl) | H |
| 6HH | (butyl chain with methyl branch to 3-pyridyl) | H |
| 6II | propyl-4-pyridyl | Me |
| 6JJ | pentyl-4-pyridyl | i-Pr |
| 6KK | pentyl-4-pyridyl | Et |
| 6LL | butyl-isoquinolinyl | H |
| 6MM | butyl-isoquinolinyl | H |
| 6NN | pentyl-(6-ethyl-3-pyridyl) | H |

| Ex. # | —(A)—R₁ | R₂ |
|---|---|---|
| 6OO | butoxy-(2-methyl-4-pyridyl) | H |
| 6PP | pentyl-(2-ethyl-4-pyridyl) | H |
| 6QQ | propyl-S-CH₂-(3-pyridyl) | H |
| 6RR | propyl-S-(4-pyridyl) | H |
| 6SS | propyl-N(Me)-SO₂-(3-pyridyl) | H |
| 6TT | butoxy-(4-pyrimidinyl) | H |
| 6UU | pentyl-(2-pyrazinyl) | H |
| 6VV | pentyl-(6-quinolinyl) | H |
| 6WW | butyl-(6-quinolinyl) | H |

-continued

| Ex. # | —(A)—R₁ | R₂ |
|---|---|---|
| 6XX | pentyl-pyrimidin-5-yl | H |
| 6YY | propyl-(2-methylpyridin-4-yl) | H |
| 6ZZ | propyl-(3-methylpyridin-4-yl) | H |
| 6AAA | propyl-(6-ethylpyridin-3-yl) | H |
| 6BBB | propyl-(5-chloropyridin-3-yl) | H |
| 6CCC | (2-methylpropyl)-pyridin-4-yl | H |
| 6DDD | (2-methylpropyl)-pyridin-4-yl | H |
| 6EEE | butyl-pyridin-4-yl | H |
| 6FFF | ethyl-pyridin-4-yl | H |
| 6GGG | butyl-S-pyrimidin-4-yl | H |
| 6HHH | pentyl-isoquinolin-6-yl | H |
| 6III | butyl-isoquinolin-6-yl | H |
| 6JJJ | pentyl-pyridazin-4-yl | H |
| 6KKK | pentyl-(5-fluoropyridin-3-yl) | H |
| 6LLL | propyl-(3-methylpyridin-4-yl) | H |
| 6MMM | propyl-(3-chloropyridin-4-yl) | H |
| 6NNN | propyl-(6-methylpyridin-3-yl) | H |
| 6OOO | propyl-(2-methylpyridin-3-yl) | H |
| 6PPP | propyl-isoquinolin-5-yl | H |

-continued

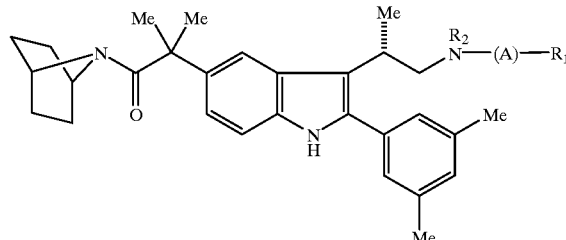

| Ex. # | —(A)—R$_1$ | R$_2$ |
|---|---|---|
| 6QQQ | propyl-2-pyridyl | H |
| 6RRR | pentyl-(2-amino)-5-pyridyl | H |
| 6SSS | pentyl-(3-amino)-5-pyridyl | H |
| 6TTT | pentyl-(3-COOH)-5-pyridyl | H |
| 6UUU | pentyl-5-(3-pyrrolidinylcarbonyl)pyridyl | H |
| 6VVV | pentyl-(2-Me)-4-pyrimidinyl | H |
| 6WWW | butyloxy-2-pyrazinyl | H |
| 6XXX | propyl-(2-F)-4-pyridyl | H |
| 6YYY | propyl-(3-F)-4-pyridyl | H |

-continued

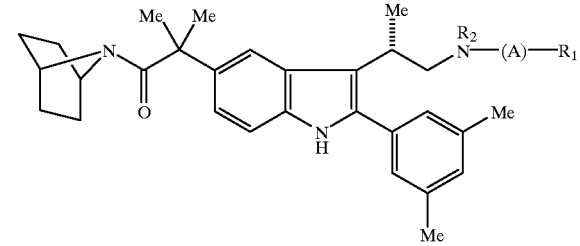

| Ex. # | —(A)—R$_1$ | R$_2$ |
|---|---|---|
| 6ZZZ | pentyl-(3-NHSO$_2$Me)-5-pyridyl | H |
| 6AAAA | propanoylamino-4-pyrimidinyl | H |
| 6BBBB | propyl-(4-Me)-5-thiazolyl | H |
| 6CCCC | propyl-(2-Me)-4-thiazolyl | H |
| 6DDDD | propyl-5-benzimidazolyl | H |
| 6EEEE | propyl-1-imidazolyl | H |
| 6FFFF | propyl-(2-Me)-5-benzimidazolyl | H |
| 6GGGG | propyl-3-pyridazinyl | H |
| 6HHHH | propyl-(2-amino)-4-thiazolinyl | H |
| 6IIII | propyl-(2-NHC(O)OEt)-4-thiazolinyl | H |

-continued

| Ex. # | —(A)—R₁ | R₂ |
|---|---|---|
| 6JJJJ | 4-propyl-thiazol-2-yl-NHC(O)Me | H |
| 6KKKK | 4-ethyl-2-methylpyridine | H |
| 6LLLL | 5-ethyl-2-methyl-benzimidazole | H |
| 6MMMM | 4-propyl-thiazol-2-yl-NHC(O)NHEt | H |
| 6NNNN | 4-propyl-2-ethyl-thiazole | H |
| 6OOOO | 4-propyl-thiazol-2-yl-NHC(O)N(Et)₂ | H |
| 6PPPP | 4-propyl-thiazol-2-yl-NHC(O)CH₂CH₂Me | H |
| 6QQQQ | 4-propyl-thiazol-2-yl-NHC(O)-cyclopropyl | H |
| 6RRRR | 2-propyl-thiazole | H |
| 6SSSS | 4-propyl-thiazole | H |
| 6TTTT | 4-propyl-thiazol-2-yl-CH₂OH | H |
| 6UUUU | 4-propyl-thiazole-2-carboxylic acid | H |
| 6VVVV | 5-propyl-1H-benzotriazole | H |
| 6WWWW | 5-propyl-1-methyl-benzotriazole | H |
| 6XXXX | 6-propyl-1-methyl-benzotriazole | H |
| 6YYYY | 5-propyl-2-methyl-benzotriazole | H |
| 6ZZZZ | 5-propyl-1H-indazole | H |
| 6AAAAA | 4-propyl-pyridine N-oxide | H |
| 6BBBBB | 4-propyl-2-methyl-pyridine N-oxide | H |

-continued
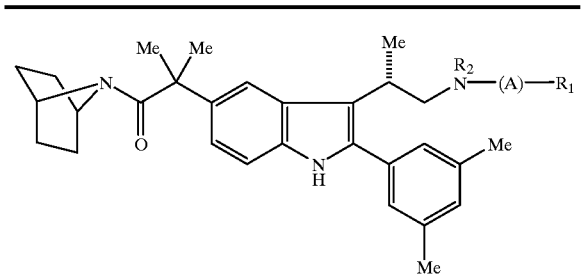
| Ex. # | —(A)—R$_1$ | R$_2$ |
|---|---|---|
| 6CCCCC | 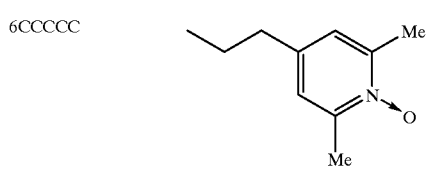 | H |
| 6DDDDD | | H |
-continued
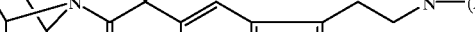
| Ex. # | —(A)—R$_1$ | R$_2$ |
|---|---|---|
| 6EEEEE | 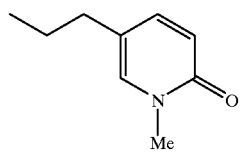 | H |
| 6FFFFF | | H |
EXAMPLE 7
Following procedures similar to that described in EXAMPLES 1 through 5, and Scheme P, the following compounds are prepared:
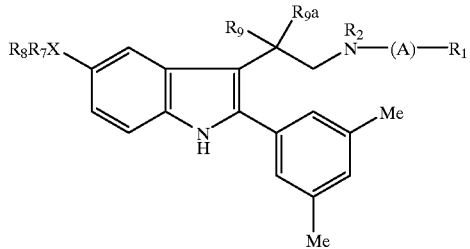
| Ex. # | X—R$_7$R$_8$ | —(A)—R$_1$ | R$_2$ | R9, R9a |
|---|---|---|---|---|
| 7A | | 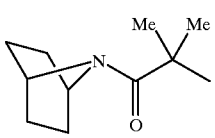 | H | H, H |
| 7B | | 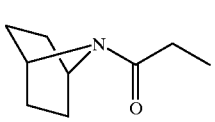 | H | H, H |

-continued
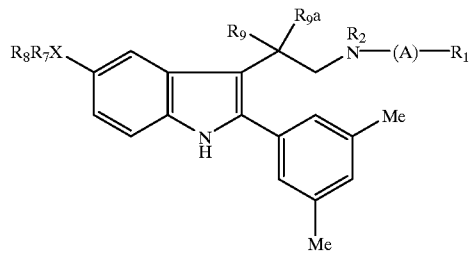
| Ex. # | X—R7R8 | —(A)—R1 | R2 | R9, R9a |
|---|---|---|---|---|
| 7C | quinuclidine-N-C(=O)-C(Me)(Et)- | pentyl-4-pyridyl | H | H, H |
| 7D | quinuclidine-N-C(=O)-CH(Me)(Et) | pentyl-4-pyridyl | H | H, H |
| 7E | quinuclidine-N-C(=O)-C(Me)2- | pentyl-4-pyridyl | H | Me, Me |
| 7F | quinuclidine-N-C(=O)-(1-Me-cyclobutyl) | pentyl-4-pyridyl | H | H, H |
| 7G | 3,3-diMe-azetidine-N-C(=O)-C(Me)2- | pentyl-4-pyridyl | H | H, H |
| 7H | 2-azabicyclo[2.2.2]octane-N-C(=O)-C(Me)2- | butyl-4-pyridyl | H | H, H |

EXAMPLE 8
Following procedures similar to that described in EXAMPLES 1 through 5, and Scheme P, the following compounds are prepared:
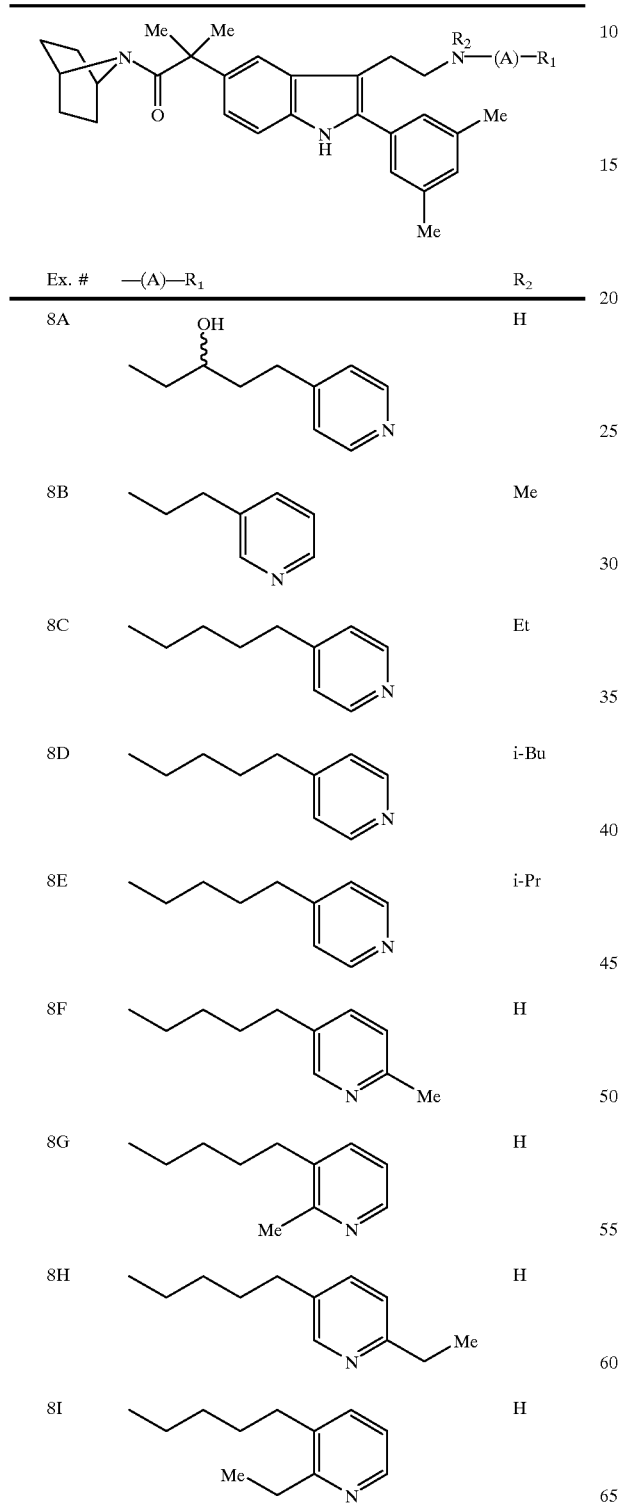
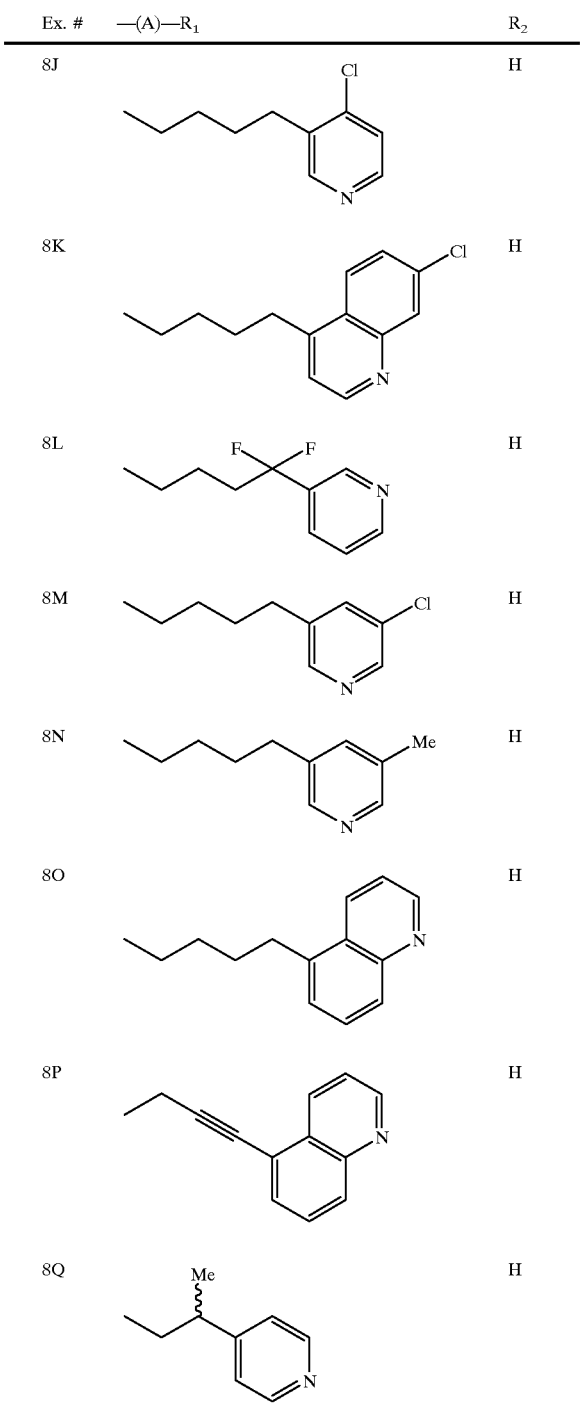

-continued
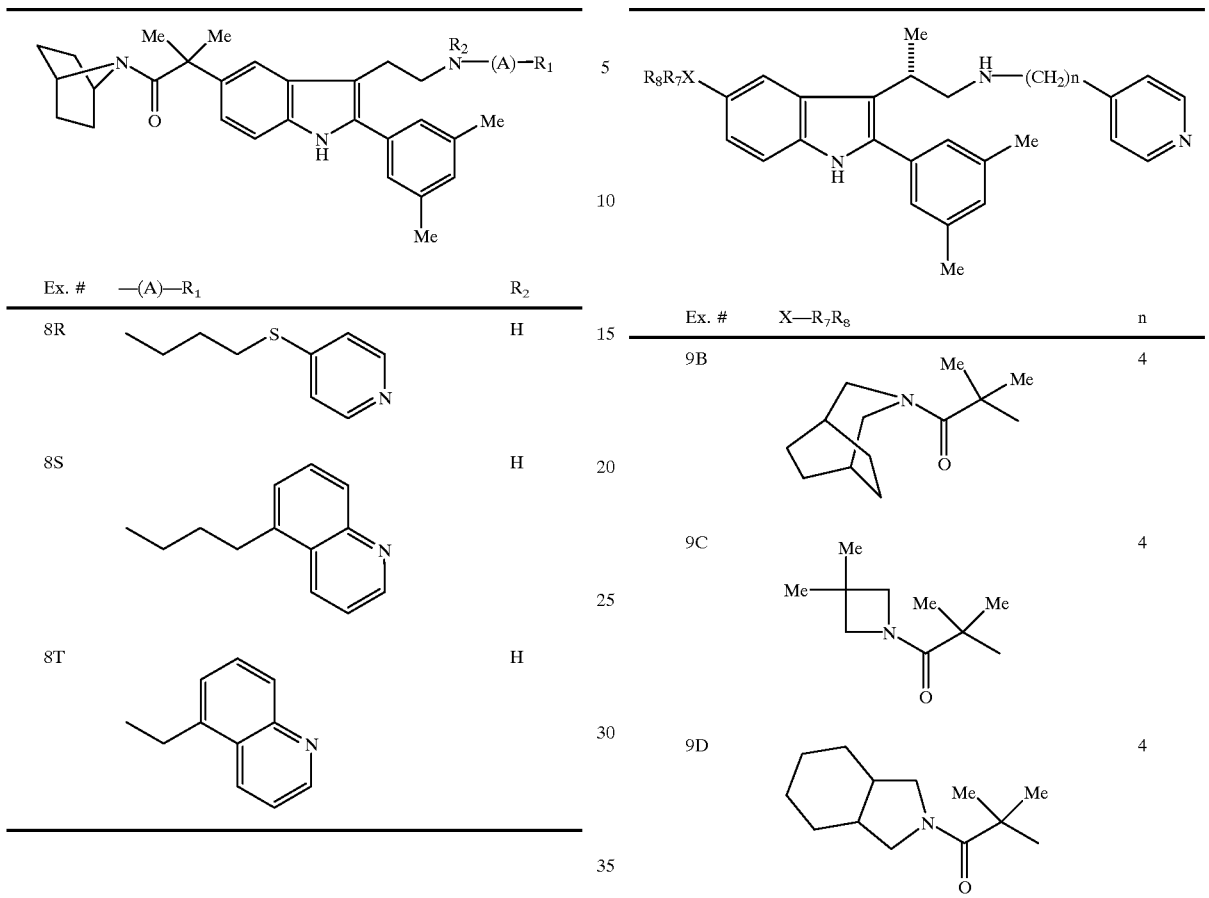
EXAMPLE 9
Following procedures similar to that described in EXAMPLES 1 through 5, and Scheme P, the following compounds are prepared:
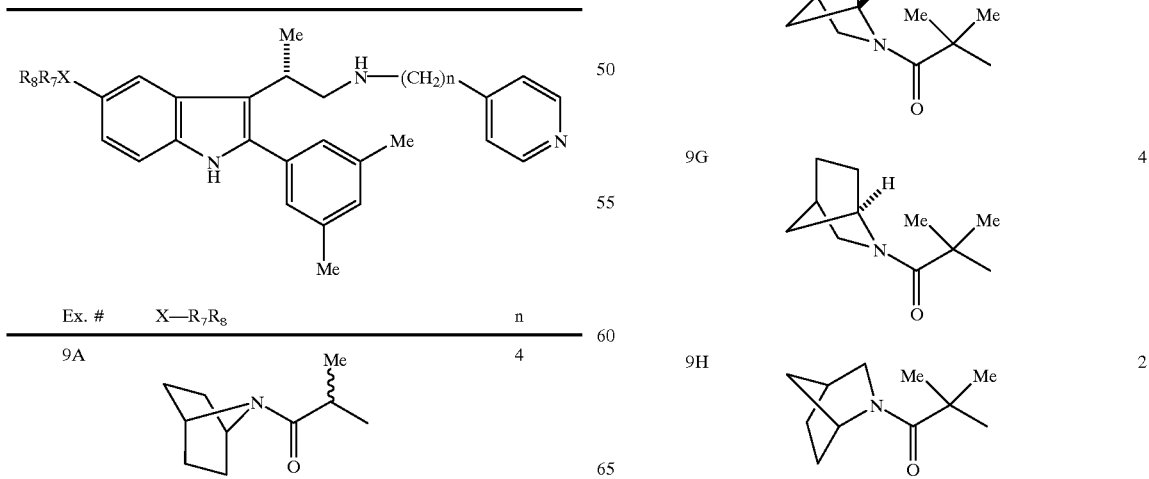

-continued
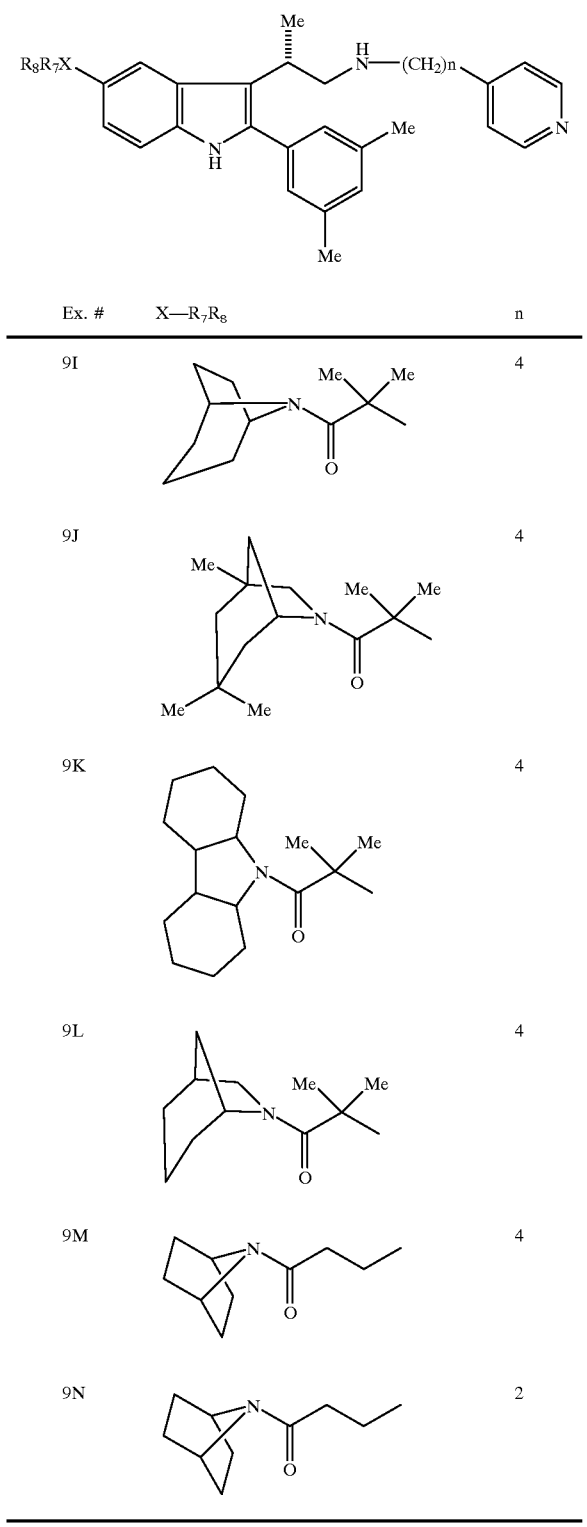
| Ex. # | X—R₇R₈ | n |
|---|---|---|
| 9I | | 4 |
| 9J | | 4 |
| 9K | | 4 |
| 9L | | 4 |
| 9M | | 4 |
| 9N | | 2 |
Following procedures similar to that described in EXAMPLES 1 through 5, and Scheme P, the following compounds are prepared:
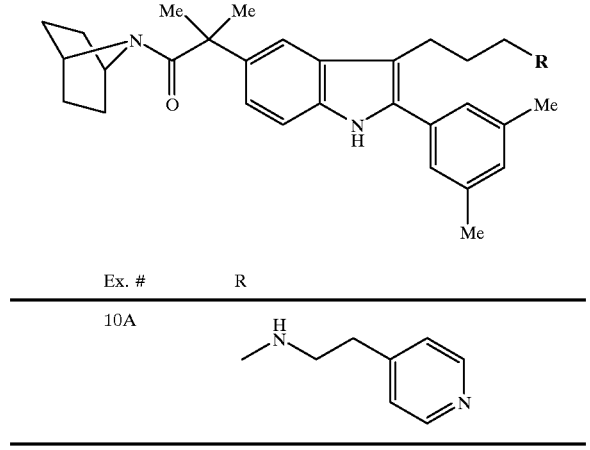
| Ex. # | R |
|---|---|
| 10A | |
EXAMPLE 11
Following procedures similar to that described in EXAMPLES 1 through 5, and Scheme P, the following compounds are prepared:
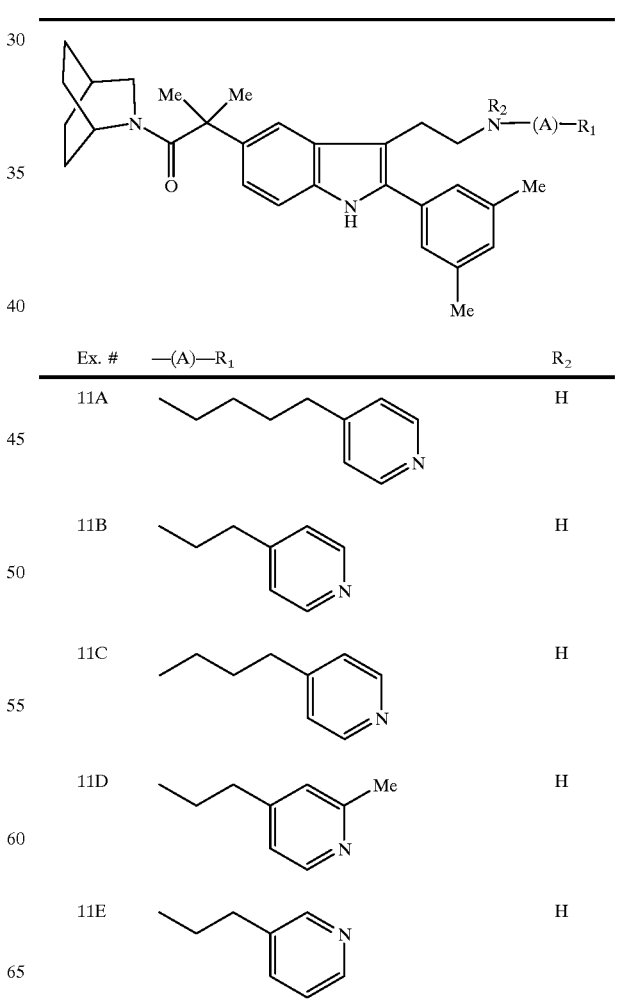
| Ex. # | —(A)—R₁ | R₂ |
|---|---|---|
| 11A | | H |
| 11B | | H |
| 11C | | H |
| 11D | | H |
| 11E | | H |

-continued
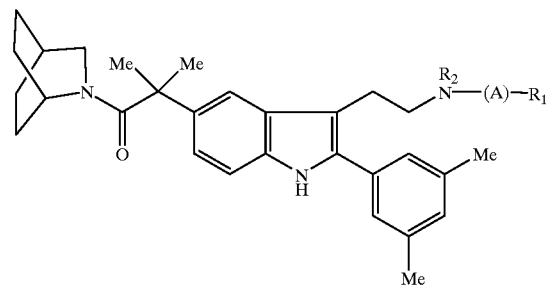
| Ex. # | —(A)—R$_1$ | R$_2$ |
|---|---|---|
| 11F | 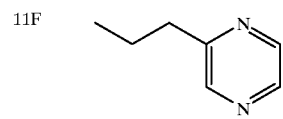 | H |
| 11G | 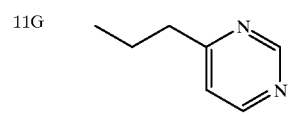 | H |
| 11H | 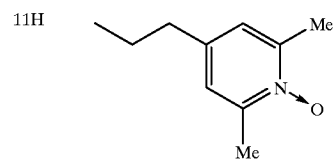 | H |
| 11I | 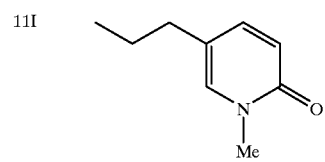 | H |
| 11J | 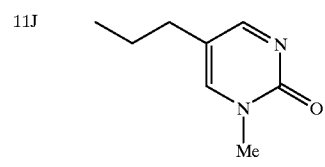 | H |
| 11K | 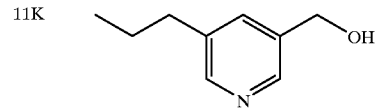 | H |
| 11L | 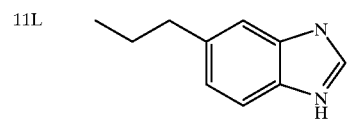 | H |
| 11M | 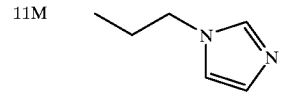 | H |
| 11N | 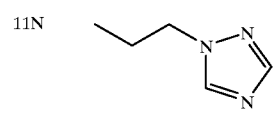 | H |
-continued
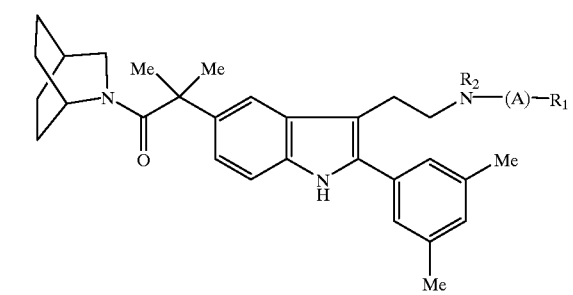
| Ex. # | —(A)—R$_1$ | R$_2$ |
|---|---|---|
| 11O | 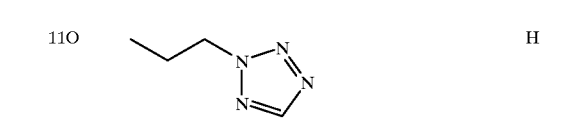 | H |
| 11P | 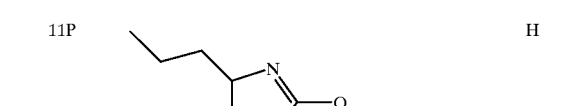 | H |
| 11Q | 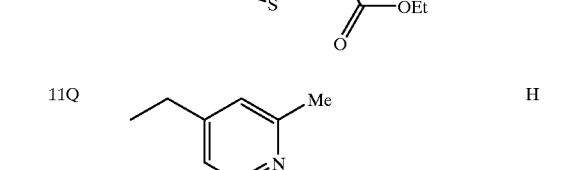 | H |
| 11R | 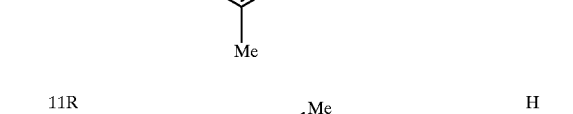 | H |
| 11S | 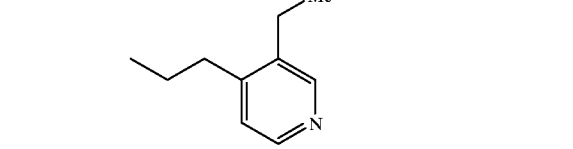 | H |
| 11T | 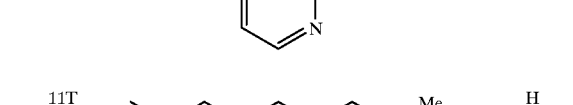 | H |
| 11U | 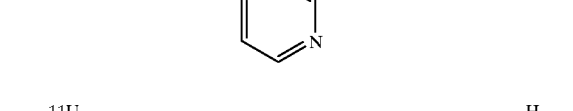 | H |
| 11V | 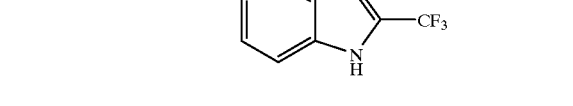 | H |

-continued
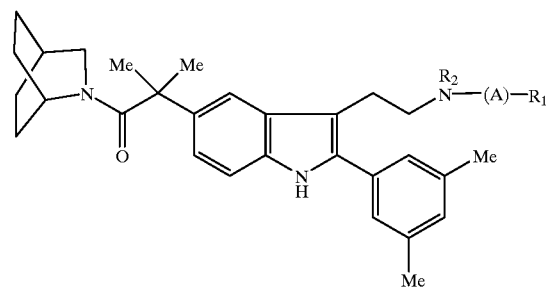
| Ex. # | —(A)—R₁ | R₂ |
|---|---|---|
| 11W | 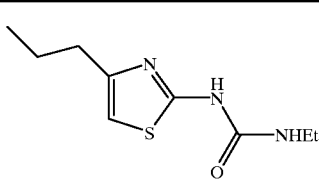 | H |
| 11X | 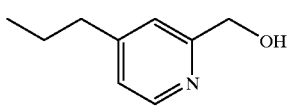 | H |
| 11Y | 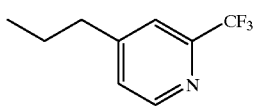 | H |
| 11Z | 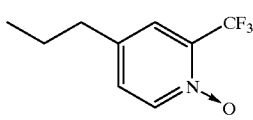 | H |
| 11AA | 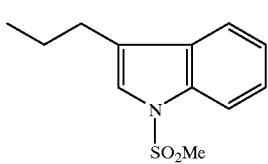 | H |
| 11BB | 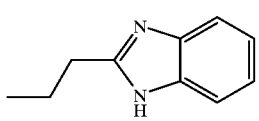 | H |
| 11CC | 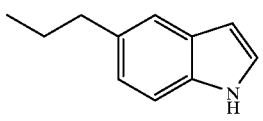 | H |
| 11DD | 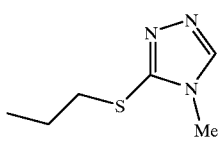 | H |
-continued
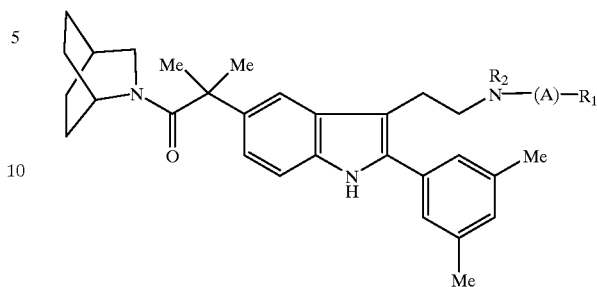
| Ex. # | —(A)—R₁ | R₂ |
|---|---|---|
| 11EE | 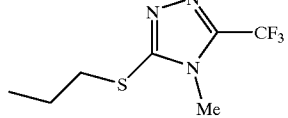 | H |
| 11FF | 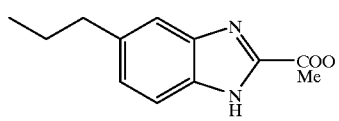 | H |
| 11GG | 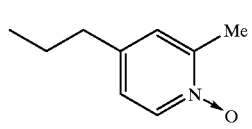 | H |
| 11HH | 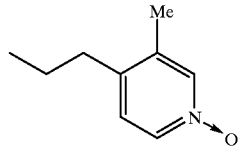 | H |
| 11II | 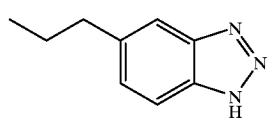 | H |
| 11JJ | 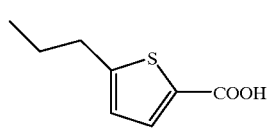 | H |
| 11KK | 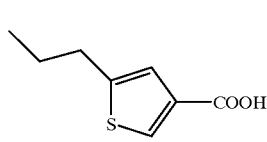 | H |
| 11LL | 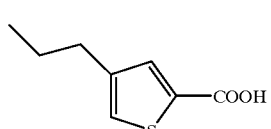 | H |

-continued

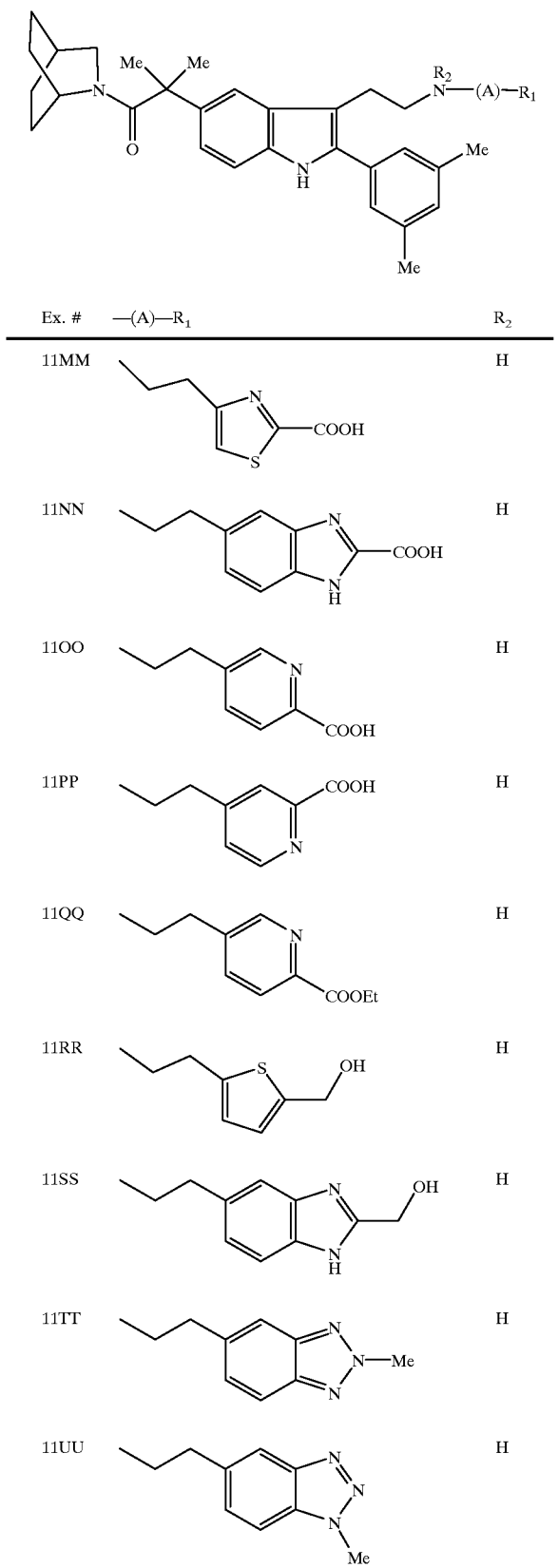

| Ex. # | —(A)—R₁ | R₂ |
|---|---|---|
| 11MM | propyl-thiazole-COOH | H |
| 11NN | propyl-benzimidazole-COOH | H |
| 11OO | propyl-pyridine-COOH | H |
| 11PP | propyl-pyridine-COOH | H |
| 11QQ | propyl-pyridine-COOEt | H |
| 11RR | propyl-thiophene-CH₂OH | H |
| 11SS | propyl-benzimidazole-CH₂OH | H |
| 11TT | propyl-(2-Me)benzotriazole | H |
| 11UU | propyl-(1-Me)benzotriazole | H |

-continued

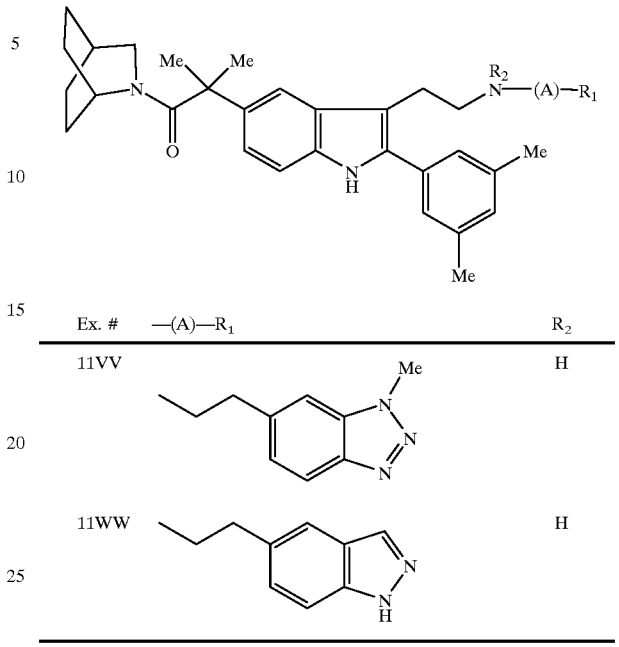

| Ex. # | —(A)—R₁ | R₂ |
|---|---|---|
| 11VV | propyl-(1-Me)benzotriazole | H |
| 11WW | propyl-indazole | H |

EXAMPLE 12

Following procedures similar to that described in EXAMPLES 1 through 5, and Scheme P, the following compounds are prepared:

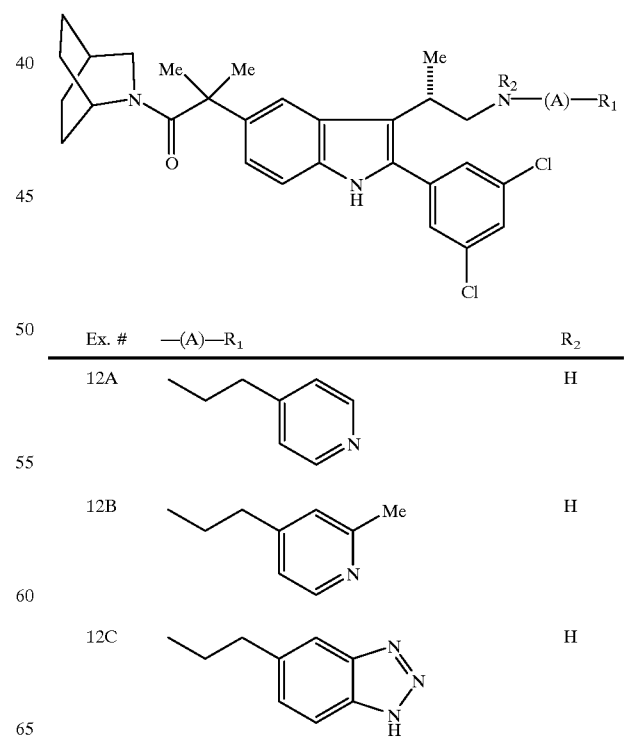

| Ex. # | —(A)—R₁ | R₂ |
|---|---|---|
| 12A | propyl-pyridine | H |
| 12B | propyl-(2-Me)pyridine | H |
| 12C | propyl-benzotriazole | H |

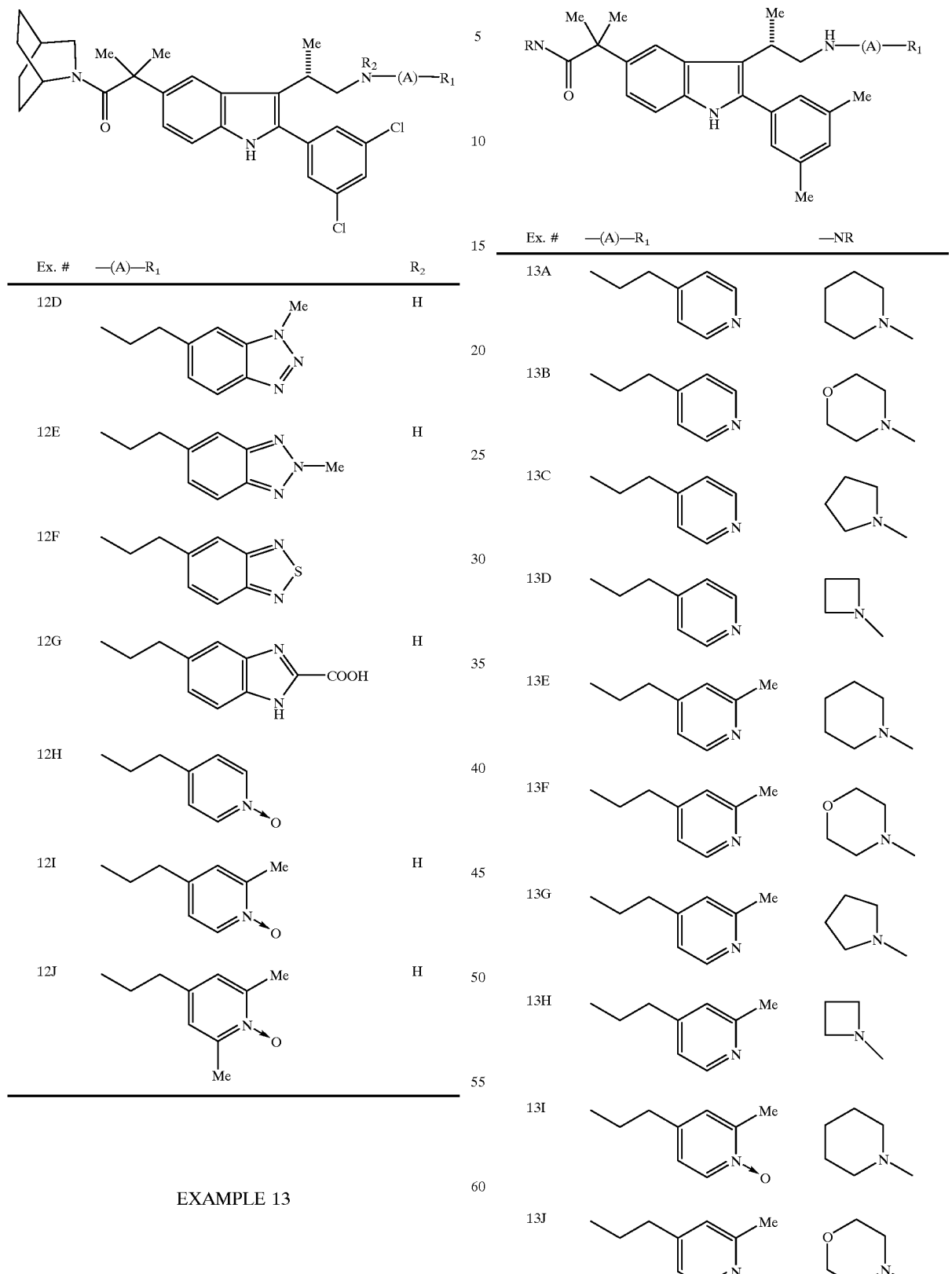
EXAMPLE 13
Following procedures similar to that described in EXAMPLES 1 through 5, and Scheme P, the following compounds are prepared:

-continued
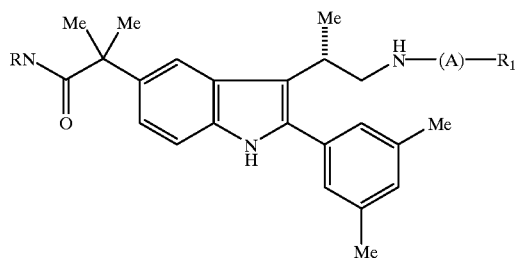
| Ex. # | —(A)—R₁ | —NR |
|---|---|---|
| 13K | 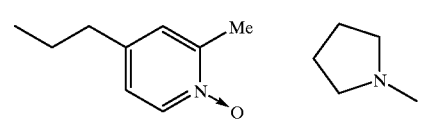 | 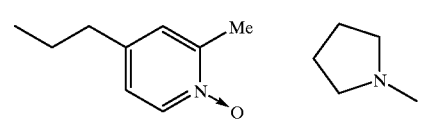 |
| 13L | | |
| 13M | | |
| 13N | | |
| 13O | | |
| 13P | | |
What is claimed is:
1. The compound of the formula
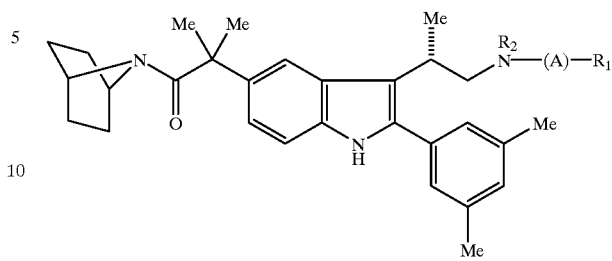
or a pharmaceutically acceptable addition salt and/or hydrate thereof, or where applicable, a geometric or optical isomer or racemic mixture thereof;
wherein $R_1$, $R_2$ and A are as indicated in the table below:
| -(A)-R₁ | R₂ |
|---|---|
| 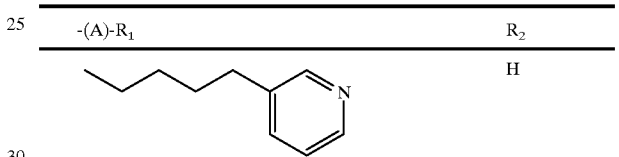 | H |
| | Me |
| 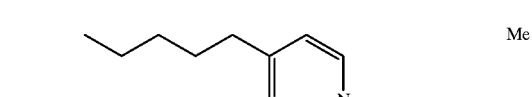 | H |
| 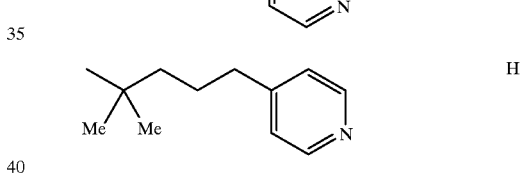 | H |
| | Me |
| 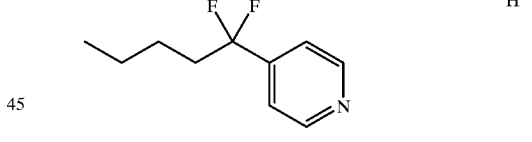 | H |
| 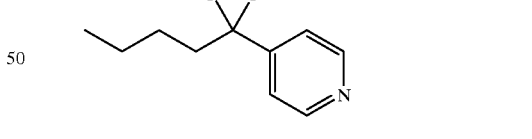 | H |

-continued
| -(A)-R₁ | R₂ |
|---|---|
| 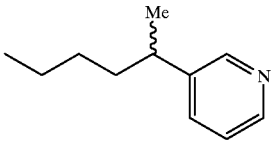 | Me |
| 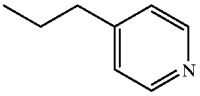 | H |
| 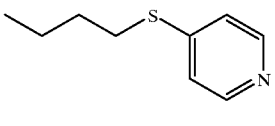 | H |
| 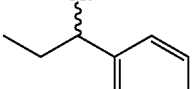 | Me |
| 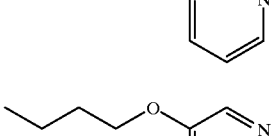 | H |
| 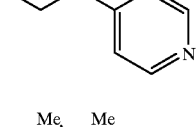 | Me |
| 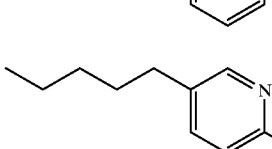 | H |
| 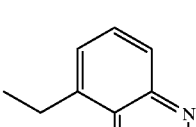 | H |
| 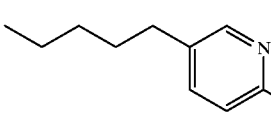 | H |
| 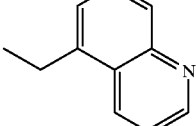 | H |
| 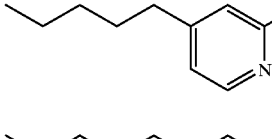 | H |
| 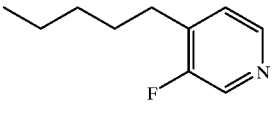 | Me |
-continued
| -(A)-R₁ | R₂ |
|---|---|
| 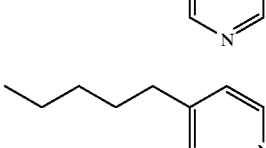 | H |
| 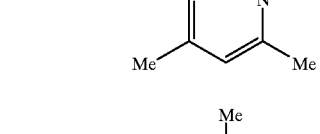 | H |
| 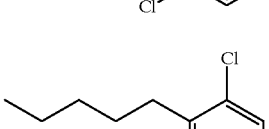 | H |
| 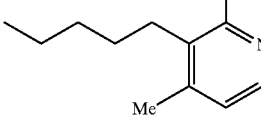 | H |
| 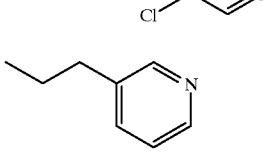 | H |
| 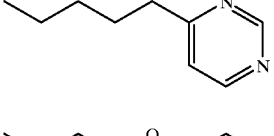 | H |
| 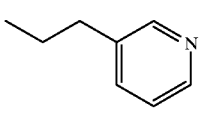 | H |
| 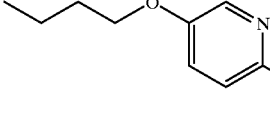 | H |
| 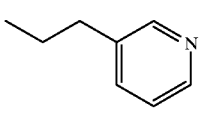 | H |
| 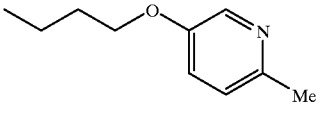 | Me |
| 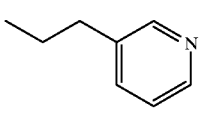 | H |

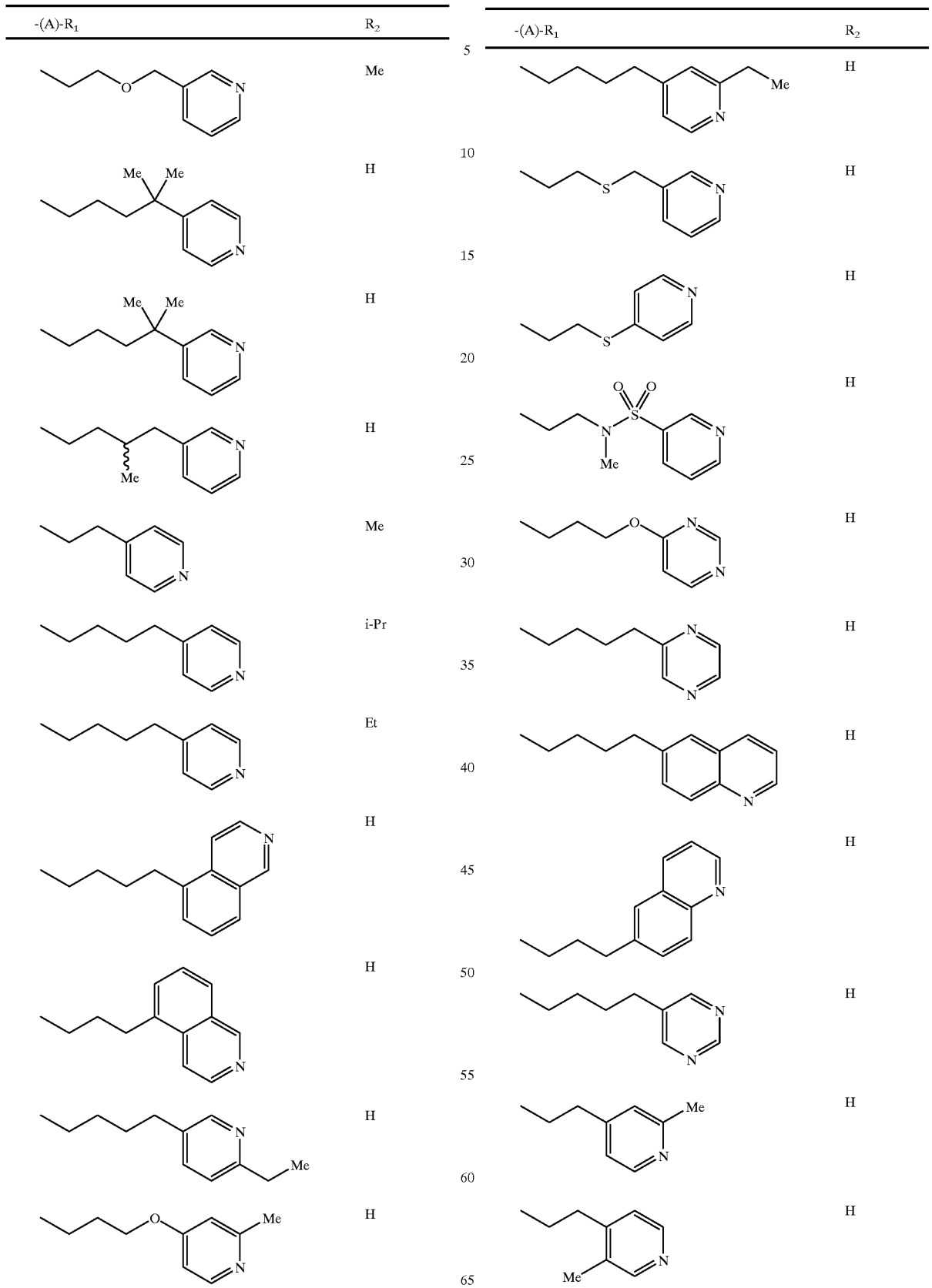

-continued
| -(A)-R₁ | R₂ |
|---|---|
| 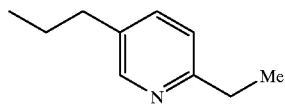 |  |
| 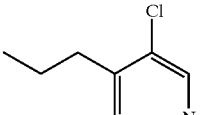 | H |
| 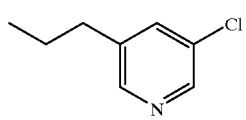 | H |
| 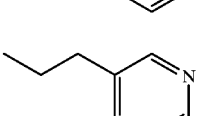 | H |
| 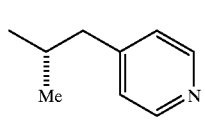 | H |
| 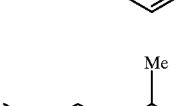 | H |
| 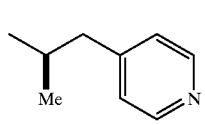 | H |
| 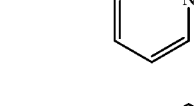 | H |
| 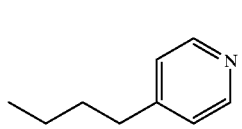 | H |
| 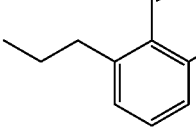 | H |
| 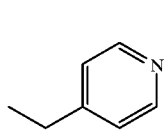 | H |
| 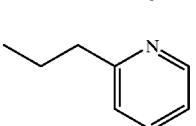 | H |
-continued
| -(A)-R₁ | R₂ |
|---|---|
| 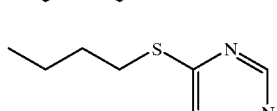 | H |
| 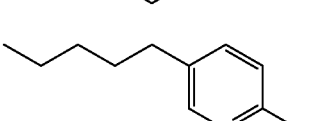 | H |
| 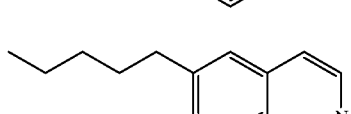 | H |
| 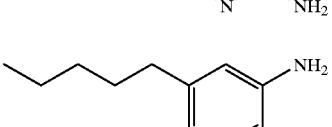 | H |
| 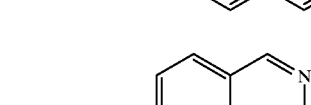 | H |
| 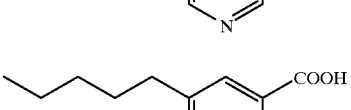 | H |
| 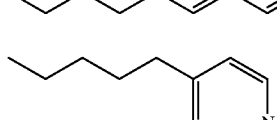 | H |
| 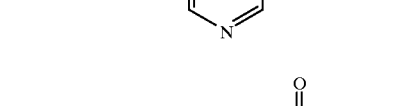 | H |
| 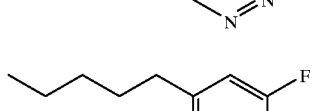 | H |
| 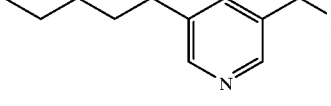 | H |
|  | H |
| 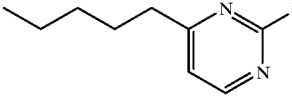 | H |

-continued
| -(A)-R$_1$ | R$_2$ |
|---|---|
| 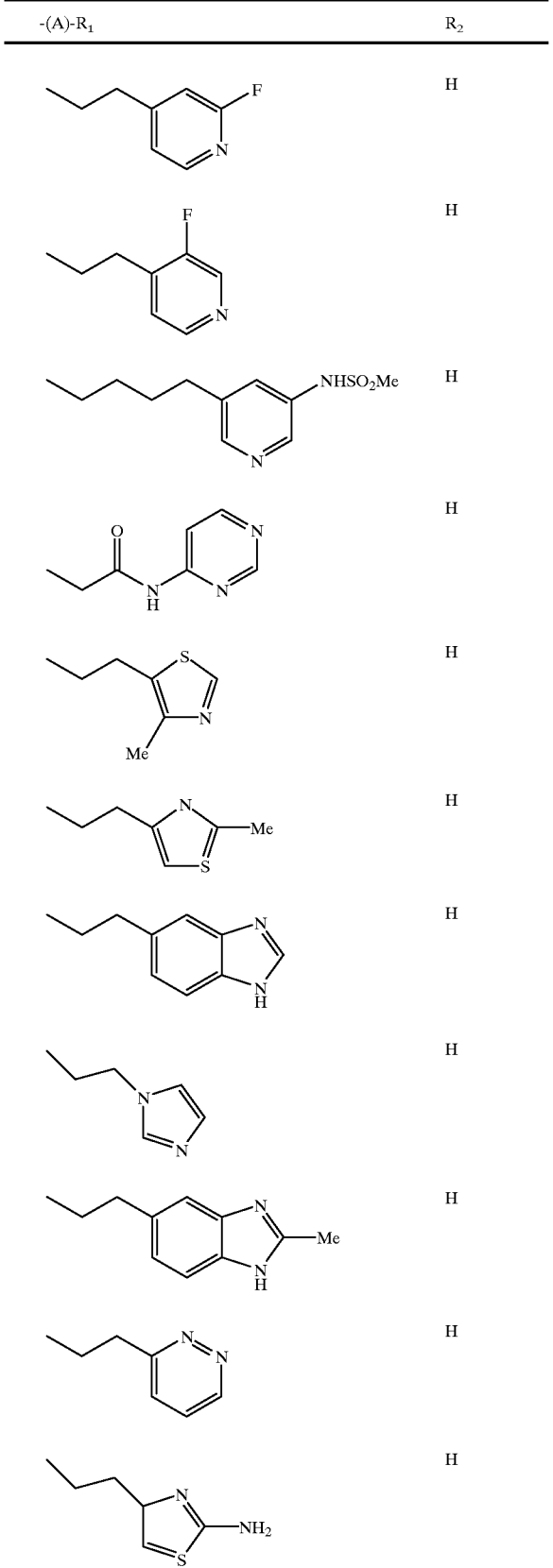 | H H H H H H H H H H H |
-continued
| -(A)-R$_1$ | R$_2$ |
|---|---|
| 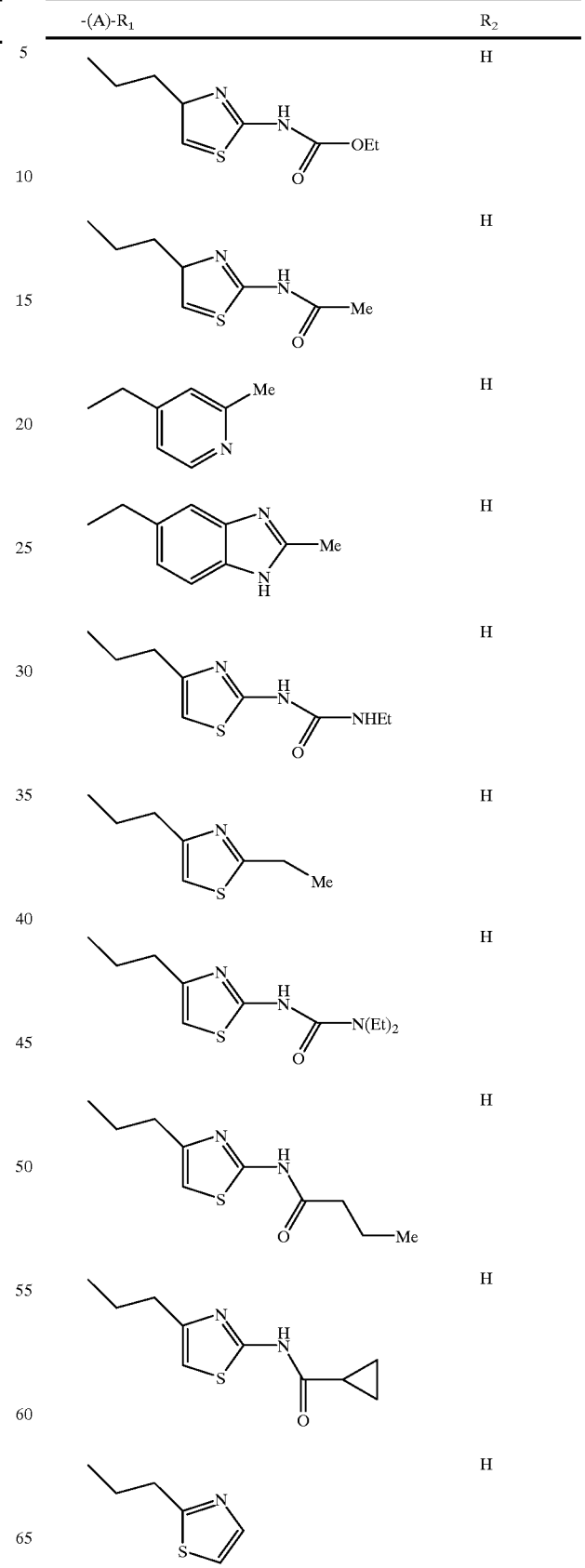 | H H H H H H H H H H |

-continued

| -(A)-R$_1$ | R$_2$ |
|---|---|
| [4-propyl-thiazole] | H |
| [4-propyl-thiazol-2-yl-methanol] | H |
| [4-propyl-thiazole-2-carboxylic acid] | H |
| [5-propyl-1H-benzotriazole] | H |
| [5-propyl-1-methyl-benzotriazole] | H |
| [6-propyl-1-methyl-benzotriazole] | H |
| [5-propyl-2-methyl-benzotriazole] | H |
| [5-propyl-1H-indazole] | H |
| [4-propyl-pyridine N-oxide] | H |

-continued

| -(A)-R$_1$ | R$_2$ |
|---|---|
| [4-propyl-2-methyl-pyridine N-oxide] | H |
| [4-propyl-2,6-dimethyl-pyridine N-oxide] | H |
| [4-propyl-2-trifluoromethyl-pyridine N-oxide] | H |
| [5-propyl-1-methyl-pyridin-2(1H)-one] | H |
| [5-propyl-1-methyl-pyrimidin-2(1H)-one] | H. |

2. The compound of the formula

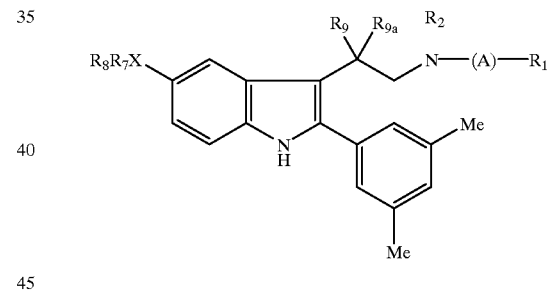

or a pharmaceutically acceptable addition salt and/or hydrate thereof, or where applicable, a geometric or optical isomer or racemic mixture thereof;

wherein R$_1$, R$_2$, R$_9$, R$_{9a}$, X-R$_7$R$_8$ and A are as indicated in the table below:

| X—R$_7$R$_8$ | —(A)—R$_1$ | R$_2$ | R$_9$, R$_{9a}$ |
|---|---|---|---|
| [azabicyclic-N-C(O)-C(Me)$_2$—] | [—CH$_2$CF$_2$—(3-pyridyl) with ethyl] | H | H, H |

-continued

| X—R7R8 | —(A)—R1 | R2 | R9, R9a |
|---|---|---|---|
| (bicyclic N-C(=O)-Et) | (pentyl-4-pyridyl) | H | H, H |
| (bicyclic N-C(=O)-C(Me)(Et)-Me) | (pentyl-4-pyridyl) | H | H, H |
| (bicyclic N-C(=O)-C(Me)(Et)H) | (pentyl-4-pyridyl) | H | H, H |
| (bicyclic N-C(=O)-C(Me)(Me)-) | (pentyl-4-pyridyl) | H | Me, Me |
| (bicyclic N-C(=O)-C(cyclobutyl)(Me)) | (pentyl-4-pyridyl) | H | H, H |
| (3,3-dimethylazetidine-N-C(=O)-C(Me)(Me)-) | (pentyl-4-pyridyl) | H | H, H |
| (quinuclidine-like N-C(=O)-C(Me)(Me)-) | (pentyl-4-pyridyl) | H | H, H |

3. The compound of the formula

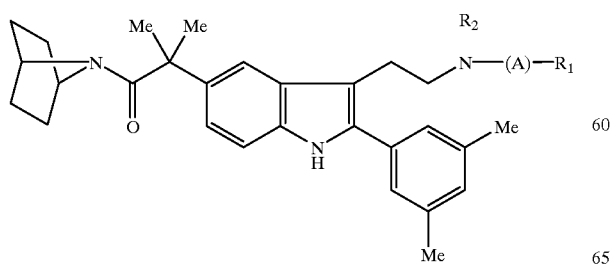

or a pharmaceutically acceptable addition salt and/or hydrate thereof, or where applicable, a geometric or optical isomer or racemic mixture thereof;

wherein $R_1$, $R_2$ and A are as indicated in the table below:
| —(A)—$R_1$ | $R_2$ |
|---|---|
| 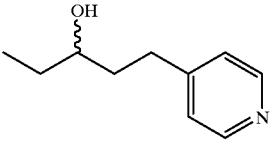 | H |
| 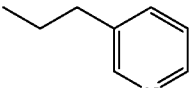 | Me |
| 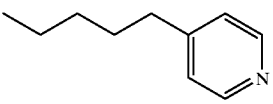 | Et |
| 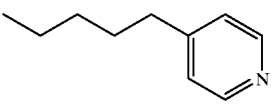 | i-Bu |
| 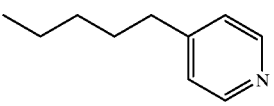 | i-Pr |
| 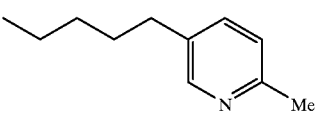 | H |
| 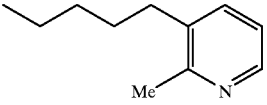 | H |
| 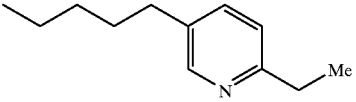 | H |
| 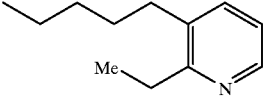 | H |
| 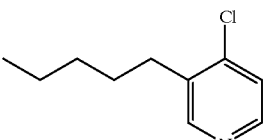 | H |
| 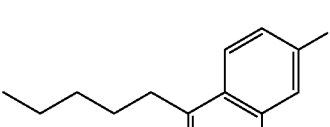 | H |
-continued
| —(A)—$R_1$ | $R_2$ |
|---|---|
| 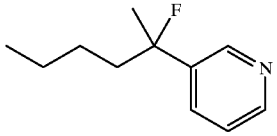 | H |
| 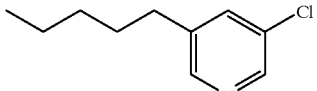 | H |
| 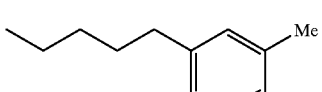 | H |
|  | H |
|  | H |
| 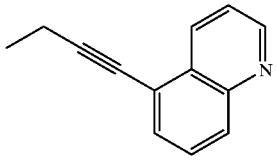 | H |
| 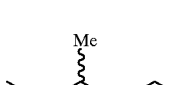 | H |
| 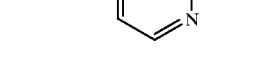 | H |
|  | H |

4. The compound of the formula
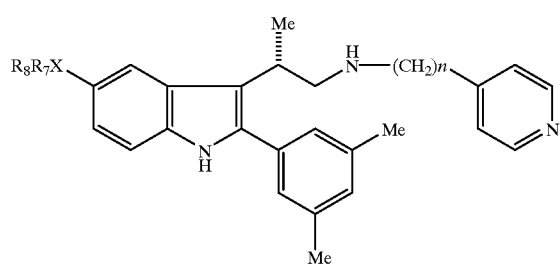
or a pharmaceutically acceptable addition salt and/or hydrate thereof, or where applicable, a geometric or optical isomer or racemic mixture thereof;
wherein X-R$_7$R$_8$ and n are as indicated in the table below:

5. The compound of the formula

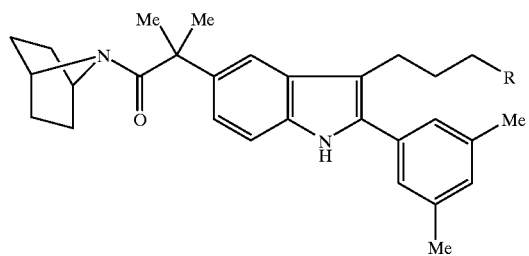

or a pharmaceutically acceptable addition salt and/or hydrate thereof, or where applicable, a geometric or optical isomer or racemic mixture thereof;

| R |
|---|
| 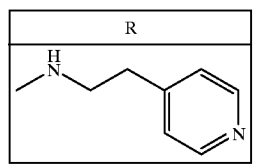 | wherein R is as indicated in the table above.

6. The compound of the formula

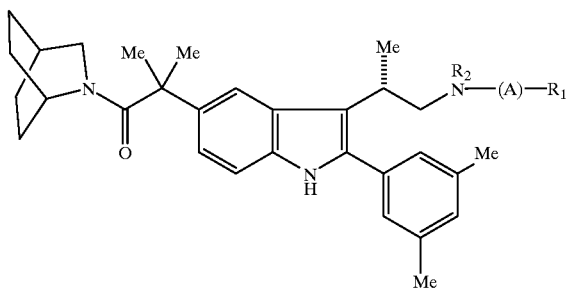

or a pharmaceutically acceptable addition salt and/or hydrate thereof, or where applicable, a geometric or optical isomer or racemic mixture thereof;

wherein $R_1$, $R_2$ and A are as indicated in the table below:

-continued

| —(A)—R₁ | R₂ |
|---|---|
| propyl-tetrazole | H |
| propyl-thiazole-O-C(O)-OEt | H |
| propyl-2,6-dimethylpyridine | H |
| propyl-(3-ethyl)pyridine with Me | H |
| propyl-2-ethylpyridine | H |
| propyl-2-propylpyridine | H |
| propyl-benzimidazole-CF₃ | H |
| propyl-pyridine-NHSO₂Me | H |
| propyl-thiazole-NH-C(O)-NHEt | H |
| propyl-pyridine-CH₂OH | H |
| propyl-2-CF₃-pyridine | H |

-continued

| —(A)—R₁ | R₂ |
|---|---|
| propyl-2-CF₃-pyridine N-oxide | H |
| propyl-indole-N-SO₂Me | H |
| propyl-benzimidazole | H |
| propyl-indole | H |
| propyl-S-(4-methyl-1,2,4-triazole) | H |
| propyl-S-(4-methyl-5-CF₃-1,2,4-triazole) | H |
| propyl-benzimidazole-2-COOMe | H |
| propyl-2-methylpyridine N-oxide | H |
| propyl-3-methylpyridine N-oxide | H |
| propyl-benzotriazole | H |
| propyl-thiophene-COOH | H |

-continued
| —(A)—R$_1$ | R$_2$ |
|---|---|
| 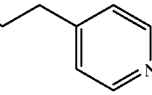 | H |
| 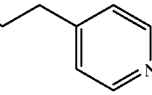 | H |
| 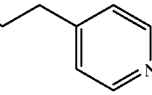 | H |
| 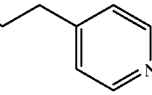 | H |
| 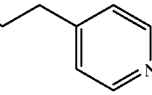 | H |
| 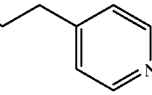 | H |
| 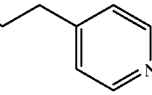 | H |
| 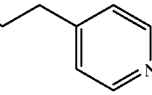 | H |
| 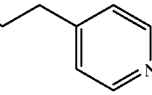 | H |
| 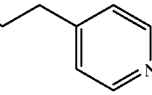 | H |
| 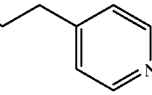 | H |
| 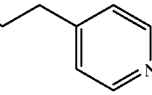 | H |
-continued
| —(A)—R$_1$ | R$_2$ |
|---|---|
|  | H |
7. The compound of the formula
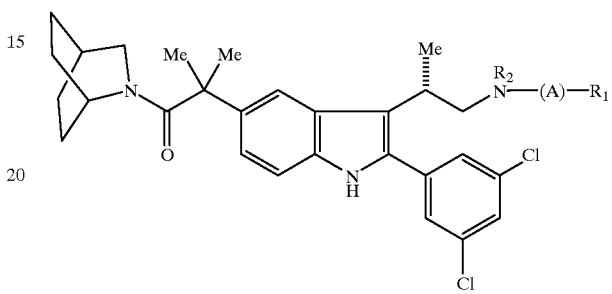
or a pharmaceutically acceptable addition salt and/or hydrate thereof, or where applicable, a geometric or optical isomer or racemic mixture thereof;
wherein R$_1$, R$_2$ and A are as indicated in the table below:
| -(A)-R$_1$ | R$_2$ |
|---|---|
| 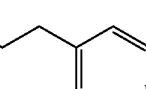 | H |
|  | H |
| 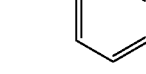 | H |
| 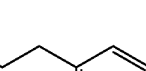 | H |
| 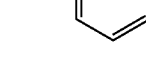 | H |
| 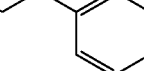 | H |

-continued
| -(A)-R₁ | R₂ |
|---|---|
| 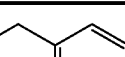 | H |
| 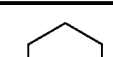 | |
|  | H |
|  | H |
8. The compound of the formula
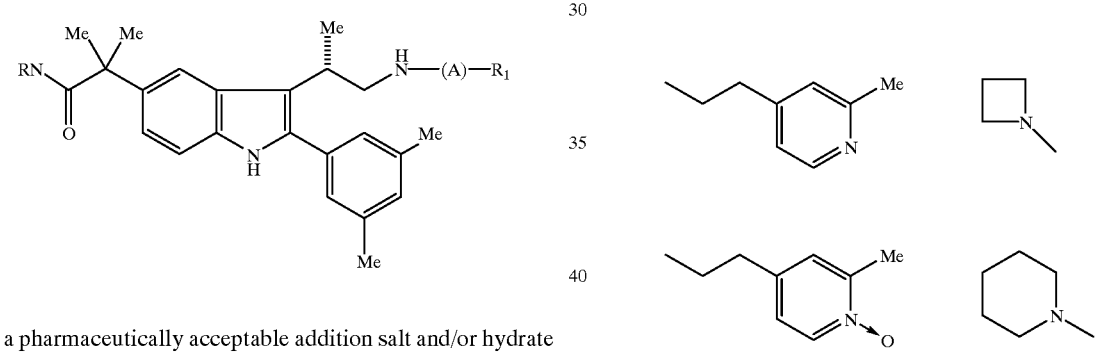
or a pharmaceutically acceptable addition salt and/or hydrate thereof, or where applicable, a geometric or optical isomer or racemic mixture thereof;
wherein R₁, NR and A are as indicated in the table below:
| -(A)-R₁ | —NR |
|---|---|
| 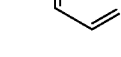 | 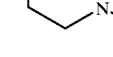 |
| 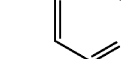 | 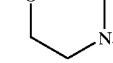 |
|  | 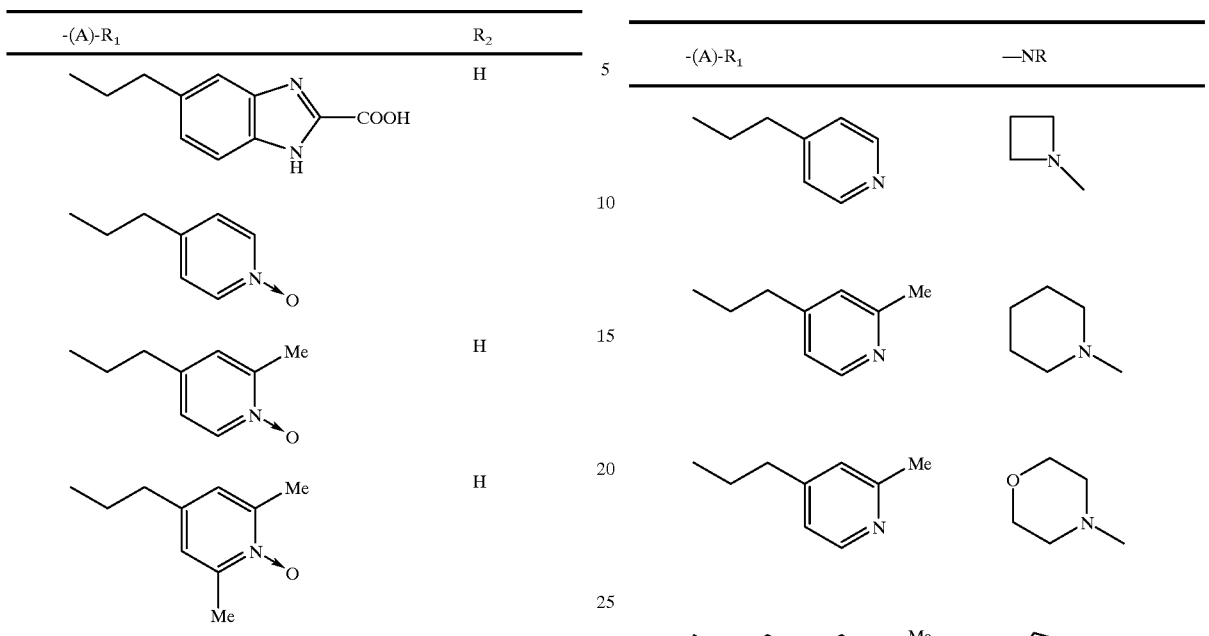 |
-continued
| -(A)-R₁ | —NR |
|---|---|
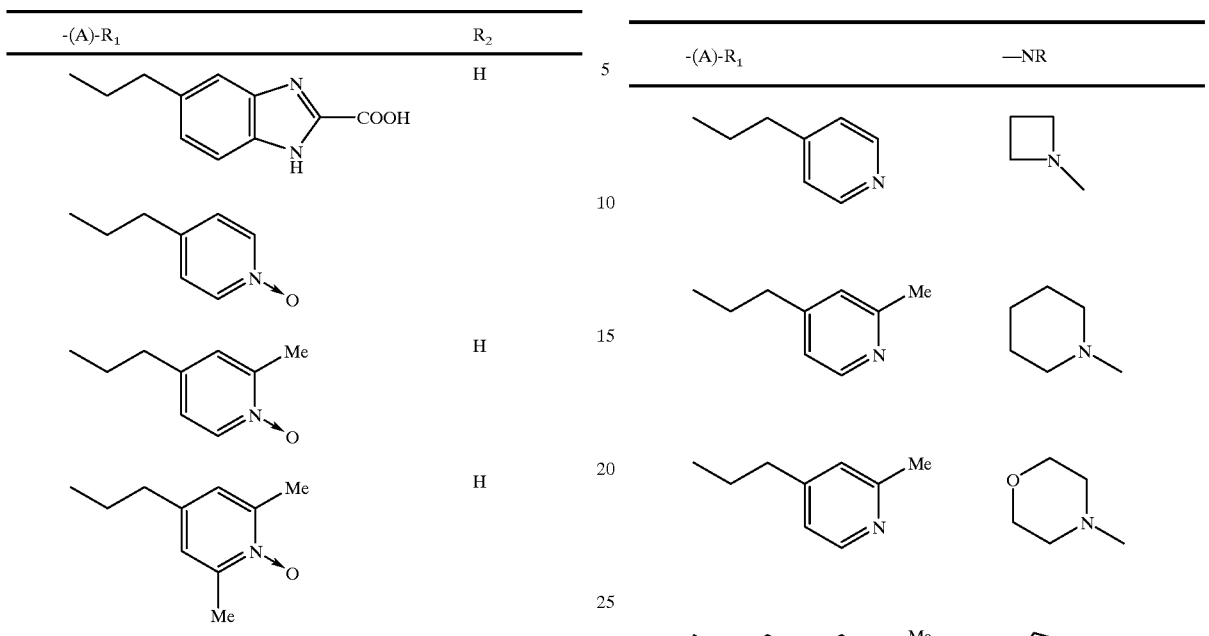

-continued
| -(A)-R₁ | —NR |
|---|---|
| 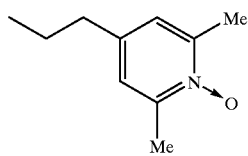 | 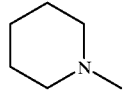 |
| 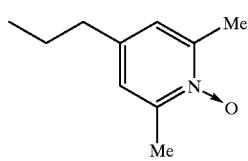 | 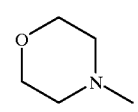 |
-continued
| -(A)-R₁ | —NR |
|---|---|
| 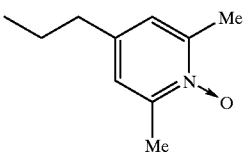 | 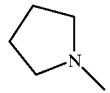 |
| | |
\* \* \* \* \*